(12) United States Patent
Stoltz et al.

(10) Patent No.: US 10,040,784 B2
(45) Date of Patent: Aug. 7, 2018

(54) COMPOSITIONS AND METHODS FOR ACYLATING LACTAMS

(71) Applicant: California Institute of Technology, Pasadena, CA (US)

(72) Inventors: Brian M. Stoltz, San Marino, CA (US); Masaki Hayashi, Kanagawa (JP); Satoshi Hashimoto, Tokyo (JP)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/454,198

(22) Filed: Mar. 9, 2017

(65) Prior Publication Data

US 2017/0260172 A1 Sep. 14, 2017

Related U.S. Application Data

(60) Provisional application No. 62/306,851, filed on Mar. 11, 2016.

(51) Int. Cl.
| | |
|---|---|
| *C07D 409/06* | (2006.01) |
| *C07D 207/27* | (2006.01) |
| *C07D 207/273* | (2006.01) |
| *C07D 207/277* | (2006.01) |

(52) U.S. Cl.
CPC ........ *C07D 409/06* (2013.01); *C07D 207/27* (2013.01); *C07D 207/273* (2013.01); *C07D 207/277* (2013.01)

(58) Field of Classification Search
CPC .............. C07D 207/27; C07D 207/273; C07D 207/277; C07D 409/06
See application file for complete search history.

(56) References Cited

FOREIGN PATENT DOCUMENTS

WO   WO-9525088 A1   9/1995

OTHER PUBLICATIONS

Hayashi et al.(J. Am. Chem. Soc. 2016, 138, 8997-9000).*
International Search Report and Written Opinion for International Application No. PCT/US2017/021528 dated May 25, 2017.
Tasker et al., "Recent advances in homogeneous nickel catalysis," Nature, 509(7500): 299-309 (2014).
Zhang et al., "Direct N-Acylation of Lactams, Oxazolidinones, and Imidazolidinones with Aldehydes by Shvo's Catalyst," Org Lett, 14(17): 4646-4649 (2012).

* cited by examiner

*Primary Examiner* — Valerie Rodriguez-Garcia
(74) *Attorney, Agent, or Firm* — Foley Hong LLP

(57) ABSTRACT

This disclosure provides methods for intermolecular enantioselective C-acylation of lactams with quaternary stereogenic centers by applying a chiral Ni catalyst. The methods comprise treating a lactam with a chiral Ni catalyst, an aryl nitrile, and an aryl halide.

20 Claims, 2 Drawing Sheets

COMPOSITIONS AND METHODS FOR ACYLATING LACTAMS

RELATED APPLICATIONS

This Application claims the benefit of U.S. Provisional Application 62/306,851, filed Mar. 11, 2016, the content of which is incorporated herein by reference.

GOVERNMENT SUPPORT

This disclosure was made with government support under Grant Number GM080269, awarded by the National Institutes of Health. The government has certain rights in the disclosure.

BACKGROUND

The catalytic enantioselective construction of quaternary stereocenters remains a challenging problem in synthetic chemistry. Catalytic enantioselective construction of quaternary stereocenters remains a challenging problem in synthetic chemistry.[1a,2] Catalytic enantioselective reactions of enolates with electrophiles are among the most useful processes to construct quaternary stereocenters.[3] In this area, remarkable success has been achieved in the context of reactions such as enantioselective alkylations, conjugate additions, arylations, and aldol reactions.[1b,c,d]

By contrast, there remains a paucity of enantioselective C-acylation reactions of enolates that enable access to β-keto carbonyl compounds. Recently, intramolecular acyl transfer strategies such as asymmetric Stegich and Black rearrangements have been developed.[4,5] However, limited examples are reported for intermolecular enantioselective C-acylation of enolates or enol ethers.[6,7,8] A challenging issue for C-acylation is competitive O-acylation, leading to mixtures of C- and O-acylated products.[9] Fu has reported an excellent strategy for C-acylation of silyl ketene acetals utilizing planar-chiral 4-(pyrrolidino)pyridine (PPY) catalysts, which allows access to cyclic and acyclic β-keto esters with excellent enantioselectivity.[6] Alternative strategies involve isothiourea or thiourea catalyzed C-acylation of silyl ketene acetals as reported by Smith and Jacobsen.[7,8] Consequently, there remains a significant need to develop new reaction protocols that enable access to β-keto carbonyl compounds.

SUMMARY

This disclosure provides methods for intermolecular enantioselective C-acylation of lactams comprising treating a lactam with a chiral Ni catalyst, an aryl nitrile, and an aryl halide.

The present disclosure provides methods for preparing a compound of formula (I):

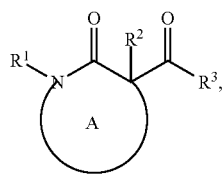

(I)

comprising treating a compound of formula (II):

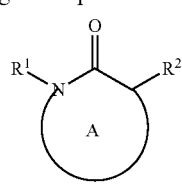

(II)

or a salt thereof;

with a Ni(0) catalyst comprising a chiral ligand;
an aryl nitrile; and
an aryl halide;
wherein, as valence and stability permit, $R^1$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{10}$, —SR$^{10}$, or —NR$^{10}$R$^{11}$;

or $R^1$ or a substituent on ring A taken together with a substituent on ring A and the intervening atoms, form an optionally substituted aryl, heteroaryl, cycloalkyl, cycloalkenyl, heterocycloalkyl, or heterocycloalkenyl group;

$R^2$ represents substituted or unsubstituted alkyl, alkenyl, alkynyl, aralkyl, aralkenyl, aryl, heteroaralkyl, heteroaralkenyl, heteroaryl, (cycloalkyl)alkyl, cycloalkyl, (heterocycloalkyl)alkyl, heterocycloalkyl, alkoxy, amino, or halo;

$R^{10}$ and $R^{11}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl; and ring A represents an optionally substituted heterocycloalkyl or heterocycloalkenyl group.

DETAILED DESCRIPTION

I. Definitions

Figure 1:
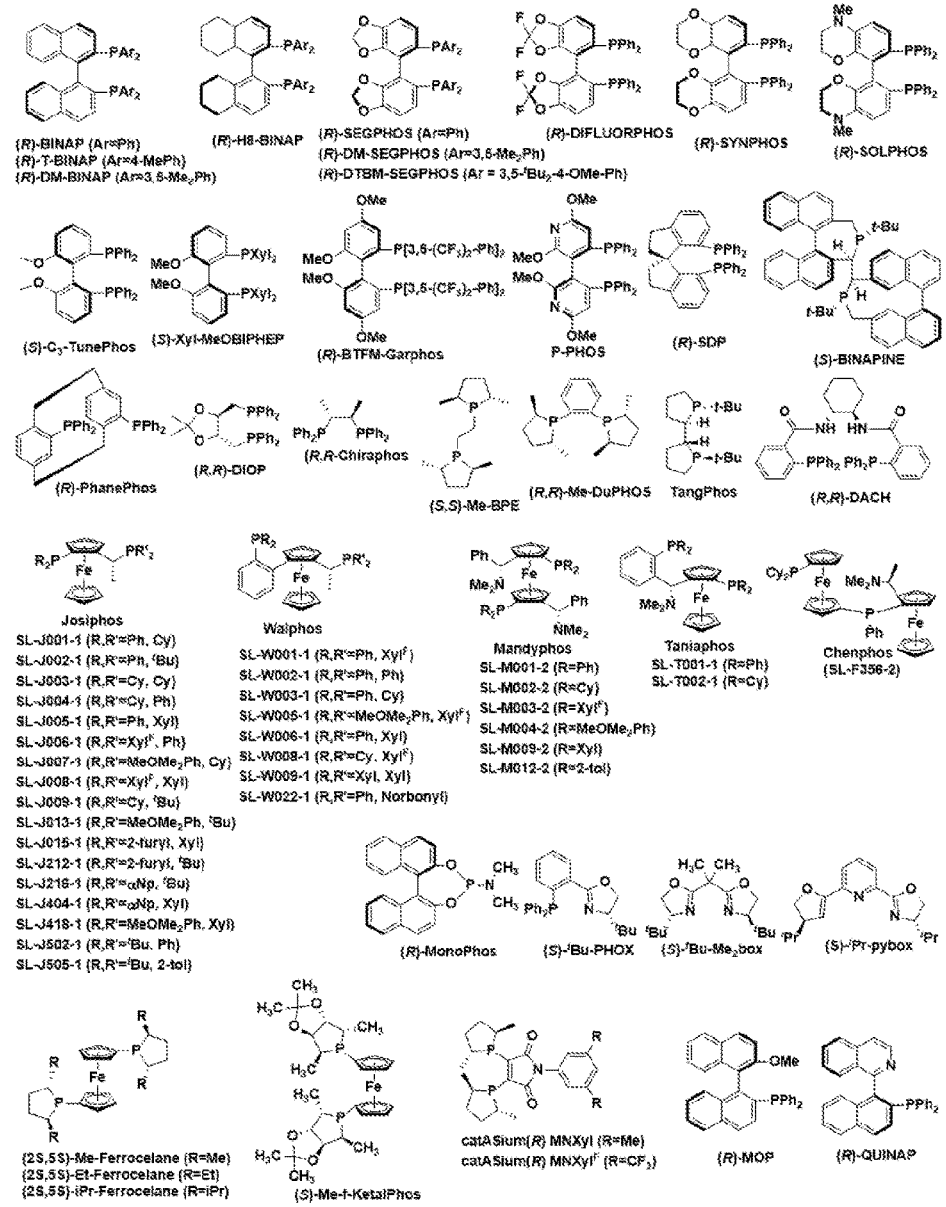
FIG. 1 shows structure of exemplary enantioenriched phosphine ligands.

The definitions for the terms described below are applicable to the use of the term by itself or in combination with another term.

The term "acyl" is art-recognized and refers to a group represented by the general formula hydrocarbyl-C(O)—, preferably alkyl-C(O)—.

The term "acylamino" is art-recognized and refers to an amino group substituted with an acyl group and may be represented, for example, by the formula hydrocarbyl-C(O)NH—.

The term "acyloxy" is art-recognized and refers to a group represented by the general formula hydrocarbylC(O)O—, preferably alkylC(O)O—.

The term "alkoxy" refers to an alkyl group, preferably a lower alkyl group, having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkenyl", as used herein, refers to an aliphatic group containing at least one double bond that is straight chained or branched and has from 1 to about 20 carbon atoms, preferably from 1 to about 10 unless otherwise defined. The term "alkenyl" is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated.

An "alkyl" group or "alkane" is a straight chained or branched non-aromatic hydrocarbon which is completely saturated. Typically, a straight chained or branched alkyl group has from 1 to about 20 carbon atoms, preferably from 1 to about 10 unless otherwise defined. Examples of straight chained and branched alkyl groups include methyl, ethyl, n-propyl, iso-propyl, n-butyl, sec-butyl, tert-butyl, pentyl, hexyl, pentyl and octyl. A $C_1$-$C_6$ straight chained or branched alkyl group is also referred to as a "lower alkyl" group.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. Such substituents, if not otherwise specified, can include, for example, a halogen, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate. For instance, the substituents of a substituted alkyl may include substituted and unsubstituted forms of amino, azido, imino, amido, phosphoryl (including phosphonate and phosphinate), sulfonyl (including sulfate, sulfonamido, sulfamoyl and sulfonate), and silyl groups, as well as ethers, alkylthiols, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, alkylthios, aminoalkyls, carbonyl-substituted alkyls, —$CF_3$, —CN, and the like.

The term "$C_{x-y}$" when used in conjunction with a chemical moiety, such as, acyl, acyloxy, alkyl, alkenyl, alkynyl, or alkoxy is meant to include groups that contain from x to y carbons in the chain. For example, the term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-tirfluoroethyl, etc. $C_0$ alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "alkylamino", as used herein, refers to an amino group substituted with at least one alkyl group.

The term "alkylthio", as used herein, refers to a thiol group substituted with an alkyl group and may be represented by the general formula alkyl-S—.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated.

The term "amide", as used herein, refers to a group

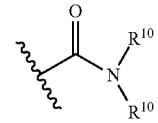

wherein each $R^{10}$ independently represent a hydrogen or hydrocarbyl group, or two $R^{10}$ are taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

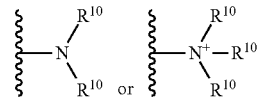

wherein each $R^{10}$ independently represents a hydrogen or a hydrocarbyl group, or two $R^{10}$ are taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group. An aralkyl group is connected to the rest of the molecule through the alkyl component of the aralkyl group.

The term "aralkenyl", as used herein, refers to an alkenyl group substituted with an aryl group.

The term "aryl" as used herein include substituted or unsubstituted single-ring aromatic groups in which each atom of the ring is carbon. Preferably the ring is a 5- to 10-membered ring, more preferably a 6- to 10-membered ring or a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like. Exemplary substitution on an aryl group can include, for example, a halogen, a haloalkyl such as trifluoromethyl, a hydroxyl, a carbonyl (such as a carboxyl, an alkoxycarbonyl, a formyl, or an acyl such as an alkylC(O)), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a silyl ether, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

The term "carbamate" is art-recognized and refers to a group

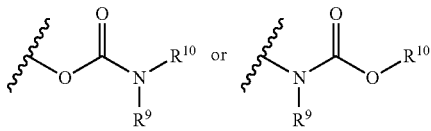

wherein $R^9$ and $R^{10}$ independently represent hydrogen or a hydrocarbyl group, such as an alkyl group, or $R^9$ and $R^{10}$ taken together with the intervening atom(s) complete a heterocycle having from 4 to 8 atoms in the ring structure.

The terms "carbocycle", and "carbocyclic", as used herein, refers to a saturated or unsaturated ring in which each atom of the ring is carbon. The term carbocycle includes both aromatic carbocycles and non-aromatic carbocycles. Non-aromatic carbocycles include both cycloalkane rings, in which all carbon atoms are saturated, and cycloalkene rings, which contain at least one double bond. "Carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo [4.2.0] octane, 4,5,6,7-tetrahydro-1H-indene and bicyclo[4.1.0] hept-3-ene. "Carbocycles" may be substituted at any one or more positions capable of bearing a hydrogen atom.

A "cycloalkyl" group is a cyclic hydrocarbon which is completely saturated. "Cycloalkyl" includes monocyclic and bicyclic rings. Typically, a monocyclic cycloalkyl group has from 3 to about 10 carbon atoms, more typically 3 to 8 carbon atoms unless otherwise defined. The second ring of a bicyclic cycloalkyl may be selected from saturated, unsaturated and aromatic rings. Cycloalkyl includes bicyclic molecules in which one, two or three or more atoms are shared between the two rings. The term "fused cycloalkyl" refers to a bicyclic cycloalkyl in which each of the rings shares two adjacent atoms with the other ring. The second ring of a fused bicyclic cycloalkyl may be selected from saturated, unsaturated and aromatic rings. A "cycloalkenyl" group is a cyclic hydrocarbon containing one or more double bonds.

The term "cycloalkylalkyl", as used herein, refers to an alkyl group substituted with a cycloalkyl group.

The term "carbonate" is art-recognized and refers to a group —OCO$_2$—R$^{10}$, wherein R$^{10}$ represents a hydrocarbyl group.

The term "carboxyl", as used herein, refers to a group represented by the formula —CO$_2$H.

The term "ester", as used herein, refers to a group —C(O)OR$^{10}$ wherein R$^{10}$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O-heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a heteroaryl group.

The terms "hetaralkenyl" and "heteroaralkenyl", as used herein, refers to an alkenyl group substituted with a heteroaryl group.

The term "heteroalkyl", as used herein, refers to a saturated or unsaturated chain of carbon atoms and at least one heteroatom, wherein no two heteroatoms are adjacent.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include 5- to 10-membered cyclic or polycyclic ring systems, including, for example, pyrrole, furan, thiophene, imidazole, oxazole, thiazole, pyrazole, pyridine, pyrazine, pyridazine, and pyrimidine, and the like. Exemplary optional substituents on heteroaryl groups include those substituents put forth as exemplary substituents on aryl groups, above.

The term "heteroatom" as used herein means an atom of any element other than carbon or hydrogen. Preferred heteroatoms are nitrogen, oxygen, and sulfur.

The terms "heterocycloalkyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocycloalkyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocycloalkyls. Heterocycloalkyl groups include, for example, piperidine, piperazine, pyrrolidine, morpholine, lactones, lactams, and the like.

The term "heterocycloalkylalkyl", as used herein, refers to an alkyl group substituted with a heterocycle group.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to, aryl, heteroaryl, carbocycle, heterocyclyl, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer non-hydrogen atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The term "carbamate" is art-recognized and refers to a group —CN.

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "silyl" refers to a silicon moiety with three hydrocarbyl moieties attached thereto. A "silyl ether" refers to a silyl group linked through an oxygen to a hydrocarbyl group. Exemplary silyl ethers include —OSi(CH$_3$)$_3$ (—OTMS), —OSi(CH$_3$)$_2$-Bu (—OTBS), —OSi(Ph)$_{2t}$-Bu (—OTBDPS), and —OSi(iPr)$_3$ (—OTIPS).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this disclosure, the heteroatoms such as nitrogen may have hydrogen substituents and/or any permissible substituents of organic compounds described herein which satisfy the valences of the heteroatoms. Substituents can include any substituents described herein, for example, a halogen, a haloalkyl, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an alkyl, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that substituents can themselves be substituted, if appropriate. Unless specifically stated as "unsubstituted," references to chemical moieties herein are understood to include substituted variants. For example, reference to an "aryl" group or moiety implicitly includes both substituted and unsubstituted variants.

The term "sulfate" is art-recognized and refers to the group —OSO$_3$H, or a pharmaceutically acceptable salt thereof.

The term "sulfonamide" is art-recognized and refers to the group represented by the general formulae

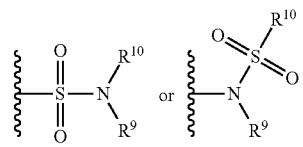

wherein R$^9$ and R$^{10}$ independently represents hydrogen or hydrocarbyl, such as alkyl, or R$^9$ and R$^{10}$ taken together with the intervening atom(s) complete a heterocycle having from 4 to 8 atoms in the ring structure.

The term "sulfoxide" is art-recognized and refers to the group —S(O)—R$^{10}$, wherein R$^{10}$ represents a hydrocarbyl.

The term "sulfonate" is art-recognized and refers to the group SO$_3$H, or a pharmaceutically acceptable salt thereof. In some embodiments, a sulfonate can mean an alkylated sulfonate of the formula SO$_3$(alkyl).

The term "sulfone" is art-recognized and refers to the group —S(O)$_2$—R$^{10}$, wherein R$^{10}$ represents a hydrocarbyl.

The term "thioalkyl", as used herein, refers to an alkyl group substituted with a thiol group.

The term "thioester", as used herein, refers to a group —C(O)SR$^{10}$ or —SC(O)R$^{10}$ wherein R$^{10}$ represents a hydrocarbyl.

The term "thioether", as used herein, is equivalent to an ether, wherein the oxygen is replaced with a sulfur.

The term "urea" is art-recognized and may be represented by the general formula

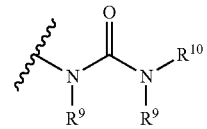

wherein R$^9$ and R$^{10}$ independently represent hydrogen or a hydrocarbyl, such as alkyl, or either occurrence of R$^9$ taken together with R$^{10}$ and the intervening atom(s) complete a heterocycle having from 4 to 8 atoms in the ring structure.

"Protecting group" refers to a group of atoms that, when attached to a reactive functional group in a molecule, mask, reduce or prevent the reactivity of the functional group. Typically, a protecting group may be selectively removed as desired during the course of a synthesis. Examples of protecting groups can be found in Greene and Wuts, *Protective Groups in Organic Chemistry*, 3rd Ed., 1999, John Wiley & Sons, NY and Harrison et al., *Compendium of Synthetic Organic Methods*, Vols. 1-8, 1971-1996, John Wiley & Sons, NY. Representative nitrogen protecting groups include, but are not limited to, formyl, acetyl, trifluoroacetyl, benzyl, benzyloxycarbonyl ("CBZ"), tert-butoxycarbonyl ("Boc"), trimethylsilyl ("TMS"), 2-trimethyl-silyl-ethanesulfonyl ("TES"), trityl and substituted trityl groups, allyloxycarbonyl, 9-fluorenylmethyloxycarbonyl ("FMOC"), nitro-veratryloxycarbonyl ("NVOC") and the like. Representative hydroxyl protecting groups include, but are not limited to, those where the hydroxyl group is either acylated (esterified) or alkylated such as benzyl and trityl ethers, as well as alkyl ethers, tetrahydropyranyl ethers, trialkylsilyl ethers (e.g., TMS or TIPS groups), glycol ethers, such as ethylene glycol and propylene glycol derivatives and allyl ethers.

II. Description

This disclosure is based on the discovery of a novel C-acylation reaction that generates an α-quaternary substituted lactam. The methods comprise treating a lactam with a chiral Ni catalyst, an aryl nitrile, and an aryl halide. For example, the Ni-catalyzed three-component coupling of lactam enolates, benzonitriles, and aryl halides produce β-keto lactams after treatment with acid. Use of a ligand, preferably a chiral ligand, and the addition of LiBr enables the construction of quaternary stereocenters on α-substituted lactams to form β-keto lactams.

According to embodiments of the present disclosure, a wide range of structurally-diverse, functionalized products are prepared by a stereoselective method of nickel-catalyzed enantioselective enolate acylation. This chemistry is useful in the synthesis of lactams, such as β-lactam antibiotics, and for the construction of novel building blocks for medicinal and polymer chemistry.

III. Methods of the Disclosure

In certain aspects, the present disclosure provides for the preparation of a compound of formula (I):

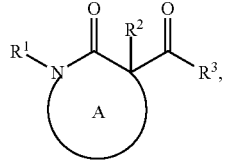
(I)

comprising treating a compound of formula (II):

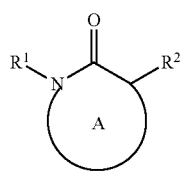
(II)

or a salt thereof;
with a Ni(0) catalyst comprising a chiral ligand;
an aryl nitrile; and
an aryl halide;
wherein, as valence and stability permit,
$R^1$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{10}$, —SR$^{10}$, or —NR$^{10}$R$^{11}$;
or $R^1$ or a substituent on ring A taken together with a substituent on ring A and the intervening atoms, form an optionally substituted aryl, heteroaryl, cycloalkyl, cycloalkenyl, heterocycloalkyl, or heterocycloalkenyl group;
$R^2$ represents substituted or unsubstituted alkyl, alkenyl, alkynyl, aralkyl, aralkenyl, aryl, heteroaralkyl, heteroaralkenyl, heteroaryl, (cycloalkyl)alkyl, cycloalkyl, (heterocycloalkyl)alkyl, heterocycloalkyl, alkoxy, amino, or halo;
$R^{10}$ and $R^{11}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl; and
ring A represents an optionally substituted heterocycloalkyl or heterocycloalkenyl group.

In certain embodiments, the compound of formula (I) is represented by formula (Ia):

(Ia)

and the compound of formula (II) is represented by formula (IIa):

(IIa)

wherein:
$R^4$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{10}$, —SR$^{10}$, or —NR$^{10}$R$^{11}$;
$R^5$ and $R^6$ each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, arylalkoxy, alkylamino, alkylthio, hydroxyalkyl, alkoxyalkyl, aminoalkyl, thioalkyl, haloalkyl, ether, thioether, ester, amido, thioester, carbonate, carbamate, urea, sulfonate, sulfone, sulfoxide, sulfonamide, acyl, acyloxy, or acylamino;
B, D, and E independently for each occurrence represent, as valence permits, O, S, NR$^4$, CR$^5$R$^6$, C(O), CR$^5$, or N; provided that no two adjacent occurrences of N, B, D, and E are NR$^4$, O, S, or N;

or any two occurrences of $R^1$, $R^4$, $R^5$, and $R^6$ on adjacent N, B, D, or E groups, taken together with the intervening atoms, form an optionally substituted aryl, heteroaryl, cycloalkyl, cycloalkenyl, heterocycloalkyl, or heterocycloalkenyl group;

each occurrence of ⎓ independently represents a double bond or a single bond as permitted by valence; and m and n are integers each independently selected from 0, 1, and 2.

In certain embodiments, the sum of m and n is 0, 1, 2, or 3; that is, ring A is a 4-7 membered ring.

In certain embodiments, ring A is a heterocyclic ring.

In certain such embodiments, each occurrence of B, D, and E is independently —$CR^5R^6$—, or —$CR^5$—, or —C(O)—. In certain embodiments, E is —$CR^5$—; and the sum of m and n is 0; that is, ring A is a 4 membered ring. In certain embodiments, $R^5$ is selected from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, alkylamino, amido, and acylamino.

In certain embodiments, ring A contains one or more double bonds, e.g., one or more carbon-carbon double bonds.

In certain embodiments, the compound of formula (I) is represented by formula (Ib):

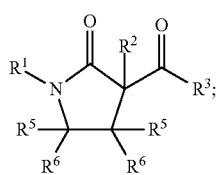

(Ib)

and the compound of formula (II) is represented by formula (IIb):

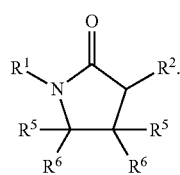

(IIb)

In some embodiments of the compounds disclosed herein, $R^1$ is selected from optionally substituted alkyl, aryl, aralkyl, heteroaryl, heteroaralkyl, alkenyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), and —S(O)$_2$(aryl);

$R^5$ is selected from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, alkylamino, amido, and acylamino; or $R^1$ and the occurrence of $R^5$ on E are taken together to form an optionally substituted heteroaryl, heterocycloalkyl, or heterocycloalkenyl group.

In some embodiments, $R^1$ is selected from optionally substituted alkyl, aryl, aralkyl, heteroaryl, heteroaralkyl, alkenyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), and —S(O)$_2$(aryl); and $R^5$ is selected from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, alkylamino, amido, and acylamino.

In some embodiments, $R^1$ is selected from optionally substituted alkyl, aryl, aralkyl, alkenyl, —C(O)alkyl, —C(O)O(alkyl), —C(O)O(aryl), —C(O)O(aralkyl), and —S(O)$_2$(aryl). In some embodiments, $R^1$ is substituted aryl.

In some embodiments, $R^1$ is a protecting group. In some embodiments, $R^1$ is optionally substituted aralkyl, alkenyl, —C(O)alkyl, —C(O)O(alkyl), and —C(O)O(aralkyl). In some embodiments, $R^1$ is selected from acetyl, trifluoroacetyl, benzyl, benzyloxycarbonyl ("CBZ"), tert-butoxycarbonyl ("Boc"), trityl (e.g., triphenylamine) and substituted trityl groups, allyloxycarbonyl, 9-fluorenylmethyloxycarbonyl ("FMOC"), nitro-veratryloxycarbonyl ("NVOC"), and benzylidenenamine.

In certain embodiments, $R^1$ and the occurrence of $R^5$ on E are taken together to form an optionally substituted heteroaryl, heterocycloalkyl, or heterocycloalkenyl group. In certain embodiments, $R^1$ and the occurrence of $R^5$ on E are taken together to form an optionally substituted heterocycloalkyl or heterocycloalkenyl group. For example, a 4-membered lactam can be fused to an optionally substituted heterocycloalkyl or heterocycloalkenyl group. For example, a penicillin, a cephalosporin, or a penem can be formed.

In certain embodiments, $R^2$ represents substituted or unsubstituted alkyl, alkenyl, alkynyl, aralkyl, aralkenyl, aryl, heteroaralkyl, heteroaralkenyl, heteroaryl, (cycloalkyl)alkyl, cycloalkyl, (heterocycloalkyl)alkyl, heterocycloalkyl, or halo. In certain embodiments, $R^2$ is selected from alkyl, alkenyl, aryl, aralkyl, aralkenyl, or heteroaralkenyl, optionally substituted with halo, alkyl, haloalkyl, hydroxy, alkoxy, aryloxy, arylalkoxy, cyano, nitro, azido, —CO$_2$H, —C(O)O(alkyl), amino, alkylamino, arylamino, aralkylamino, or amido. In certain embodiments, $R^2$ is selected from alkyl, alkenyl, aryl, aralkyl, aralkenyl, or heteroaralkenyl, optionally substituted with halo, alkyl, haloalkyl, alkoxy, aryloxy, or arylalkoxy.

In certain embodiments, the aryl nitrile is an optionally substituted benzonitrile or a napthonitrile. In certain embodiments, the benzonitrile or the napthonitrile is optionally substituted with halo, alkyl, haloalkyl, hydroxy, alkoxy, aryloxy, arylalkoxy, cyano, nitro, azido, —CO$_2$H, —C(O)O(alkyl), amino, alkylamino, arylamino, aralkylamino, or amido. In certain embodiments, the benzonitrile or the napthonitrile is optionally substituted with halo, alkyl, haloalkyl, or alkoxy.

In certain embodiments, the aryl halide is a phenyl halide. In certain embodiments, the aryl halide is selected from bromobenzene, chlorobenzene, iodobenzene, phenyl triflate, and chlorotoluene.

In certain embodiments, the method for preparing a compound of formula (I) comprises treating a compound of formula (II) with a Ni(0) catalyst comprising a chiral ligand; an aryl nitrile; and an aryl halide under acylation conditions.

In certain embodiments, the acylation conditions under which the compound of formula (II) reacts to form a compound of formula (I) further comprise a base, such as hexamethyl-disilazane sodium salt (NaHMDS), KHMDS, LiHMDS, and lithium tert-butoxide (tBuOLi). In certain embodiments, the base is LiHMDS.

In certain embodiments, the acylation conditions under which the compound of formula (II) reacts to form a compound of formula (I) further comprise a lithium salt, such as LiBr.

In certain embodiments, the acylation conditions under which the compound of formula (II) reacts to form a compound of formula (I) further comprise adding an acidic solution.

In certain embodiments, the method yields a compound of formula (I) that is enantioenriched.

Transition Metal Catalysts

Preferred transition metal catalysts of the disclosure are complexes of nickel (0) comprising a chiral ligand.

It should be appreciated that typical transition metal catalysts having a low oxidation state (e.g., (0) or (I)) suffer from air- and moisture-sensitivity, such that these complexes of transition metals necessitate appropriate handling precautions. This may include the following precautions without limitation: minimizing exposure of the reactants to air and water prior to reaction; maintaining an inert atmosphere within the reaction vessel; properly purifying all reagents; and removing water from reaction vessels prior to use. In certain embodiments, the Ni(0) catalyst is a precatalyst.

Exemplary Ni(0) catalysts that may be used in the methods of the disclosure include Ni[(1,5-cyclooctadiene)$_2$], which is also referred to herein as Ni(COD)$_2$.

In certain embodiments, the transition metal catalysts of the disclosure are complexes of Ni(0) or Ni(II), such as Ni(COD)$_2$, NiCl$_2$, and NiBr$_2$.

In certain embodiments, the transition metal catalysts of the disclosure are complexes of Pd(0) or Pd(II). In certain embodiments, palladium (II) catalysts are typically robust, and are less sensitive to air and moisture than their lower-oxidation state counterparts.

Exemplary Pd (II) catalysts that may be used in the methods of the invention include Pd(OC(O)R$^c$)$_2$, wherein R$^c$ is optionally substituted alkyl, alkenyl, alkynyl, aryl, heteroaryl, aralkyl, heteroaralkyl, cycloalkyl, heterocycloalkyl, (cycloalkyl)alkyl, or (heterocycloalkyl)alkyl. Further exemplary Pd (II) catalysts include Pd(OC(O)R$^c$)$_2$, Pd(OC(=O)CH$_3$)$_2$ (i.e., Pd(OAc)$_2$), Pd(TFA)$_2$, Pd(acac)$_2$, PdCl$_2$, PdBr$_2$, PdCl$_2$(R$^{23}$CN)$_2$ (e.g., Pd(PhCN)$_2$Cl$_2$ and Pd(CH$_3$CN)$_2$Cl$_2$), PdCl$_2$(PR$^{24}$R$^{25}$R$^{26}$)$_2$, [Pd($\eta^3$-allyl)Cl]$_2$, and pre-formed Pd(II)-ligand complex, wherein R$^{23}$, R$^{24}$, R$^{25}$, and R$^{26}$ are independently selected from hydrocarbyl, substituted hydrocarbyl, heteroatom-containing hydrocarbyl, and substituted heteroatom-containing hydrocarbyl. In preferred embodiments, the transition metal catalyst is Pd(OAc)$_2$. Alternatively, the transition metal catalyst is Pd(OC(O)R$^c$)$_2$, wherein R$^c$ is defined above. For example, R$^c$ may be alkyl, substituted by one or more halo or cyano groups.

To improve the effectiveness of the catalysts discussed herein, additional reagents may be employed, including, without limitation, salts, solvents, and other small molecules, such as a chiral ligand (see below). Preferred additives include a lithium salt, such as LiBr. These additives are preferably used in an amount that is in the range of about 0.1 equivalents to about 15 equivalents relative to the amount of the reactant, more preferably in the range of about 0.5 equivalents to about 10 equivalents relative to the reactant, and most preferably in the range of about 2 equivalents to about 7 equivalents relative to the reactant.

In certain embodiments, additives include AgBF$_4$, AgOSO$_2$CF$_3$, AgOC(=O)CH$_3$, and bipyridine. These additives are preferably used in an amount that is in the range of about 1 equivalent to about 5 equivalents relative to the amount of the catalyst.

A low oxidation state of a transition metal, i.e., an oxidation state sufficiently low to undergo oxidative addition, can be obtained in situ, by the reduction of transition metal complexes that have a high oxidation state. Reduction of the transition metal complex can optionally be achieved by adding nucleophilic reagents including, without limitation, tetrabutylammonium hydroxide, tetrabutylammonium difluorotriphenylsilicate (TBAT), tetrabutylammonium fluoride (TBAF), 4-dimethylaminopyridine (DMAP), tetramethylammonium hydroxide (e.g., as the pentahydrate), KOH/1,4,7,10,13,16-hexaoxacyclooctadecane, sodium ethoxide, TBAT/trimethyl-(2-methyl-cyclohex-1-enyloxy)-silane, and combinations thereof. When a nucleophilic reagent is needed for the reduction of the metal complex, the nucleophilic reagent is used in an amount in the range of about 1 mol % to about 20 mol % relative to the reactant, more preferably in the range of about 1 mol % to about 10 mol % relative to the substrate, and most preferably in the range of about 5 mol % to about 8 mol % relative to the substrate.

For example, a Pd(II) complex can be reduced in situ to form a Pd(0) catalyst. Exemplary transition metal complexes that may be reduced in situ, include, without limitation, allylchloro[1,3-bis(2,6-di-iso-propylphenyl)imidazol-2-ylidene]palladium(II), ([2S,3S]-bis[diphenylphosphino]butane)($\eta^3$-allyl)palladium(II) perchlorate, [S]-4-tert-butyl-2-(2-diphenylphosphanyl-phenyl)-4,5-dihydro-oxazole($\eta^3$-allyl)palladium(II) hexafluorophosphate (i.e., [Pd(S-tBu-PHOX)(allyl)]PF6), and cyclopentadienyl($\eta^3$-allyl)palladium(II).

The effectiveness of the catalysts discussed herein can be improved by adding nucleophilic reagents including, without limitation, NaHMDS, KHMDS, LiHMDS, tBuOLi, tetrabutylammonium hydroxide, tetrabutylammonium difluorotriphenylsilicate (TBAT), tetrabutylammonium fluoride (TBAF), 4-dimethylaminopyridine (DMAP), tetramethylammonium hydroxide (e.g., as the pentahydrate), KOH/1,4,7,10,13,16-hexaoxacyclooctadecane, sodium ethoxide, TBAT/trimethyl-(2-methyl-cyclohex-1-enyloxy)-silane, and combinations thereof. When a nucleophilic reagent is added, the nucleophilic reagent is used in an amount in the range of about range of about 0.1 equivalents to about 10 equivalents relative to the amount of the reactant, more preferably in the range of about 0.1 equivalents to about 5 equivalents relative to the reactant, and most preferably in the range of about 0.5 equivalents to about 2 equivalents relative to the reactant.

Accordingly, when describing the amount of transition metal catalyst used in the methods of the disclosure, the following terminology applies. The amount of transition metal catalyst present in a reaction is alternatively referred to herein as "catalyst loading". Catalyst loading may be expressed as a percentage that is calculated by dividing the moles of catalyst complex by the moles of the substrate present in a given reaction. Catalyst loading is alternatively expressed as a percentage that is calculated by dividing the moles of total transition metal (for example, nickel) by the moles of the substrate present in a given reaction.

In certain embodiments, the transition metal catalyst is present under the conditions of the reaction from an amount of about 0.1 mol % to about 20 mol % total nickel relative to the substrate, which is the compound of formula (II). In certain embodiments, the catalyst loading is from about 1 mol % to about 15 mol % total nickel relative to the substrate. In certain embodiments, the catalyst loading is from about 1 mol % to about 14 mol %, about 1 mol % to about 12%, about 1 mol % to about 10%, about 2 mol % to about 9 mol %, about 2.5 mol % to about 8 mol %, about 3 mol % to about 7 mol %, about 3.5 mol % to about 6.5 mol %, or about 4 mol % to about 6 mol % total nickel relative to the substrate. For example, in certain embodiments, the catalyst loading is about 3 mol %, about 4 mol %, about 5 mol %, about 6 mol %, about 7 mol %, about 8 mol %, about 9 mol %, about 10 mol %, about 11 mol %, about 12 mol %, about 13 mol %, or about 14 mol % total nickel. In certain embodiments, the catalyst loading is about 2 mol %, about 2.5 mol %, about 3 mol %, about 3.5 mol %, about 4 mol %, about 4.25 mol %, about 4.5 mol %, about 4.75 mol %, about 5 mol %, about 5.25 mol %, about 5.5 mol %, about 5.75 mol %, about 6 mol %, about 6.5 mol %, about 7 mol %, about 7.5 mol %, about 8 mol %, about 8.5 mol %, or about 9% total nickel.

In certain embodiments, the transition metal catalyst is present under the conditions of the reaction from an amount of about 0.01 mol % to about 10 mol % total palladium relative to the substrate, which is the compound of formula (II). In certain embodiments, the catalyst loading is from about 0.05 mol % to about 5 mol % total palladium relative to the substrate. In certain embodiments, the catalyst loading is from about 0.05 mol % to about 2.5 mol %, about 0.05 mol % to about 2%, about 0.05 mol % to about 1%, about 0.02 mol % to about 5 mol %, about 0.02 mol % to about 2.5 mol %, about 0.02 mol % to about 1 mol %, about 0.1 mol % to about 5 mol %, about 0.1 mol % to about 2.5 mol %, or about 0.1 mol % to about 1 mol % total palladium relative to the substrate. For example, in certain embodiments, the catalyst loading is about 0.01 mol %, about 0.05 mol %, about 0.1 mol %, about 0.15 mol %, about 0.2 mol %, about 0.25 mol %, about 0.3 mol %, about 0.4 mol %, about 0.5 mol %, about 0.6 mol %, about 0.7 mol %, about 0.8 mol %, about 0.9 mol %, about 1 mol %, about 1.5 mol %, about 2 mol %, about 3 mol %, or about 5 mol % total palladium.

Ligands

In certain embodiments, the methods disclosed herein use a Ni(0) catalyst comprising a chiral ligand.

In certain embodiments, the Pd (II) catalyst further comprises a chiral ligand.

One aspect of the disclosure relates to the enantioselectivity of the methods. Enantioselectivity results from the use of chiral ligands during the acylation reaction. Without being bound by theory, the asymmetric environment that is created around the metal center by the presence of chiral ligands produces an enantioselective reaction. The chiral ligand forms a complex with the transition metal (e.g., nickel), thereby occupying one or more of the coordination sites on the metal and creating an asymmetric environment around the metal center. This complexation may or may not involve the displacement of achiral ligands already complexed to the metal. When displacement of one or more achiral ligands occurs, the displacement may proceed in a concerted fashion, i.e., with both the achiral ligand decomplexing from the metal and the chiral ligand complexing to the metal in a single step. Alternatively, the displacement may proceed in a stepwise fashion, i.e., with decomplexing of the achiral ligand and complexing of the chiral ligand occurring in distinct steps. Complexation of the chiral ligand to the transition metal may be allowed to occur in situ, i.e., by admixing the ligand and metal before adding the substrate. Alternatively, the ligand-metal complex can be formed separately, and the complex isolated before use in the alkylation reactions of the present disclosure.

Once coordinated to the transition metal center, the chiral ligand influences the orientation of other molecules as they interact with the transition metal catalyst. Coordination of the metal center with an aryl halide and reaction of the substrate with the aryl halide-metal complex are dictated by the presence of the chiral ligand. The orientation of the reacting species determines the stereochemistry of the products.

Chiral ligands of the disclosure may be bidentate or monodentate or, alternatively, ligands with higher denticity (e.g., tridentate, tetradentate, etc.) can be used. Preferably, the ligand will be substantially enantiopure. By "enantiopure" is meant that only a single enantiomer is present. In many cases, substantially enantiopure ligands (e.g., ee>99%, preferably >99.5%, even more preferably >99.9%) can be purchased from commercial sources, obtained by successive recrystallizations of an enantioenriched substance, or by other suitable means for separating enantiomers.

Exemplary chiral ligands may be found in U.S. Pat. No. 7,235,698, the entirety of which is incorporated herein by reference. In certain embodiments, the chiral ligand is an enantioenriched phosphine ligand. In certain embodiments, the enantioenriched phosphine ligand is a ferrocenyl ligand such as a Mandyphos-type ligand, a Josiphos-type ligand, a Taniaphos-type ligand, or a Walphos-type ligand. Preferred chiral ligands of the disclosure include a Mandyphos-type ligand or a Josiphos-type ligand. In certain embodiments, the Mandyphos-type ligand or the Josiphos-type ligand is selected from SL-M003-2, SL-M004-1, SL-M004-2, SL-M009-1, SL-M009-2, SL-J001-1, SL-J002-1, SL-J003-1, SL-J004-1, SL-J006-1, SL-J007-1, SL-J013-1, SL-J212-1, and SL-J418-1. In some embodiments, the enantioenriched phosphine ligand is selected from (R)-BINAP, (R)-DM-BINAP, (S)-DTBM-SEGPHOS, (R)-BTFM-Garphos, (S)—C$_3$-TunePhos, (R)—P-Phos, (2S,5S)-Me-ferocelane, (2S,5S)-Et-ferocelane, (2S,5S)-Me-f-Ketalphos, SL-M001-2, SL-M003-2, SL-M004-1, SL-M004-2, SL-M009-1, SL-M009-2, SL-J001-1, SL-J002-1, SL-J003-1, SL-J004-1, SL-J006-1, SL-J007-1, SL-J013-1, SL-J212-1, SL-J418-1, SL-W001-1, SL-W002-1, SL-W005-1, SL-W006-1, SL-W008-1, SL-W009-1, and SL-W022-1. In some embodiments, the enantioenriched phosphine ligand is selected from (R)-BINAP, (R)-DM-BINAP, (S)—C$_3$-TunePhos, SL-M001-2, SL-M003-2, SL-M004-1, SL-M004-2, SL-M009-1, SL-M009-2, SL-J001-1, SL-J002-1, SL-J003-1, SL-J004-1, SL-J006-1, SL-J013-1, SL-J212-1, SL-W001-1, SL-W002-1, SL-W005-1, SL-W006-1, SL-W008-1, and SL-W009-1. In some embodiments, the enantioenriched phosphine ligand is selected from (S)-DTBM-SEGPHOS, (R)-BTFM-Garphos, (R)—P-Phos, (2S,5S)-Me-ferocelane, (2S,5S)-Et-ferocelane, (2S,5S)-Me-f-Ketalphos, SL-J007-1, SL-J418-1, and SL-W022-1. The ligand structures are depicted in FIG. 1.

Generally, the chiral ligand is present in an amount in the range of about 0.1 equivalents to about 10 equivalents relative to the amount of total metal from the catalyst, preferably in the range of about 0.1 to about 6 equivalents relative to the amount of total metal from the catalyst, and most preferably in the range of about 0.5 to about 4.5 equivalents relative to the amount of total metal from the catalyst. Alternatively, the amount of the chiral ligand can be measured relative to the amount of the substrate.

In certain embodiments, the ligand is present under the conditions of the reaction from an amount of about 0.1 mol % to about 100 mol % relative to the substrate, which is the compound of formula (II). The amount of ligand present in the reaction is alternatively referred to herein as "ligand loading" and is expressed as a percentage that is calculated by dividing the moles of ligand by the moles of the substrate present in a given reaction. In certain embodiments, the ligand loading is from about 0.5 mol % to about 50 mol %. For example, in certain embodiments, the ligand loading is about 9 mol %, about 10 mol %, about 11 mol %, about 12 mol %, about 13 mol %, about 14 mol %, or about 15 mol %. In certain embodiments, the ligand is in excess of the transition metal catalyst. In certain embodiments, the ligand loading is about 10 times the transition metal catalyst loading.

Where a chiral ligand is used, the reactions of the disclosure may enrich the stereocenter bearing $R^2$ in the product relative to the enrichment at this center, if any, of the starting material. In certain embodiments, the chiral ligand used in the methods of the disclosure yields a compound of formula (I) that is enantioenriched. The level of enantioenrichment of a compound may be expressed as enantiomeric excess (ee). The ee of a compound may be measured by dividing the difference in the fractions of the enantiomers by the sum of the fractions of the enantiomers. For example, if a compound is found to comprise 98% (S)-enantiomer, and 2% (R) enantiomer, then the ee of the compound is (98-2)/(98+2), or 96%. In certain embodiments, the compound of formula (I) has about 5% ee or greater, 10% ee or greater, 15% ee or greater, 20% ee or greater, 25% ee or greater, 30% ee or greater, 40% ee or greater, 50% ee or greater, 60% ee or greater, 70% ee or greater, about 80% ee, about 85% ee, about 88% ee, about 90% ee, about 91% ee, about 92% ee, about 93% ee, about 94% ee, about 95% ee, about 96% ee, about 97% ee, about 98% ee, about 99% ee, or above about 99% ee, even where this % ee is greater than the % ee of the starting material, such as 0% ee (racemic). In certain embodiments, the compound of formula (I) is enantioenriched. In certain embodiments, the compound of formula (I) is enantiopure. In embodiments where the starting material has more than one stereocenter, reactions of the disclosure may enrich the stereocenter bearing $R^2$ relative to the enrichment at this center, if any, of the starting material, and substantially independently of the stereochemical disposition/enrichment (de) of any other stereocenters of the molecule. For example, a product of the methods described herein may have 5% de or greater, 10% de or greater, 15% de or greater, 20% de or greater, 25% de or greater, 30% de or greater, 40% de or greater, 50% de or greater, 60% de or greater, 70% de or greater, 80% de or greater, 90% de or greater, 95% de or greater, or even 98% de or greater at the stereocenter of the product bearing $R^2$.

Acylation Conditions

In certain embodiments, the methods of the disclosure include treating a compound of formula (II) with a Ni(0) catalyst comprising a chiral ligand; an aryl nitrile; and an aryl halide under acylation conditions. In certain embodiments, acylation conditions further comprise a base, such as NaHMDS, KHMDS, LiHMDS, and tBuOLi. In certain embodiments, the base is LiHMDS. In certain embodiments, acylation conditions further comprise a lithium salt. In certain embodiments, the lithium salt is LiBr.

In certain embodiments, acylation conditions of the reaction include one or more organic solvents. In certain embodiments, organic solvents include aromatic or non-aromatic hydrocarbons, ethers, alkylacetates, nitriles, or combinations thereof. In certain embodiments, organic solvents include hexane, pentane, benzene, toluene, xylene, cyclic ethers such as optionally substituted tetrahydrofuran and dioxane, acyclic ethers such as dimethoxyethane, diethyl ether, methyl tertbutyl ether, and cyclopentyl methyl ether, acetonitrile, isobutyl acetate, ethyl acetate, isopropyl acetate, or combinations thereof. In certain preferred embodiments, the solvent is toluene, tetrahydrofuran, dioxane, methyl tert-butyl ether, dimethoxyethane, or a mixture of toluene and tetrahydrofuran. In certain other preferred embodiments, the solvent is a mixture of toluene and tetrahydrofuran. In certain embodiments, the mixture of toluene and tetrahydrofuran is in a ratio of 1:5, 1:2, 1:1, 2:1, 3:1, 4:1, 5:1, 6:1, 7:1, 8:1, 9:1, 10:1, 11:1, 12:1, 13:1, 14:1, or 15:1. In certain embodiments, the mixture of toluene and tetrahydrofuran is in a ratio of 5:1 or 10:1.

In certain embodiments, acylation conditions further comprise adding an acidic solution. In certain embodiments, the acidic solution comprises an acid selected from acetic acid, boric acid, carbonic acid, citric acid, hydrochloric acid, hydrofluoric acid, nitric acid, oxalic acid, phosphoric acid, sulfuric acid, and trifluoracetic acid. In certain embodiments, the acidic solution comprises HCl.

In certain embodiments, acylation conditions of the reaction include a reaction temperature. In certain embodiments, the reaction temperature is ambient temperature (about 20° C. to about 26° C.). In certain embodiments, the reaction temperature is higher than ambient temperature, such as, for example, about 30° C., about 35° C., about 40° C., about 45° C., about 50° C., about 55° C., or about 60° C. Reaction temperature may be optimized per each substrate.

In certain embodiments, instruments such as a microwave reactor may be used to accelerate the reaction time. Pressures range from atmospheric to pressures typically used in conjunction with supercritical fluids, with the preferred pressure being atmospheric.

Exemplification

The disclosure described generally herein will be more readily understood by reference to the following examples, which are included merely for purposes of illustration of certain aspects and embodiments of the present disclosure, and are not intended to limit the disclosure.

List of Abbreviations ee—enantiomeric excess, de—stereochemical disposition/enrichment dr—diastereomeric ratio, HPLC—high-performance liquid, chromatography, SFC—supercritical fluid chromatography, TLC—thin-layer chromatography, AcOEt—ethyl acetate, THF—tetrahydrofuran, MeOH—methanol, MeCN—acetonitrile, IPA—isopropanol, Ni(COD)$_2$—Ni[(1,5-cyclooctadiene)$_2$], BINAP—(2,2'-bis (diphenylphosphino)-1,1ζ-binaphthyl), LiHMDS or LHMDS—lithium hexamethyldisilazide, NaHMDS—sodium hexamethyldisilazide, KHMDS—potassium hexamethyldisilazide, lithium tert-butoxide—tBuOLi, PMP—p-methoxyphenyl, CAN—ceric ammonium nitrate, TFA—trifluoroacetic acid, m-CPBA—m-chloroperoxybenzoic acid, Example 1. Discovery of Ni-Catalyzed C-Acylation An α-acylated product (4a is produced by the reaction of the lithium enolate derived from lactam 1a in the presence of benzonitrile (2a), chlorobenzene (3a), and a Ni(0) pre-catalyst (Table 1, entry 1).[10] Initially, we imagined that 4a could be formed by direct nucleophilic addition of the lithium enolate of lactam 1a to benzonitrile 2a followed by hydrolysis of the resulting imine. Therefore, we conducted a series of control experiments to confirm the reaction pathway. Contrary to our expectations, in the absence of Ni(COD)$_2$ and BINAP the reaction did not produce the product 4a, and only trace amount of product was obtained from the reaction in the absence of ligand (entries 2 and 3). Most interestingly, the reaction did not proceed without aryl chloride 3a (entry 4). Notably, Pd(0) and Ni(II) did not promote the reaction (entries 5 and 6) under these reaction conditions. Finally, as we observed product 4a when substituting chlorotoluene for chlorobenzene in the reaction, we elucidated that the source of the α-benzoyl group present in the product is indeed benzonitrile (2a) and not the corresponding chloroarene.

TABLE 1

Discovery of a Ni-catalyzed enolate acylation

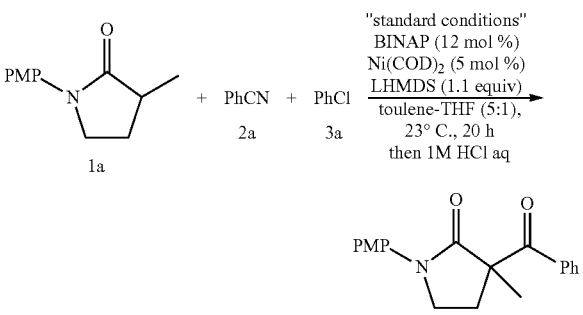

| Entry | Deviation from Standard Conditions | Yield [%] |
|---|---|---|
| 1 | none | 99 |
| 2 | No Ni(COD)$_2$ or (R)-BINAP | 99 |
| 3 | No (R)-BINAP | 99 |
| 4 | No PhCl | 90 |
| 5 | Pd(dba)$_2$ instead of Ni(COD)$_2$ | 99 |
| 6 | NiCl$_2$ instead of Ni(COD)$_2$ | 99 |
| 7 | p-toluoylCl instead of PhCl | 14 |

[b] HPLC conversion.

The standard reaction conditions were lactam (1 equiv), PhCN (2 equiv), aryl chloride (2 equiv), LHMDS (1.1 equiv), Ni(COD)$_2$ (10 mol %), ligand (12 mol %), in 5:1 toluene-THF (0.2 M) at 23° C. for 20 h, then 1 M HCl aq at 23° C. for 0.5 h.

Example 2. Exploration of Chiral Ligand and Solvent

The C-acylation of lactam 1a using a variety of chiral ligands (12 mol %) with Ni(COD)$_2$ (10 mol %) and LHMDS (1.1 equiv) (Table 2) in a range of solvents at 23° C. (Table 3). The ligands of Table 2 are shown in FIG. 1. As a result of this study, Mandyphos-type ligands (e.g., L2 and L3) emerged as promising candidates, displaying good enantioselectivity and reactivity. Further examination revealed that a Josiphos-type ligand (i.e., L4) in TBME promotes the reaction with greater enantioselectivity (~60% ee) and conversion (74%).

General Procedure A for Ligand and Solvent Screen:

To a solution of Ni(COD)$_2$ (1.10 mg, 4.00 µmol, 0.100 equiv) and ligand (4.80 µmol, 0.120 equiv) in solvent (0.1 mL) was added a solution of lactam 1a (8.21 mg, 40.0 µmol, 1.00 equiv), benzonitrile 2a (8.24 µL, 20.0 µmol, 2.00 equiv), chlorobenzene 3a (8.13 µL, 20.0 µmol, 2.00 equiv) and LHMDS (7.36 mg, 44.0 λmol. 1.10 equiv) in solvent (0.1 mL) and the reaction mixture was stirred at 25° C. for 20 h. 1M HCl aqueous solution (0.5 mL) was added and the mixture was stirred at ambient temperature for 0.5 h. AcOEt (0.5 mL) was added and the mixture was stirred for 1 min. The organic layer (10 µL) was sampled and diluted to a mixture of hexanes and IPA (8/2, 1 mL). This solution was analyzed for conversion and enantiomeric excess (see Methods for the Determination of Enantiomeric Excess).

TABLE 2

Assessment of the chiral ligand for the lactam acylation.

| Entry | Ligand | Conversion [%] | ee [%] |
|---|---|---|---|
| 1 | (R)-BINAP | 31 | 7 |
| 2 | (R)-T-BINAP | 61 | 3 |
| 3 | (R)-DM-BINAP | 87 | 7 |
| 4 | (R)-H8-BINAP | 73 | −2 |
| 5 | (R)-SEGPHOS | 1 | −31 |
| 6 | (R)-DM-SEGPHOS | 59 | −1 |
| 7 | (R)-DTBM-SEGPHOS | 26 | −32 |
| 8 | (R)-DIFLUORPHOS | 2 | 8 |
| 9 | (S)-Xyl-MeBIHEP | 66 | 2 |
| 10 | (R)-BTFM-Garphos | 22 | −10 |
| 11 | (R)-SYNPHOS | 45 | −1 |
| 12 | (R)-SOLPHOS | 33 | −3 |
| 13 | (S)-C$_3$-TunePhos | 53 | 6 |
| 14 | (R)-P-Phos | 19 | −5 |
| 15 | (R)-Phanephos | 15 | −2 |
| 16 | (R)-SDP | 16 | 3 |
| 17 | (S)-Monophos | 74 | 1 |
| 18 | (S)-BINAPINE | 8 | 11 |
| 19 | CatASiumMN Xyl (R) | 4 | 13 |
| 20 | CatASiumMN Xyl$^F$ (R) | 6 | 2 |
| 21 | (R,R)-Chiraphos | 0 | — |
| 22 | (R, R)-DIOP | 0 | — |
| 23 | (2S,5S)-MeBPE | 0 | — |
| 24 | (2R,5R)-MeDUPHOS | 0 | — |
| 25 | (R)-MOP | 0 | — |
| 26 | (R)-QUINAP | 0 | — |
| 27 | DATCH-Phenyl | 0 | — |
| 28 | (S)-tBuPHOX | 2 | 10 |
| 29 | (S)-tBu-Mebox | 0 | — |
| 30 | (S)-iPr-ptbox | 0 | — |
| 31 | tangphos | 3 | 7 |
| 32 | (2S,5S)-Me-Ferocelane | 76 | −24 |
| 33 | (2S,5S)-Et-Ferocelane | 25 | −6 |
| 34 | (2S,5S)-iPr-Ferocelane | 1 | 35 |
| 35 | (2S,5S)-Me-f-Ketalphos | 63 | −56 |
| 36 | SL-J001-1 | 80 | 16 |
| 37 | SL-J002-1 | 53 | 13 |
| 38 | SL-J003-1 | 41 | 5 |
| 39 | SL-J004-1 | 54 | 8 |
| 40 | SL-J005-1 | 7 | −8 |
| 41 | SL-J006-1 | 79 | 30 |
| 42 | SL-J007-1 | 85 | −6 |
| 43 | SL-J008-1 | 18 | −1 |
| 44 | SL-J009-1 | 5 | 1 |
| 45 | SL-J013-1 | 32 | 10 |
| 46 | SL-J015-1 | 5 | 2 |
| 47 | SL-J212-1 | 86 | 12 |
| 48 | SL-J216-1 | 4 | −5 |
| 49 | SL-J404-1 | 37 | 1 |
| 50 | SL-J418-1 | 44 | −12 |
| 51 | SL-J502-1 | 4 | −4 |
| 52 | SL-J505-1 | 0 | — |
| 53 | SL-W001-1 | 52 | 20 |
| 54 | SL-W002-1 | 64 | 10 |
| 55 | SL-W003-1 | 9 | −16 |
| 56 | SL-W005-1 | 54 | 14 |
| 57 | SL-W006-1 | 61 | 18 |
| 58 | SL-W008-1 | 19 | 16 |
| 59 | SL-W009-1 | 64 | 7 |

TABLE 2-continued

Assessment of the chiral ligand for the lactam acylation.

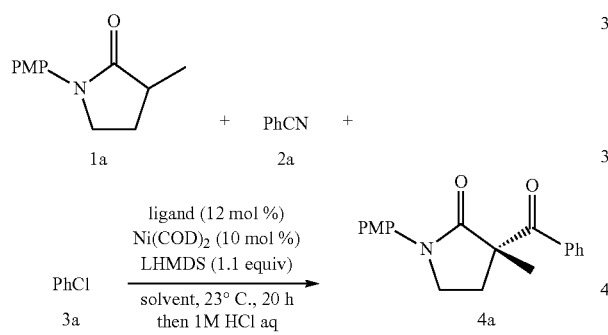

| Entry | Ligand | Conversion [%] | ee [%] |
|---|---|---|---|
| 60 | SL-W022-1 | 7 | −14 |
| 61 | SL-M001-2 | 39 | 35 |
| 62 | SL-M002-2 | 0 | — |
| 63 | SL-M003-2 | 25 | 15 |
| 64 | SL-M004-2 | 70 | 59 |
| 65 | SL-M009-2 | 71 | 62 |
| 66 | SL-M012-2 | 0 | — |
| 67 | SL-T001-1 | 7 | 34 |
| 68 | SL-T002-1 | 0 | — |
| 69 | Chenphos | 0 | — |

Shown above is the scheme for the chiral ligand and solvent screen of Table 3.

TABLE 3

Assessment of the chiral ligand and solvent for the lactam acylation.

| Entry | Ligand | Solvent | Conversion [%] [a] | ee [%] [b] |
|---|---|---|---|---|
| 1 | L1, (R)-BINAP | Toluene | 31 | 7 |
| 2 | L2, SL-M004-1 | Toluene | 70 | 59 |
| 3 | L2, SL-M004-1 | THF | 32 | 15 |
| 4 | L2, SL-M004-1 | Dioxane | 52 | 47 |
| 5 | L2, SL-M004-1 | TBME | 72 | 51 |
| 6 | L2, SL-M004-1 | DME | 53 | 25 |
| 7 | L2, SL-M004-1 | Toluene-THF (5:1) | 53 | 52 |
| 8 | SL-M004-2 | Toluene | 70 | 59 |
| 9 | SL-M004-2 | THF | 32 | 15 |
| 10 | SL-M004-2 | Dioxane | 52 | 47 |
| 11 | SL-M004-2 | TBME | 72 | 51 |
| 12 | SL-M004-2 | DME | 53 | 25 |
| 13 | SL-M004-2 | Toluene-THF (5:1) | 53 | 52 |
| 14 | L3, SL-M009-1 | Toluene | 71 | 62 |
| 15 | L3, SL-M009-1 | THF | 29 | 13 |
| 16 | L3, SL-M009-1 | Dioxane | 42 | 47 |
| 17 | L3, SL-M009-1 | TBME | 42 | 31 |
| 18 | L3, SL-M009-1 | DME | 47 | 21 |
| 19 | L3, SL-M009-1 | Toluene-THF (5:1) | 45 | 53 |
| 20 | SL-M009-2 | Toluene | 71 | 62 |
| 21 | SL-M009-2 | THF | 29 | 13 |
| 22 | SL-M009-2 | Dioxane | 42 | 47 |
| 23 | SL-M009-2 | TBME | 42 | 61 |
| 24 | SL-M009-2 | DME | 47 | 21 |
| 25 | SL-M009-2 | Toluene-THF (5:1) | 45 | 53 |
| 26 | SL-M009-2 | Methylcyclohexane | 48 | 13 |
| 27 | SL-M009-2 | $n$Bu$_2$O | 0 | — |
| 28 | SL-M009-2 | DMF | 0 | — |
| 29 | L4, SL-J006-1 | Toluene | 79 | 30 |
| 30 | L4, SL-J006-1 | THF | 26 | 2 |
| 31 | L4, SL-J006-1 | Dioxane | 52 | 30 |
| 32 | L4, SL-J006-1 | TBME | 74 | 60 |
| 33 | L4, SL-J006-1 | DME | 37 | 6 |
| 34 | L4, SL-J006-1 | Toluene-THF (5:1) | 54 | 41 |
| 35 | L4, SL-J006-1 | Methylcyclohexane | 96 | 25 |
| 36 | L4, SL-J006-1 | $n$Bu$_2$O | 0 | — |
| 37 | L4, SL-J006-1 | DMF | 0 | — |

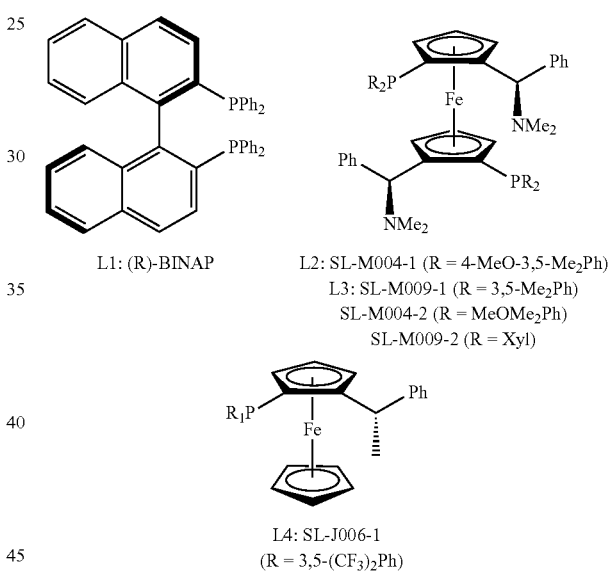

L1: (R)-BINAP
L2: SL-M004-1 (R = 4-MeO-3,5-Me$_2$Ph)
L3: SL-M009-1 (R = 3,5-Me$_2$Ph)
SL-M004-2 (R = MeOMe$_2$Ph)
SL-M009-2 (R = Xyl)

L4: SL-J006-1
(R = 3,5-(CF$_3$)$_2$Ph)

Example 3. Exploration of Bases, Aryl Halides, and Additives

Further studies aimed toward optimization of bases, aryl halides, and additives are summarized in Table 4. Surprisingly, no enantioselectivity was observed in reactions using NaHMDS or KHMDS instead of LHMDS (entries 2-4), indicating that lithium cations are essential for enantioselectivity. Bromobenzene (3b) exhibited superior enantioselectivity and reactivity compared to chlorobenzene (3a, cf. entries 2 and 5), iodobenzene (3c, cf. entries 6 and 5), and phenyl triflate (3d, cf. entries 7 and 5). Encouraged by these results, we examined lithium salt additives. To our delight, reactivity and enantioselectivity were improved dramatically by adding LiBr, especially using the Mandyphos-type ligands (entries 9 and 10). It is conceivable that the size and Lewis acidity of the lithium cation is well suited to coordinate the dimethyl amino groups on the Mandyphos-type ligand in a productive manner (cf entries 9 and 10 vs. 11).

TABLE 4

*Assessment of bases, aryl halides, and additives for the lactam acylation.*

| Entry | Ligand | Base | PhX | Solvent | Additive | Conversion [%] | ee [%] |
|---|---|---|---|---|---|---|---|
| 1 | L4 | tBuOLi | PhCl 3a | TBME | — | 0 | — |
| 2 | L4 | LHMDS | PhCl 3a | TBME | — | 74 | −54 |
| 3 | L4 | NaHMDS | PhCl 3a | TBME | — | 42 | — |
| 4 | L4 | KHMDS | PhCl 3a | TBME | — | 51 | — |
| 5 | L4 | LHMDS | PhBr 3b | TBME | — | 83 | −61 |
| 6 | L4 | LHMDS | PhI 3c | TBME | — | 65 | −55 |
| 7 | L4 | LHMDS | PhOTf 3d | TBME | — | 73 | −28 |
| 8 | L2 | LHMDS | PhBr 3b | Toluene-THF 10:1 | — | 55 | 68 |
| 9 | L2 | LHMDS | PhBr 3b | Toluene-THF 10:1 | LiBr | 98 | 89 |
| 10 | L3 | LHMDS | PhBr 3b | Toluene-THF 10:1 | LiBr | 92 | 89 |
| 11 | L4 | LHMDS | PhBr 3b | Toluene-THF 10:1 | LiBr | 28 | −46 |

The lactams 4a of entries 1-7 were prepared according to the general procedure A with lactam (1 equiv), PhCN (2 equiv), PhX (2 equiv), base (1.1 equiv), Ni(COD)$_2$ (10 mol %), ligand (12 mol %), in TBME (0.2 M) at 23° C. for 20 h, then 1 M HCl aq at 23° C. for 0.5 h. The lactams 4a of entries 8-11 were prepared according to the general procedure A with lactam (2 equiv), PhCN (1 equiv), PhX (1 equiv), base (1.2 equiv), Ni(COD)$_2$ (10 mol %), ligand (12 mol %), in toluene-THF (10:1) (0.2 M) at 23° C. for 20 h, then 1 M HCl aq. 0.5 h at 23° C.

Example 4. Survey of the N-Protecting Group

The effect of substituents on the N-aryl fragment of the lactam substrate was examined.

Several lactams (1a-d) were prepared and subjected to the optimized acylation conditions (Table 5). Lactam 1b displayed slightly superior enantioselectivity to 1a, although acylated product 4b was produced in moderate yield at ambient temperature. Gratifyingly, reaction at 0° C. led to improved yield of lactam 4b. Derivatives 1c and 1d had similar enantioselectivity as the parent PMP-lactam 1a. In general, a fair amount of substitution around the N-aryl group is tolerated in the reaction process affording acylated lactams in good yields and with high ee.

Conversion of allyl 1-methyl-2-oxocyclohexane-carboxylate (1a) in TBME resulted in a high yield and good enantioselectivity (Table 4, entry 1). When the reaction was performed in various alkyl acetates the yields dropped dramatically, to 12%, 28% and 17% respectively (Table 4, entries 2, 4 and 5). Similarly low yields were observed for reactions performed in acetonitrile, dimethylacetamide, 2-Me-THF, and acetone (Table 4, entries 3, 6, 8 and 10). Moderate conversion was found when the reaction was performed in toluene (Table 4, entry 7). Consequently, all further experiments were carried out in TBME.

TABLE 5

*Survey of the N-protecting group for the lactam acylation.*

TABLE 5-continued

| R yield, ee | | | | |
|---|---|---|---|---|
| | 1a→4a 86%, 88% ee[b] | 1b→4b 61%, 92% ee[b] 81%, 92% ee[c] | 1c→4c 80%, 95% ee[c] | 1d→4d 69%, 86% ee[c] |

[a]Conditions: lactam (2 equiv), PhCN (1 equiv), PhBr (1.5 equiv), LHMDS (1.2 equiv), LiBr (5 equiv), Ni(COD)₂ (10 mol %), ligand (12 mol %), in toluene-THF (10:1, 0.09M), then 1M HCl aq.
[b]Reactions were conducted at 23° C. for 24 h.
[c]Reactions were conducted at 0° C. for 48 h.

Example 5. Survey of the Substrate

The substrate scope of this enantioselective C-acylation reaction was explored (Tables 6 and 6). Generally, the process is tolerant of a wide range of substituents and functionality on both the aryl nitrile and the parent lactam substrate. Aryl nitriles having both electron-donating and electron-withdrawing substituents at the para position can be successfully applied, leading to products with excellent enantioselectivities (e.g., Table 6, 6, 9-12). Despite the uniformly high ee, electron-withdrawing substituents on the nitrile furnish products in significantly diminished yields (e.g., 11, 12). Lastly, the reaction is not impacted to a large degree when the nitrile is substituted at either the meta or ortho position (e.g., 7, 8).

TABLE 6

Assessment of the nitrile for the lactam acylation.

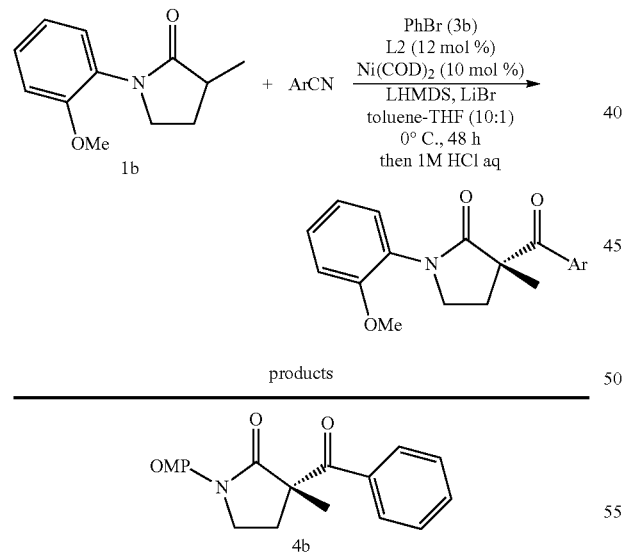

products

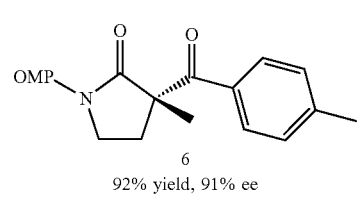

4b
81% yield, 92% ee

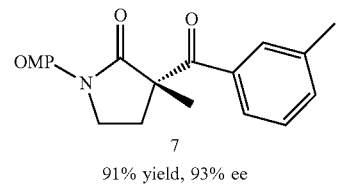

6
92% yield, 91% ee

TABLE 6-continued

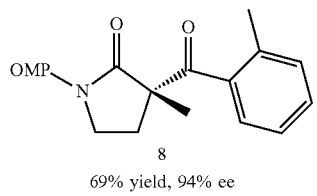

7
91% yield, 93% ee

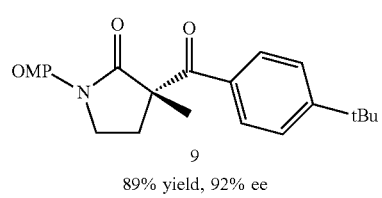

8
69% yield, 94% ee

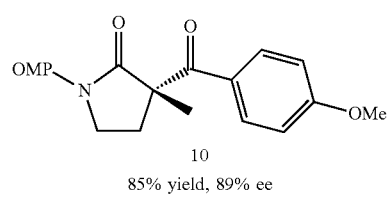

9
89% yield, 92% ee

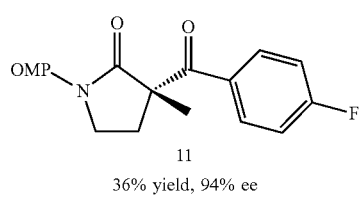

10
85% yield, 89% ee 11
36% yield, 94% ee

TABLE 6-continued

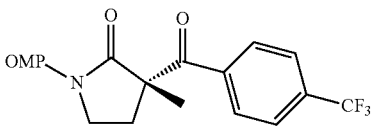

12
23% yield, 87% ee[b]

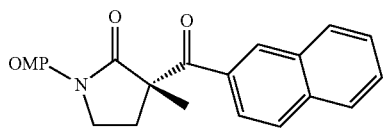

13
66% yield, 91% ee

[a]Conditions: lactam (2 equiv), ArCN (1 equiv), PhBr (1.5 equiv), base (1.2 equiv), Ni(COD)$_2$ (10 mol %), ligand (12 mol %), in toluene-THF (10:1, 0.09M) at 0° C. for 48 h, then 1M HCl aq.
[b]The reaction was carried out at 23° C. for 24 h.

The scope of substitution at the lactam α-carbon is illustrated in Table 7. Although the enantioselectivity tends to decrease with larger α-substituents, examples having ethyl, benzyl, substituted-benzyl and substituted-allyl groups all furnished the C-acylated products with good enantioselectivities (74-88% ee). Crotyl- and cinnamyl-substituted lactams were particularly effective in the acylation, providing interesting lactam products in high ee (e.g., 21-25).

TABLE 7

Assessment of the lactam α-substituent for the lactam acylation.

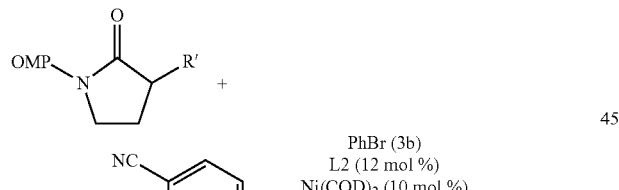

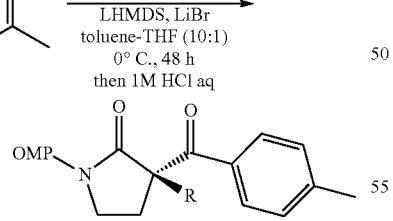

products[a]

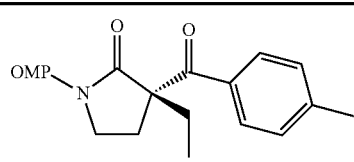

14
50% yield, 77% ee

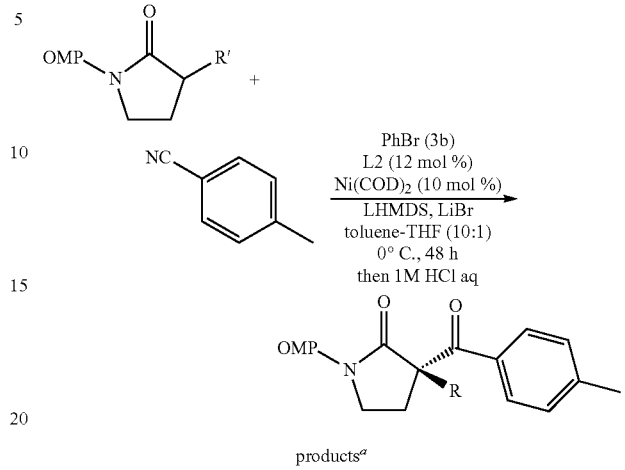

15 (R = H): 61% yield, 81% ee
16 (R = OMe): 77% yield, 81% ee
17 (R = F): 76% yield, 74% ee

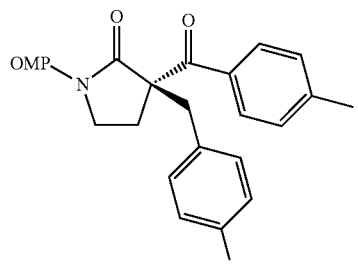

18
58% yield, 71% ee

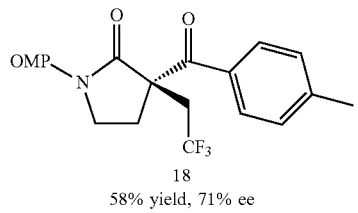

19
67% yield, 60% ee

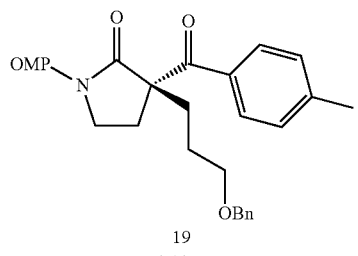

20
71% yield, 76% ee

TABLE 7-continued

Assessment of the lactam α-substituent for the lactam acylation.

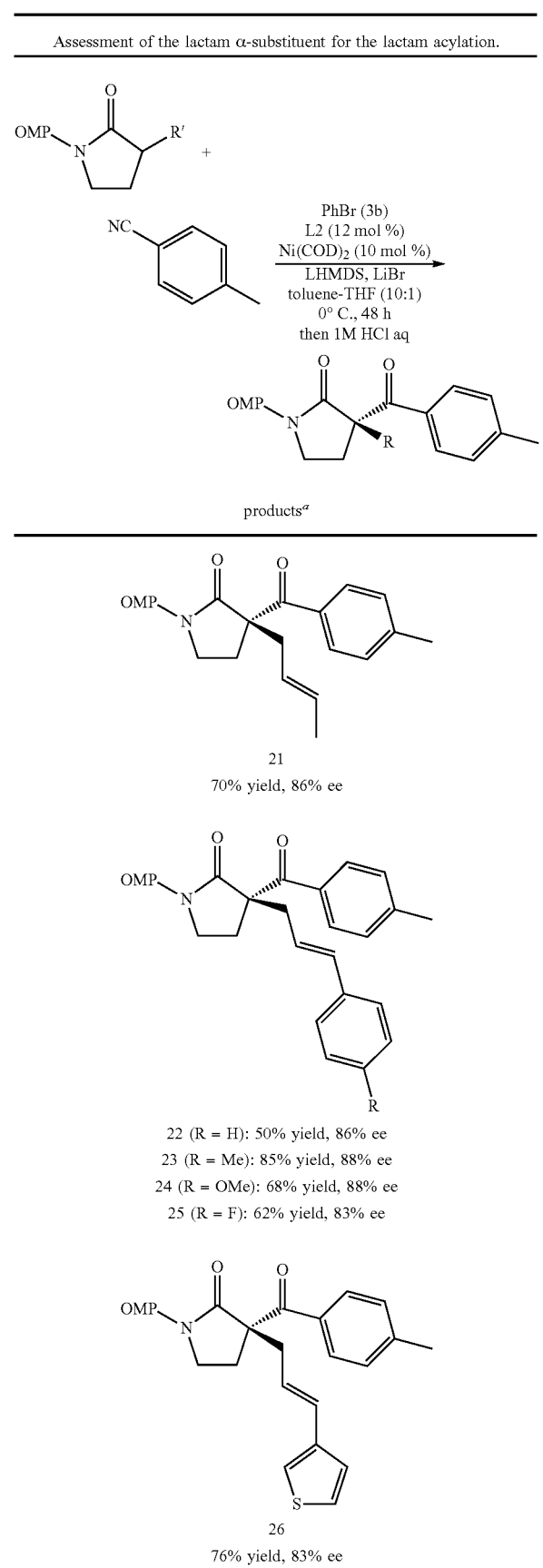

21
70% yield, 86% ee 22 (R = H): 50% yield, 86% ee
23 (R = Me): 85% yield, 88% ee
24 (R = OMe): 68% yield, 88% ee
25 (R = F): 62% yield, 83% ee 26
76% yield, 83% ee

TABLE 7-continued

Assessment of the lactam α-substituent for the lactam acylation.

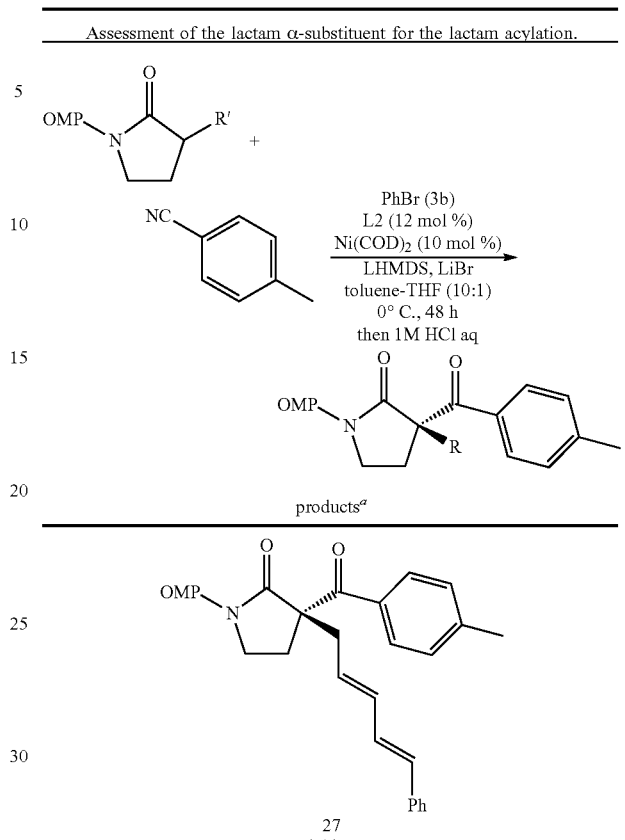

27
35% yield, 84% ee

The lactams 14-27 were prepared according to the general procedure A with lactam (2 equiv), p-tolunitrile (1 equiv), PhBr (1.5 equiv), base (1.2 equiv), Ni(COD)$_2$ (10 mol %), ligand (12 mol %), in toluene-THF (10:1, 0.09 M) at 0° C. for 48 h, then 1 M HCl aq.

Example 6. Derivatization of C-Acylated Products and Determination of Absolute Stereochemistry To demonstrate the synthetic utility of our enantioselective lactams acylation, transformations were carried out on the enantioenriched lactam products generated in this disclosure (Scheme 1). The o-methoxy protecting group of lactam 4e was easily removed by CAN oxidation to form lactam 28 (Scheme 1A).[11] Reduction of ketone 4e with Et$_3$SiH proceeded with perfect diastereoselectively and afforded alcohol 29 as a single isomer in excellent yield (Scheme 1B). The relative stereochemistry of lactam 29 was determined by single crystal X-ray diffraction (data not shown). Lactam 4a could be converted to α-benzoyloxy lactam 30 by Baeyer-Villiger oxidation, without loss of enantiopurity (Scheme 1C). Alternatively, Baeyer-Villiger oxidation of lactam 10 gave α-aryloxycarbonyl lactam 31 (Scheme 1D). The PMP ketone directs the regioselectivity of the Baeyer-Villiger oxidation and allows for the asymmetric synthesis of α-carboxy lactam derivatives.[12] To determine the absolute stereochemistry, 31 was converted to known lactam derivative 33 by ester exchange followed by deprotection of the o-methoxyphenyl group. The specific optical rotation of carboxylactam 33 corresponded to the reported value for (R)-33.[13] The absolute configurations of all acylated lactam products disclosed herein are presented by analogy to this finding.

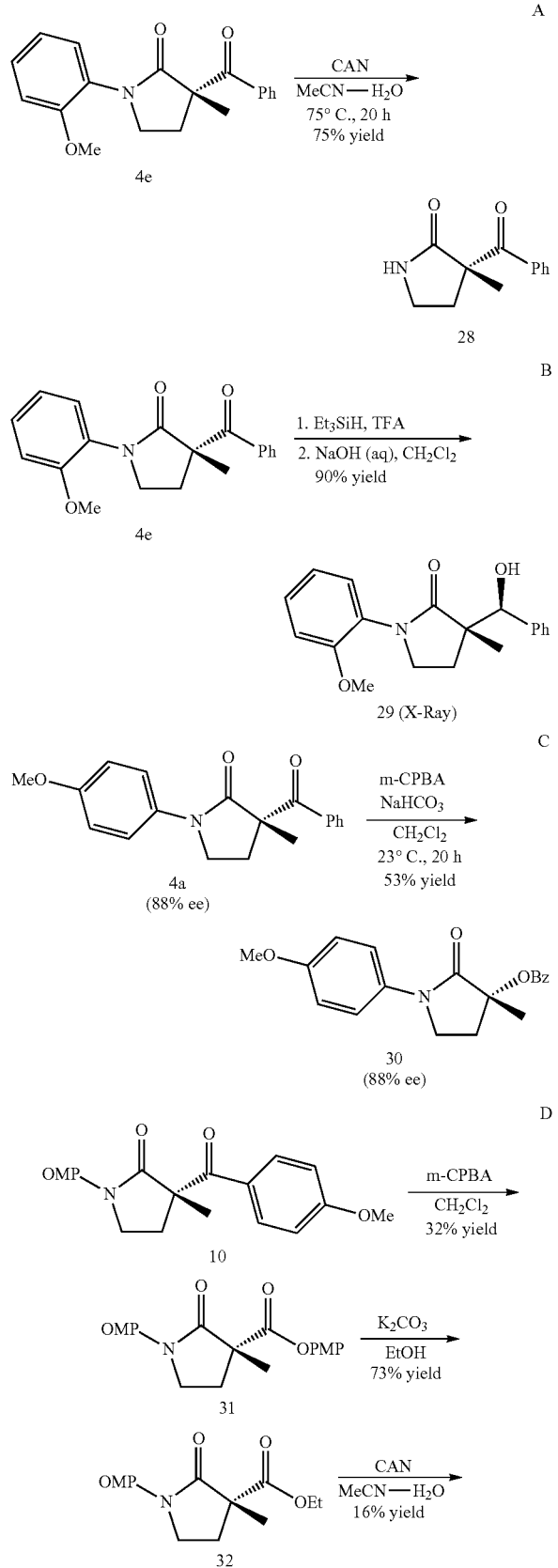

Scheme 1. Derivatization of C-acylated lactams.

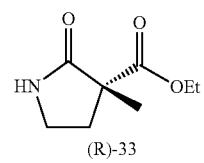

(R)-33

Example 6. Possible Reaction Mechanism of C-Acylation of Lactams

By avoiding an acidic aqueous work-up and carefully chromatographing of the crude reaction mixture, imine 34 was obtained as a 60:40 E/Z mixture from the reaction of lactam 1a with o-tolunitrile 2b and bromobenzene 3b (Scheme 2A). Additionally, amine 36 as a 63:37 diastereomeric mixture was prepared by in situ reduction of imine intermediate 35 (Scheme 2B). These experiments provide evidence that an N-arylated imine (e.g., 5a, 34, and 35) may be the direct product of the catalytic reaction.

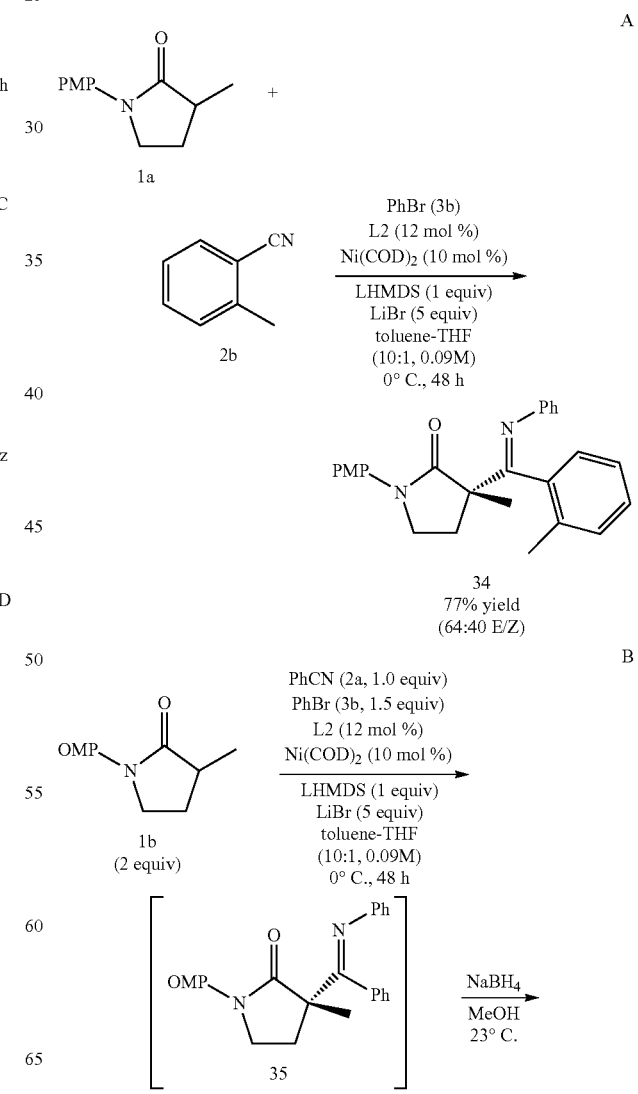

Scheme 2. Isolation and reduction of potential imine intermediate.

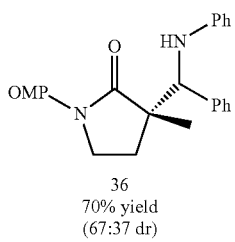

36
70% yield
(67:37 dr)

Figure 2:
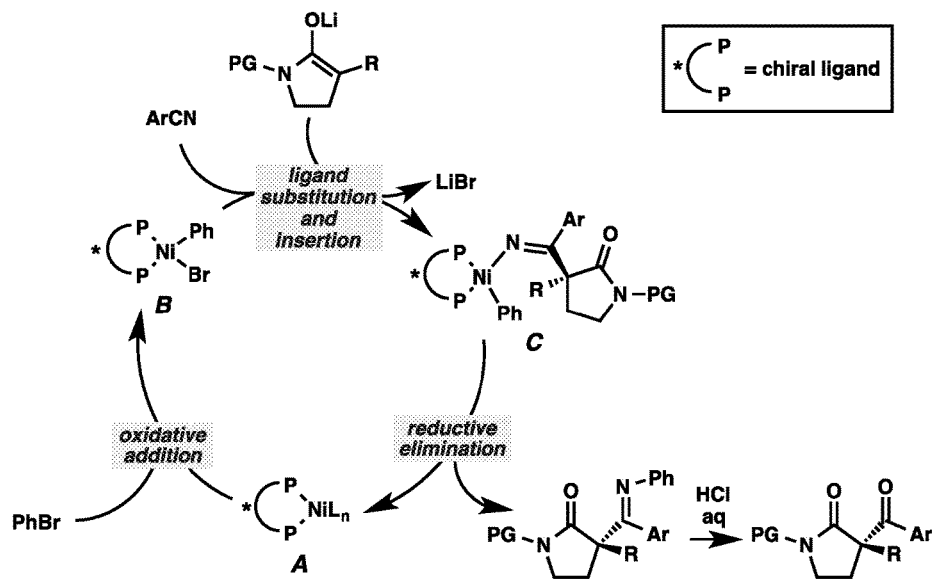
FIG. 2 shows a possible reaction mechanism of enantioselective C-acylation.

A possible reaction mechanism for the disclosed C-acylation reaction is shown in FIG. 2. Without being bound by theory, the reaction may proceed by a $Ni^0/Ni^{II}$ redox catalytic cycle. Oxidative addition of the aryl bromide to a $Ni^0$ complex (i.e., A) produces a $Ni^{II}$ arene species (B). Ligand substitution and insertion of the benzonitrile and lactam enolate is envisioned to be stereodetermining and to produce $Ni^{ee}$-imino complex C. Reductive elimination from C leads to the primary imine product and regenerates $Ni^0$ complex A. The C-acylated product is ultimately furnished by hydrolysis of the imine in aqueous acid.

Example 7. Experimental Procedures

General Procedure for α-Substituted Lactam Substrates

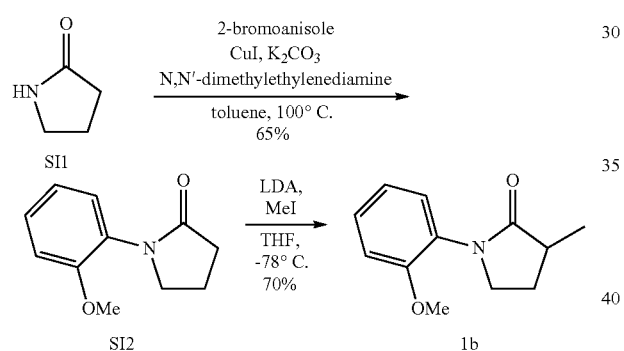

General Procedure
1: 1-(2-methoxyphenyl)pyrrolidin-2-one (SI2)

To a suspension of lactam SI1 (8.17 g, 96.0 mmol, 1.20 equiv), $K_2CO_3$ (22.1 g, 160 mmol, 2.00 equiv) and CuI (1.52 g, 8.00 mmol, 0.10 equiv) in toluene (80 mL) were added 2-bromoanisole (9.84 mL, 80.0 mmol, 1.00 equiv) and N,N'-dimethylethylendiamine (1.68 mL, 16.0 mmol, 0.20 equiv). The reaction mixture was stirred at 100° C. for 18 h then allowed to cool to ambient temperature and filtered through a pad of silica gel eluting with AcOEt (250 mL). The eluate was concentrated under reduced pressure and the residue was purified by flash column chromatography (1:1 EtOAc:hexanes) on silica gel to give lactam SI2 as a pale yellow oil (9.88 g, 65% yield). $^1$H NMR (500 MHz, CDCl$_3$) δ 7.35-7.26 (m, 2H), 7.06-6.97 (m, 2H), 3.88 (s, 3H), 3.80 (t, J=7.0 Hz, 2H), 2.60 (t, J=8.1 Hz, 2H), 2.23 (p, J=7.5 Hz, 2H); $^{13}$C NMR (126 MHz, CDCl$_3$) δ 175.2, 154.8, 128.7, 128.6, 127.2, 120.9, 112.0, 55.6, 49.9, 31.2, 19.0; IR (Neat Film NaCl) 2968, 2889, 2838, 1694, 1504, 1461, 1408, 1304, 1281, 1253, 1023, 755 cm$^{-1}$; HRMS (MM: ESI-APCI+) m/z calc'd for $C_{11}H_{14}NO_2$ [M+H]$^+$: 192.1019, found 192.1019.

General Procedure 2:
1-(2-methoxyphenyl)-3-methylpyrrolidin-2-one (1b)

To a solution of diisopropylamine (3.07 mL, 22.0 mmol, 1.10 equiv) in THF (17 mL) was added a solution of n-BuLi (8.80 mL, 22.0 mmol, 2.5 M in hexanes, 1.10 equiv) dropwise at −78° C. After 20 min at −78° C., a solution of lactam SI2 (3.82 g, 20.0 mmol, 1.00 equiv) in THF (50 mL) was added dropwise. After an additional 20 min, a solution of methyl iodide (15.0 mL, 30.0 mmol, 2.0 M in TBME, 1.50 equiv) was added and the reaction mixture was stirred at −78° C. for 3 h. Saturated NH$_4$Cl aqueous solution (50 mL) was added and the mixture was allowed to ambient temperature. The mixture was extracted with AcOEt (100 mL), washed with brine (30 mL), dried over Na$_2$SO$_4$, and concentrated under reduced pressure. The residue was purified by flash column chromatography (1:4 to 1:2 EtOAc: hexanes) on silica gel to give lactam 1b as a white solid (2.86 g, 70% yield). $^1$H NMR (500 MHz, CDCl$_3$) δ 7.34-7.26 (m, 3H), 7.06-6.96 (m, 2H), 3.87 (s, 3H), 3.79-3.66 (m, 2H), 2.69 (tq, J=8.7, 7.1 Hz, 1H), 2.41 (dddd, J=12.2, 8.5, 7.3, 3.5 Hz, 1H), 1.86 (dq, J=12.4, 8.5 Hz, 1H), 1.36 (d, J=7.1 Hz, 3H); $^{13}$C NMR (126 MHz, CDCl$_3$) δ 177.5, 154.8, 128.6, 128.5, 127.6, 120.8, 112.0, 55.6, 47.9, 36.9, 28.1, 16.3; IR (Neat Film NaCl) 2965, 2932, 2874, 1695, 1504, 1463, 1456, 1403, 1311, 1296, 1277, 1251, 1024, 754 cm$^{-1}$; HRMS (MM: ESI-APCI+) m/z calc'd for $C_{12}H_{16}NO_2$ [M+H]$^+$: 206.1176, found 206.1176.

N-Protected Lactams 1-(4-Methoxyphenyl)pyrrolidin-2-one (SI3)

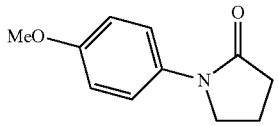

Lactam SI3 was prepared according to the general procedure 1, using 4-iodoanisole and $K_3PO_4$ in place of 2-bromoanisole and $K_2CO_3$ respectively, and isolated by recrystallization in hexanes/AcOEt (4/1) as a white crystal. 89% yield. $^1$H NMR (500 MHz, CDCl$_3$) δ 7.64-7.45 (m, 2H), 7.01-6.90 (m, 2H), 3.87 (t, J=7.0 Hz, 2H), 3.84 (s, 3H), 2.64 (t, J=8.1 Hz, 2H), 2.20 (tt, J=15.1, 7.5 Hz, 1H); $^{13}$C NMR (126 MHz, cdcl$_3$) δ 173.9, 156.5, 132.6, 121.8, 114.0, 55.5, 49.2, 32.5, 18.1; IR (Neat Film NaCl) 2952, 2907, 1683, 1517, 1255, 1226, 1182, 1126, 1032, 829 cm$^{-1}$; HRMS (MM: ESI-APCI+) m/z calc'd for $C_{11}H_{14}NO_2$ [M+H]$^+$: 192.1019, found 192.1021.

1-(3,5-Dimethoxyphenyl)pyrrolidin-2-one (SI4)

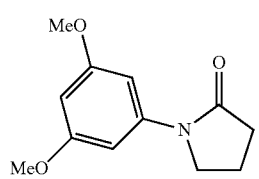

Lactam SI4 was prepared according to the general procedure 1, using 1-bromo-3,5-dimethoxybenzene in place of 2-bromoanisole, and isolated by recrystallization in hexanes/AcOEt (5/1) as a white crystal. 89% yield. $^1$H NMR (500 MHz, CDCl$_3$) δ 6.90 (d, J=2.2 Hz, 2H), 6.31 (t, J=2.2 Hz, 1H), 3.87 (t, J=7.0 Hz, 2H), 3.84 (s, 6H), 2.65 (t, J=8.1 Hz, 2H), 2.19 (p, J=7.5 Hz, 2H); $^{13}$C NMR (126 MHz, CDCl$_3$) δ 174.4, 160.8, 141.2, 98.4, 96.5, 77.3, 77.0, 76.8, 55.4, 49.0, 33.1, 17.9; IR (Neat Film NaCl) 2959, 1694, 1593, 1474, 1455, 1424, 1397, 1276, 1245, 1198, 1152, 1071, 1056, 922, 840, 825, 683 cm$^{-1}$; HRMS (MM: ESI-APCI+) m/z calc'd for C$_{12}$H$_{16}$NO$_3$ [M+H]$^+$: 222.1125, found 222.1129.

1-(2-Isopropoxyphenyl)-pyrrolidin-2-one (SI5)

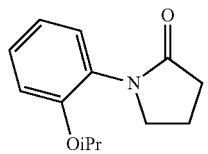

SI5

Lactam SI5 was prepared according to the general procedure 1, using 1-bromo-2-isopropoxybenzene in place of 2-bromoanisole, and isolated by flash column chromatography (1:2 to 1:1 EtOAc:hexanes) on silica gel as a pale yellow oil. 57% yield. $^1$H NMR (500 MHz, CDCl$_3$) δ 7.33-7.23 (m, 2H), 7.03-6.96 (m, 2H), 4.58 (hept, J=6.0 Hz, 1H), 3.82 (t, J=6.7 Hz, 2H), 2.59 (t, J=7.6 Hz, 2H), 2.28-2.16 (m, 2H), 1.38 (d, J=6.0 Hz, 6H); $^{13}$C NMR (126 MHz, CDCl$_3$) δ 175.2, 153.1, 128.9, 128.4, 128.4, 120.8, 114.7, 70.8, 49.9, 31.4, 22.2, 19.2; IR (Neat Film NaCl) 2976, 2933, 1697, 1595, 1500, 1456, 1405, 1385, 1304, 1282, 1251, 1125, 1111, 957, 753 cm$^{-1}$; HRMS (MM: ESI-APCI+) m/z calc'd for C$_{13}$H$_{18}$NO$_2$ [M+H]$^+$: 220.1332, found 220.1328.

α-Substituted Lactams 1-(4-Methoxyphenyl)-3-methylpyrrolidin-2-one (1a)

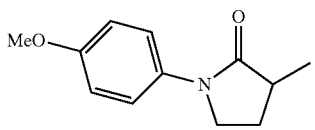

1a

Lactam 1a was prepared according to the general procedure 2 from SI3 in place of SI2, and isolated by flash column chromatography (1:3 EtOAc:hexanes) on silica gel as a white solid. 82% yield. $^1$H NMR (500 MHz, CDCl$_3$) δ 7.64-7.45 (m, 2H), 7.01-6.90 (m, 2H), 3.87 (t, J=7.0 Hz, 2H), 3.84 (s, 3H), 2.64 (t, J=8.1 Hz, 2H), 2.20 (tt, J=15.1, 7.5 Hz, 1H); $^{13}$C NMR (126 MHz, cdcl$_3$) δ 176.3, 156.4, 133.0, 121.4, 114.0, 55.5, 46.9, 38.1, 27.1, 16.3; IR (Neat Film NaCl) 2952, 2882, 2835, 1682, 1516, 1251, 1225, 1122, 1099, 1030, 829 cm$^{-1}$; HRMS (MM: ESI-APCI+) m/z calc'd for C$_{12}$H$_{16}$NO$_2$ [M+H]$^+$: 206.1176, found 206.1177.

1-(3,5-Dimethoxyphenyl)-3-methylpyrrolidin-2-one (1c)

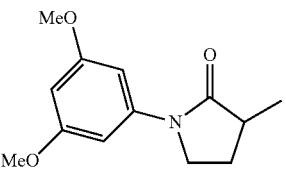

1c

Lactam 1c was prepared according to the general procedure 2 from SI4 in place of SI2, and isolated by flash column chromatography (1:4 EtOAc:hexanes) on silica gel as a white solid. 87% yield. $^1$H NMR (500 MHz, CDCl$_3$) δ 6.96 (d, J=2.2 Hz, 2H), 6.31 (t, J=2.2 Hz, 1H), 3.84 (s, 6H), 3.79 (dd, J=8.8, 5.0 Hz, 2H), 2.78-2.66 (m, 1H), 2.45-2.35 (m, 1H), 1.86-1.74 (m, 1H), 1.35 (d, J=7.1 Hz, 3H); $^{13}$C NMR (126 MHz, CDCl$_3$) δ 176.9, 160.8, 141.5, 97.9, 96.5, 77.3, 77.0, 76.8, 55.4, 46.8, 38.6, 26.9, 16.1; IR (Neat Film NaCl) 2964, 1698, 1597, 1474, 1392, 1273, 1246, 1208, 1154, 1071, 927, 834, 682 cm$^{-1}$; HRMS (MM: ESI-APCI+) m/z calc'd for C$_{13}$H$_{18}$NO$_3$ [M+H]$^+$: 236.1281, found 236.1284.

1-(2-Isoproxyphenyl)-3-methylpyrrolidin-2-one (1d)

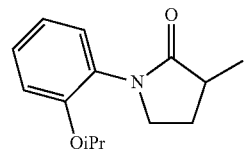

1d

Lactam 1d was prepared according to the general procedure 2 from SI5 in place of SI2, and isolated by flash column chromatography (1:3 to 1:2 EtOAc:hexanes) on silica gel as a pale yellow oil. 83% yield. $^1$H NMR (500 MHz, CDCl$_3$) δ 7.32-7.22 (m, 2H), 7.03-6.96 (m, 2H), 4.57 (hept, J=6.1 Hz, 1H), 3.80-3.67 (m, 2H), 2.67 (tq, J=8.4, 7.1 Hz, 1H), 2.46-2.35 (m, 1H), 1.84 (dq, J=12.3, 8.2 Hz, 1H), 1.37 (d, J=6.1 Hz, 6H), 1.35 (d, J=7.2 Hz, 3H); $^{13}$C NMR (126 MHz, CDCl$_3$) δ 177.5, 153.2, 129.0, 128.7, 128.3, 120.8, 114.8, 70.8, 47.9, 36.9, 28.2, 22.2, 22.2, 16.4; IR (Neat Film NaCl) 2974, 2930, 1701, 1595, 1499, 1457, 1405, 1277, 1249, 1124, 1111, 955, 750 cm$^{-1}$; HRMS (MM: ESI-APCI+) m/z calc'd for C$_{14}$H$_{20}$NO$_2$ [M+H]$^+$: 234.1489, found 234.1482.

1-(2-Methoxyphenyl)-3-ethypyrrolidin-2-one (SI6)

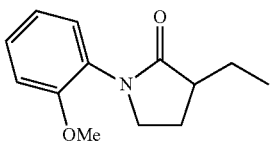

SI6

Lactam SI6 was prepared according to the general procedure 2 using ethyl iodide in place of methyl iodide, and isolated by flash column chromatography (1:3 EtOAc:

hexanes) on silica gel as a pale yellow oil. 81% yield. $^1$H NMR (500 MHz, CDCl$_3$) δ 7.29-7.19 (m, 2H), 7.01-6.92 (m, 2H), 3.82 (s, 3H), 3.76-3.69 (m, 1H), 3.69-3.60 (m, 1H), 2.53 (qd, J=8.7, 4.3 Hz, 1H), 2.38-2.27 (m, 1H), 2.04-1.92 (m, 1H), 1.92-1.81 (m, 1H), 1.63-1.49 (m, 1H), 1.04 (t, J=7.4 Hz, 3H); $^{13}$C NMR (126 MHz, CDCl$_3$) δ 176.9, 154.8, 128.7, 128.5, 127.5, 120.8, 112.0, 55.6, 48.2, 43.4, 25.1, 24.2, 11.5; IR (Neat Film NaCl) 2961, 1695, 1596, 1505, 1462, 1404, 1280, 1249, 1024, 752 cm$^{-1}$; HRMS (MM: ESI-APCI+) m/z calc'd for C$_{13}$H$_{18}$NO$_2$ [M+H]$^+$: 220.1332, found 220.1334.

3-Benzyl-1-(2-methoxyphenyl)pyrrolidin-2-one (SI7)

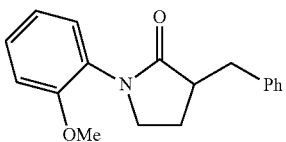

SI7

Lactam SI7 was prepared according to the general procedure 2 using benzyl bromide in place of methyl iodide, and isolated by flash column chromatography (1:5 EtOAc: hexanes) on silica gel as a pale yellow oil. 80% yield. $^1$H NMR (500 MHz, CDCl$_3$) δ 7.44-7.08 (m, 7H), 6.99-6.90 (m, 2H), 3.80 (s, 3H), 3.63 (dt, J=9.5, 7.7 Hz, 1H), 3.49 (ddd, J=9.5, 8.6, 3.7 Hz, 1H), 3.30 (dd, J=13.7, 4.0 Hz, 1H), 2.93-2.83 (m, 1H), 2.77 (dd, J=13.6, 9.7 Hz, 1H), 2.20-2.10 (m, 1H), 1.94-1.83 (m, 1H); $^{13}$C NMR (126 MHz, CDCl$_3$) δ 176.0, 154.8, 139.7, 129.1, 128.6, 128.5, 128.5, 128.4, 127.4, 126.3, 120.9, 112.0, 55.6, 48.0, 43.8, 37.0, 25.1; IR (Neat Film NaCl) 2942, 1694, 1596, 1504, 1454, 1407, 1279, 1252, 1025, 753, 701 cm$^{-1}$; HRMS (MM: ESI-APCI+) m/z calc'd for C$_{18}$H$_{20}$NO$_2$ [M+H]$^+$: 282.1489, found 282.1491.

3-(4-Methoxybenzyl)-1-(2-methoxyphenyl)pyrrolidin-2-one (SI8)

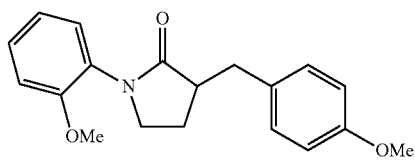

SI8

Lactam SI8 was prepared according to the general procedure 2 using 4-methoxybenzyl chloride in place of methyl iodide, and isolated by flash column chromatography (1:3 EtOAc:hexanes) on silica gel as a pale yellow oil. 59% yield. $^1$H NMR (500 MHz, CDCl$_3$) δ 7.29-7.24 (m, 1H), 7.24-7.14 (m, 3H), 7.00-6.90 (m, 2H), 6.88-6.80 (m, 2H), 3.79 (s, 3H), 3.78 (s, 3H), 3.62 (dt, J=9.5, 7.6 Hz, 1H), 3.47 (ddd, J=9.5, 8.6, 3.8 Hz, 1H), 3.21 (dd, J=13.7, 4.0 Hz, 1H), 2.90-2.80 (m, 1H), 2.74 (dd, J=13.8, 9.4 Hz, 1H), 2.20-2.09 (m, 1H), 1.93-1.81 (m, 1H); $^{13}$C NMR (126 MHz, CDCl$_3$) δ 176.1, 158.1, 154.8, 131.6, 130.1, 128.6, 128.5, 127.4, 120.8, 113.8, 112.1, 55.6, 55.3, 48.1, 43.9, 36.0, 25.0; IR (Neat Film NaCl) 2936, 1696, 1596, 1512, 11506, 1462, 1406, 1300, 1279, 1249, 1179, 1028, 753 cm$^{-1}$; HRMS (MM: ESI-APCI+) m/z calc'd for C$_{19}$H$_{22}$NO$_3$ [M+H]$^+$: 312.1594, found 312.1589.

3-(4-Fluorobenzyl)-1-(2-methoxyphenyl)pyrrolidin-2-one (SI9)

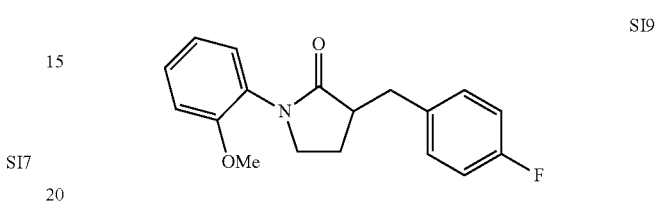

SI9

Lactam SI9 was prepared according to the general procedure 2 using 4-fluorobenzyl bromide in place of methyl iodide, and isolated by flash column chromatography (1:3 to 1:2 EtOAc:hexanes) on silica gel as a pale yellow oil. 77% yield. $^1$H NMR (500 MHz, CDCl$_3$) δ 7.31-7.18 (m, 4H), 7.04-6.92 (m, 4H), 3.81 (s, 3H), 3.65 (dt, J=9.6, 7.7 Hz, 1H), 3.50 (ddd, J=9.5, 8.6, 3.6 Hz, 1H), 3.24 (dd, J=13.5, 3.8 Hz, 1H), 2.93-2.76 (m, 2H), 2.22-2.12 (m, 1H), 1.94-1.82 (m, 1H); $^{13}$C NMR (126 MHz, CDCl$_3$) δ 175.7, 162.6, 160.6, 154.8, 135.2, 135.1, 130.6, 130.6, 128.6, 128.5, 127.3, 120.9, 115.3, 115.1, 112.0, 55.6, 48.0, 43.7, 36.1, 24.9; IR (Neat Film NaCl) 2942, 1696, 1597, 1507, 1459, 1406, 1252, 1221, 1158, 1025, 752 cm$^{-1}$; HRMS (MM: ESI-APCI+) m/z calc'd for C$_{18}$H$_{19}$FNO$_2$ [M+H]$^+$: 300.1394, found 300.1390.

1-(2-Methoxyphenyl)-3-(2,2,2-trifluoroethyl)pyrrolidin-2-one (SI10)

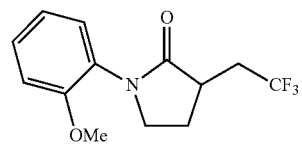

SI10

Lactam SI10 was prepared according to the general procedure 2 using 2-trifluoroethyl iodide in place of methyl iodide, and isolated by flash column chromatography (1:5 EtOAc:hexanes) on silica gel as a yellow oil. 36% yield. $^1$H NMR (500 MHz, CDCl$_3$) δ 7.29 (ddd, J=8.2, 7.5, 1.7 Hz, 1H), 7.23 (dd, J=7.7, 1.7 Hz, 1H), 7.03-6.93 (m, 2H), 3.83 (s, 3H), 3.80-3.72 (m, 1H), 3.65 (ddd, J=9.7, 8.8, 1.6 Hz, 1H), 3.04-2.93 (m, 1H), 2.93-2.84 (m, 1H), 2.56-2.46 (m, 1H), 2.14 (s, 1H), 2.07-1.95 (m, 1H); $^{13}$C NMR (126 MHz, CDCl$_3$) δ 173.8, 154.7, 128.9, 128.5, 128.1, 126.8, 125.9, 120.9, 112.0, 55.6, 48.0, 37.0, 36.9, 35.9, 35.7, 35.4, 35.2, 26.8; IR (Neat Film NaCl) 2946, 1703, 1597, 1505, 1462, 1414, 1282, 1252, 1135, 1039, 753, 615 cm$^{-1}$; HRMS (MM: ESI-APCI+) m/z calc'd for C$_{13}$H$_{15}$F$_3$NO$_2$ [M+H]$^+$: 274.1049, found 274.1049.

3-(3-(Benzyloxy)propyl)-1-(2-methoxyphenyl)pyrrolidin-2-one (SI11)

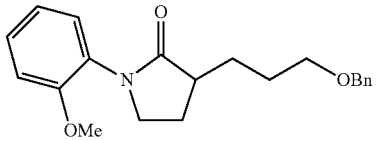

Lactam SI11 was prepared according to the general procedure 2 using ((3-bromopropoxy)methyl)benzene[14] in place of methyl iodide, and isolated by flash column chromatography (1:3 to 1:2 EtOAc:hexanes) on silica gel as a pale yellow oil. 76% yield. $^1$H NMR (500 MHz, CDCl$_3$) δ 7.36-7.18 (m, 7H), 6.99-6.90 (m, 2H), 4.50 (s, 2H), 3.80 (s, 3H), 3.73-3.64 (m, 1H), 3.64-3.58 (m, 1H), 3.58-3.46 (m, 2H), 2.63-2.53 (m, 1H), 2.36-2.25 (m, 1H), 2.05-1.94 (m, 1H), 1.90-1.80 (m, 1H), 1.80-1.68 (m, 2H), 1.64-1.52 (m, 1H); $^{13}$C NMR (126 MHz, CDCl$_3$) δ 176.7, 154.8, 138.6, 128.6, 128.5, 128.4, 127.7, 127.5, 127.4, 120.8, 112.0, 73.0, 70.4, 55.6, 48.2, 41.8, 28.0, 27.5, 25.8; IR (Neat Film NaCl) 2939, 2860, 1697, 1596, 1504, 1454, 1405, 1279, 1252, 1102, 1026, 749, 699 cm$^{-1}$; HRMS (MM: ESI-APCI+) m/z calc'd for C$_{21}$H$_{26}$NO$_3$ [M+H]$^+$: 340.1907, found 340.1915.

1-(2-Methoxyphenyl)-3-(3-methylbut-2-en-1-yl)pyrrolidin-2-one (SI12)

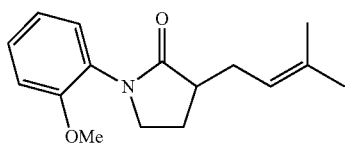

Lactam SI12 was prepared according to the general procedure 2 using 1-bromo-3-methyl-2-butene in place of methyl iodide, and isolated by flash column chromatography (1:3 EtOAc:hexanes) on silica gel as a pale yellow oil. 75% yield. $^1$H NMR (500 MHz, CDCl$_3$) δ 7.30-7.20 (m, 2H), 7.01-6.92 (m, 2H), 5.24-5.16 (m, 1H), 3.83 (s, 3H), 3.73-3.59 (m, 2H), 2.69-2.53 (m, 2H), 2.33-2.22 (m, 2H), 1.91-1.80 (m, 1H), 1.74 (s, 3H), 1.67 (s, 3H); $^{13}$C NMR (126 MHz, CDCl$_3$) δ 176.6, 154.8, 133.6, 128.6, 128.5, 127.6, 121.3, 120.8, 112.0, 55.6, 55.6, 48.2, 42.3, 29.5, 25.9, 25.9, 25.1, 18.0; IR (Neat Film NaCl) 2913, 1698, 1596, 1505, 1459, 1405, 1279, 1252, 1025, 751 cm$^{-1}$; HRMS (MM: ESI-APCI+) m/z calc'd for C$_{16}$H$_{22}$NO$_2$ [M+H]$^+$: 260.1645, found 260.1644.

(E)-3-(But-2-en-1-yl)-1-(2-methoxyphenyl)pyrrolidin-2-one (SI13)

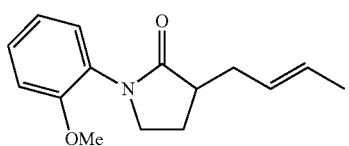

Lactam SI13 was prepared according to the general procedure 2 using 1-bromo-2-butene[15] in place of methyl iodide, and isolated by flash column chromatography (1:5 EtOAc:hexanes) on silica gel as a pale yellow oil. 24% yield. $^1$H NMR (500 MHz, CDCl$_3$) δ 7.30-7.21 (m, 2H), 7.01-6.92 (m, 2H), 5.62-5.43 (m, 2H), 3.83 (s, 3H), 3.73-3.58 (m, 2H), 2.68-2.53 (m, 2H), 2.32-2.19 (m, 2H), 1.95-1.82 (m, 1H), 1.72-1.66 (m, 3H); $^{13}$C NMR (126 MHz, CDCl$_3$) δ 176.5, 154.8, 128.6, 128.6, 128.6, 128.1, 127.4, 120.9, 112.1, 55.6, 48.2, 42.0, 34.3, 24.8, 18.1; IR (Neat Film NaCl) 2937, 1699, 1596, 1505, 1456, 1436, 1404, 1298, 1279, 1252, 1107, 1046, 1025, 968, 751 cm$^{-1}$; HRMS (MM: ESI-APCI+) m/z calc'd for C$_{15}$H$_{20}$NO$_2$ [M+H]$^+$: 246.1489, found 246.1487.

(E)-3-Cinnamyl-1-(2-methoxyphenyl)pyrrolidin-2-one (SI14)

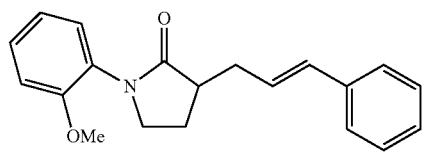

Lactam SI14 was prepared according to the general procedure 2 using cinnamyl bromide in place of methyl iodide, and isolated by flash column chromatography (1:5 to 1:2 EtOAc:hexanes) on silica gel as a pale yellow oil. 80% yield. $^1$H NMR (500 MHz, CDCl$_3$) δ 7.41-7.36 (m, 2H), 7.36-7.17 (m, 5H), 7.02-6.93 (m, 2H), 6.51 (d, J=15.7 Hz, 1H), 6.29 (dt, J=15.7, 7.1 Hz, 1H), 3.81 (s, 3H), 3.75-3.61 (m, 2H), 2.84-2.73 (m, 2H), 2.57-2.46 (m, 1H), 2.38-2.27 (m, 1H), 2.03-1.92 (m, 1H); $^{13}$C NMR (126 MHz, CDCl$_3$) δ 176.0, 154.8, 137.5, 132.2, 128.6, 128.6, 128.5, 127.5, 127.4, 127.1, 126.1, 120.9, 112.0, 55.6, 48.2, 41.9, 34.7, 24.8; IR (Neat Film NaCl) 2941, 1694, 1596, 1504, 1463, 1407, 1253, 1025, 967, 749, 694 cm$^{-1}$; HRMS (MM: ESI-APCI+) m/z calc'd for C$_{20}$H$_{22}$NO$_2$ [M+H]$^+$: 308.1645, found 308.1645.

(E)-1-(2-Methoxyphenyl)-3-(3-(p-tolyl)allyl)pyrrolidin-2-one (SI15)

Lactam SI15 was prepared according to the general procedure 2 using (E)-1-(3-chloroprop-1-en-1-yl)-4-methylbenzene[16] in place of methyl iodide, and isolated by flash column chromatography (1:3 EtOAc:hexanes) on silica gel as a pale yellow oil. 90% yield. $^1$H NMR (500 MHz, CDCl$_3$) δ 7.34-7.21 (m, 4H), 7.13 (d, J=7.9 Hz, 2H), 7.03-6.94 (m, 2H), 6.49 (d, J=15.7 Hz, 1H), 6.24 (dt, J=15.8, 7.1 Hz, 1H), 3.83 (s, 3H), 3.77-3.62 (m, 2H), 2.84-2.73 (m, 2H), 2.58-2.44 (m, 1H), 2.40-2.27 (m, 4H), 2.04-1.92 (m, 1H); $^{13}$C NMR (126 MHz, CDCl$_3$) δ 176.1, 154.8, 136.9, 134.7, 132.0, 129.2, 128.6, 128.6, 127.4, 126.4, 126.0, 120.9, 112.0, 55.6, 48.2, 41.9, 34.7, 24.8, 21.2; IR (Neat Film NaCl) 2939, 1695, 1596, 1504, 1462, 1405, 1279, 1252, 1181, 1122, 1107, 1045, 1025, 968, 891, 752 cm$^{-1}$; HRMS (MM: ESI-APCI+) m/z calc'd for $C_{21}H_{24}NO_2$ [M+H]$^+$: 322.1802, found 322.1803.

(E)-1-(2-Methoxyphenyl)-3-(3-(4-methoxyphenyl)allyl)pyrrolidin-2-one (SI16)

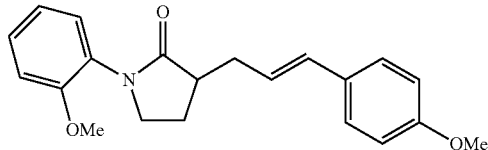

SI16

Lactam SI16 was prepared according to the general procedure 2 using (E)-1-(3-chloroprop-1-en-1-yl)-4-methoxybenzene[17] in place of methyl iodide, and isolated by flash column chromatography (1:3 EtOAc:hexanes) on silica gel as a pale yellow oil. 100% yield. $^1$H NMR (500 MHz, CDCl$_3$) δ 7.42-7.18 (m, 4H), 7.02-6.94 (m, 2H), 6.94-6.82 (m, 2H), 6.45 (dt, J=15.8, 1.4 Hz, 1H), 6.14 (dt, J=15.7, 7.1 Hz, 1H), 3.81 (s, 3H), 3.81 (s, 3H), 3.76-3.60 (m, 2H), 2.81-2.69 (m, 2H), 2.54-2.43 (m, 1H), 2.37-2.26 (m, 1H), 2.02-1.91 (m, 1H); $^{13}$C NMR (126 MHz, CDCl$_3$) δ 176.1, 158.9, 154.8, 131.5, 130.3, 128.6, 128.6, 127.4, 127.2, 125.2, 120.9, 113.9, 112.0, 55.6, 55.3, 48.2, 42.0, 34.7, 24.8; IR (Neat Film NaCl) 2934, 1694, 1606, 1510, 1505, 1463, 1406, 1249, 1175, 1027, 753 cm$^{-1}$; HRMS (MM: ESI-APCI+) m/z calc'd for $C_{21}H_{24}NO_3$ [M+H]$^+$: 338.1751, found 338.1748.

(E)-3-(3-(4-Fluorophenyl)allyl)-1-(2-methoxyphenyl)pyrrolidin-2-one (SI17)

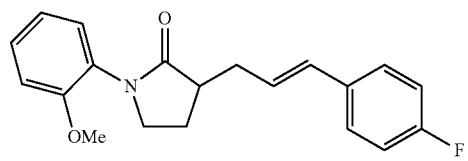

SI17

Lactam SI17 was prepared according to the general procedure 2 using (E)-1-(3-chloroprop-1-en-1-yl)-4-fluorobenzene[18] in place of methyl iodide, and isolated by flash column chromatography (1:3 EtOAc:hexanes) on silica gel as a white solid. 52% yield. $^1$H NMR (500 MHz, CDCl$_3$) δ 7.37-7.30 (m, 2H), 7.30-7.21 (m, 2H), 7.05-6.93 (m, 4H), 6.51-6.43 (m, 1H), 6.20 (dt, J=15.8, 7.1 Hz, 1H), 3.81 (s, 3H), 3.75-3.61 (m, 2H), 2.83-2.73 (m, 2H), 2.56-2.45 (m, 1H), 2.38-2.27 (m, 1H), 1.96 (ddt, J=12.8, 8.6, 7.6 Hz, 1H); $^{13}$C NMR (126 MHz, CDCl$_3$) δ 176.1, 163.0, 161.1, 154.8, 133.7, 133.6, 131.0, 128.7, 128.6, 127.6, 127.5, 127.3, 127.8, 127.2, 120.9, 115.5, 115.3, 112.0, 55.6, 48.2, 41.9, 34.7, 24.9; IR (Neat Film NaCl) 2942, 1696, 1597, 1507, 1458, 1405, 1279, 1253, 1225, 1158, 1046, 1025, 968, 839, 753 cm$^{-1}$; HRMS (MM: ESI-APCI+) m/z calc'd for $C_{20}H_{21}FNO_2$ [M+H]$^+$: 326.1551, found 326.1544.

(E)-1-(2-Methoxyphenyl)-3-(3-(thiophen-3-yl)ally)pyrrolidin-2-one (SI18)

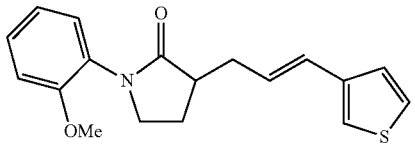

SI18

Lactam SI18 was prepared according to the general procedure 2 using (E)-3-(3-chloroprop-1-en-1-yl)thiophene in place of methyl iodide, and isolated by flash column chromatography (1:2 EtOAc:hexanes) on silica gel as a pale yellow oil. 62% yield. $^1$H NMR (500 MHz, CDCl$_3$) δ 7.31-7.19 (m, 4H), 7.10 (dd, J=3.1, 1.2 Hz, 1H), 7.01-6.92 (m, 2H), 6.52 (d, J=15.7 Hz, 1H), 6.13 (dt, J=15.7, 7.1 Hz, 1H), 3.81 (s, 3H), 3.75-3.59 (m, 2H), 2.81-2.71 (m, 2H), 2.53-2.42 (m, 1H), 2.37-2.26 (m, 1H), 2.02-1.90 (m, 1H); $^{13}$C NMR (126 MHz, CDCl$_3$) δ 176.1, 154.8, 140.1, 128.6, 128.6, 127.3, 127.3, 126.4, 125.9, 125.0, 121.0, 120.9, 112.1, 55.6, 48.2, 41.9, 34.6, 24.9; IR (Neat Film NaCl) 2936, 1694, 1596, 1504, 1463, 1408, 1279, 1252, 1181, 1122, 1046, 1025, 966, 890, 862, 753 cm$^{-1}$; HRMS (MM: ESI-APCI+) m/z calc'd for $C_{18}H_{20}NO_2S$ [M+H]$^+$: 314.1209, found 314.1206.

1-(2-Methoxyphenyl)-3-((2E,4E)-5-phenylpenta-2,4-dien-1-yl)pyrrolidin-2-one (SI19)

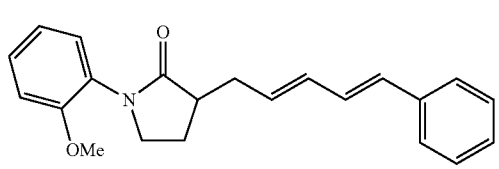

SI19

Lactam SI19 was prepared according to the general procedure 2 using (((1E,3E)-5-bromopenta-1,3-dien-1-yl)benzene[20] in place of methyl iodide, and isolated by flash column chromatography (1:2 EtOAc:hexanes) on silica gel as a colorless oil. 73% yield. $^1$H NMR (500 MHz, CDCl$_3$) δ 7.42-7.36 (m, 2H), 7.36-7.17 (m, 4H), 7.02-6.92 (m, 2H), 6.79 (ddd, J=15.7, 10.4, 0.8 Hz, 1H), 6.49 (d, J=15.7 Hz, 1H), 6.33 (ddd, J=15.1, 10.4, 0.8 Hz, 1H), 5.93-5.83 (m, 1H), 3.83 (s, 3H), 3.76-3.61 (m, 2H), 2.80-2.68 (m, 2H), 2.47-2.37 (m, 1H), 2.36-2.26 (m, 1H), 1.99-1.87 (m, 1H); $^{13}$C NMR (126 MHz, CDCl$_3$) δ 176.0, 154.8, 137.4, 132.8, 132.0, 130.9, 129.0, 128.6, 128.6, 128.6, 127.4, 127.3, 126.2, 120.9, 112.0, 55.6, 48.1, 41.9, 34.6, 25.0; IR (Neat Film NaCl) 2941, 1694, 1596, 1505, 1463, 1407, 1300, 1279, 1252, 1181, 1123, 1107, 1046, 1026, 992, 911, 891, 750, 693 cm$^{-1}$; HRMS (MM: ESI-APCI+) m/z calc'd for $C_{22}H_{24}NO_2$ [M+H]$^+$: 334.1802, found 334.1801.

General Procedure for Ni-Catalyzed C-Acylation

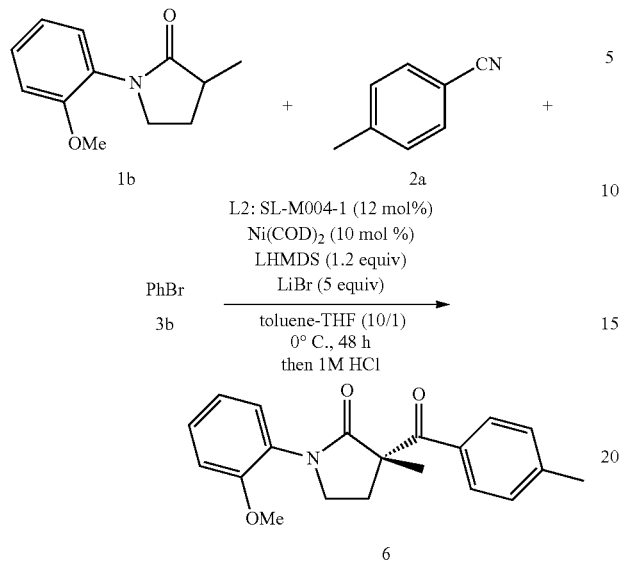

General Procedure 3: (S)-1-(2-methoxyphenyl)-3-methyl-3-(4-methylbenzoyl) pyrrolidin-2-one (6)

To a suspension of lactam 1b (82.1 mg, 0.400 mmol, 2.00 equiv), p-tolunitrile 2a (23.4 mg, 0.200 mmol, 1.00 equiv), bromobenzene 3b (31.5 μL, 0.300 mmol, 1.50 equiv), LHMDS (40.2 mg, 0.240 mmol, 1.20 equiv) and LiBr (86.9 mg, 1.00 mmol, 5.00 equiv) in toluene (1.0 mL) and THF (0.20 mL) was added a solution of Ni(COD)$_2$ (5.50 mg, 0.0200 mmol, 0.100 equiv) and SL-M004-1 (Solvias, 25.3 mg, 0.0240 mmol, 0.120 equiv) at 0° C. and the reaction mixture was stirred at 0° C. for 48 h. AcOEt (6 mL) and 1 M HCl aqueous solution (5 mL) were added and the mixture was stirred at ambient temperature for 1 h. The reaction mixture was extracted with AcOEt (24 mL), washed with brine (5 mL), dried over Na$_2$SO$_4$, and concentrated under reduced pressure. The residue was purified by flash column chromatography (1:5 EtOAc:hexanes) on silica gel to give lactam 6 as a white solid (59.4 mg, 92% yield, 91% ee). $[\alpha]_D^{25}$ +2.1° (c 1.03, CHCl$_3$); $^1$H NMR (500 MHz, CDCl$_3$) δ 8.09-8.02 (m, 2H), 7.33-7.20 (m, 4H), 7.03-6.95 (m, 2H), 3.94-3.87 (m, 1H), 3.85 (s, 3H), 3.84-3.78 (m, 1H), 2.94 (ddd, J=12.9, 8.4, 6.4 Hz, 1H), 2.40 (s, 3H), 2.07 (ddd, J=12.8, 8.0, 4.8 Hz, 1H), 1.68 (s, 3H); $^{13}$C NMR (126 MHz, CDCl$_3$) δ 198.4, 174.9, 155.0, 143.2, 133.0, 129.6, 129.0, 129.0, 128.4, 126.9, 120.9, 112.1, 56.6, 55.7, 47.1, 32.5, 21.6; IR (Neat Film NaCl) 2973, 2929, 1701, 1696, 1606, 1503, 1459, 1408, 1272, 1255, 1185, 1121, 1023, 1009, 970, 753 cm$^{-1}$; HRMS (MM: ESI-APCI+) m/z calc'd for C$_{20}$H$_{22}$NO$_3$ [M+H]$^+$: 324.1594, found 324.1599.

Ni-Catalyzed C-Acylation Products

(S)-3-Benzoyl-1-(4-methoxyphenyl)-3-methylpyrrolidin-2-one (4a)

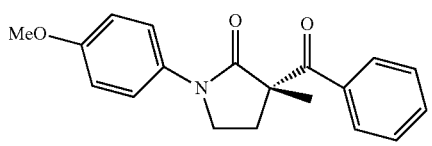

Lactam 4a was prepared according to the general procedure 3 from 1a using benzonitrile in place of p-tolunitrile, reacting at ambient temperature for 24 h in place of 0° C. for 48 h, and isolated by flash column chromatography (1:10 EtOAc:hexanes) on silica gel as a white solid. 86% yield, 88% ee. $[\alpha]_D^{25}$ −27.1° (c 1.45, CHCl$_3$); $^1$H NMR (500 MHz, CDCl$_3$) δ 8.07-8.00 (m, 2H), 7.58-7.47 (m, 3H), 7.46-7.38 (m, 2H), 6.96-6.87 (m, 2H), 3.95 (ddd, J=9.5, 7.9, 6.1 Hz, 1H), 3.86 (ddd, J=9.6, 8.2, 5.1 Hz, 1H), 3.82 (s, 3H), 2.93 (ddd, J=13.0, 8.0, 5.1 Hz, 1H), 2.08 (ddd, J=12.9, 8.3, 6.1 Hz, 1H), 1.68 (s, 3H); $^{13}$C NMR (126 MHz, CDCl$_3$) δ 2930, 199.0, 173.2, 156.9, 135.9, 132.5, 132.4, 129.2, 128.4, 121.8, 114.1, 58.3, 55.5, 46.5, 31.7, 22.0; IR (Neat Film NaCl) 1685, 1512, 1399, 1268, 1249, 1182, 1090, 1032, 970, 830, 702 cm$^{-1}$; HRMS (MM: ESI-APCI+) m/z calc'd for C$_{19}$H$_{20}$NO$_3$ [M+H]$^+$: 310.1438, found 310.1442.

(S)-3-Benzoyl-1-(2-methoxyphenyl)-3-methylpyrrolidin-2-one (4b)

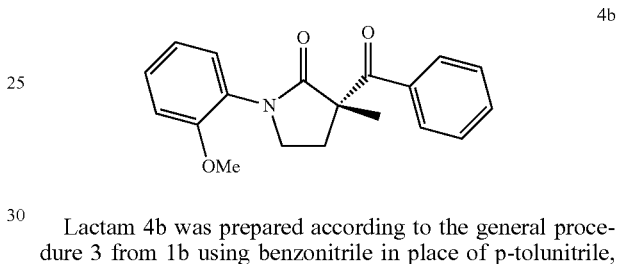

Lactam 4b was prepared according to the general procedure 3 from 1b using benzonitrile in place of p-tolunitrile, and isolated by flash column chromatography (1:5 EtOAc:hexanes) on silica gel as a white solid. 81% yield, 92% ee. $[\alpha]_D^{25}$ +4.0° (c 1.21, CHCl$_3$, 92% ee); $^1$H NMR (500 MHz, CDCl$_3$) δ 8.17-8.11 (m, 2H), 7.56-7.48 (m, 1H), 7.47-7.40 (m, 2H), 7.34-7.25 (m, 2H), 7.04-6.95 (m, 2H), 3.90 (ddd, J=9.6, 8.4, 4.8 Hz, 1H), 3.86-3.78 (m, 1H), 3.85 (s, 3H), 2.95 (ddd, J=12.9, 8.4, 6.3 Hz, 1H), 2.08 (ddd, J=12.8, 8.0, 4.8 Hz, 1H), 1.69 (s, 3H); $^{13}$C NMR (126 MHz, CDCl$_3$) δ 1989.0, 174.7, 155.0, 135.8, 132.4, 129.4, 129.0, 128.3, 128.3, 126.8, 121.0, 112.1, 56.8, 55.7, 47.1, 32.4, 21.6; IR (Neat Film NaCl) 2974, 2930, 1701, 1697, 1596, 1503, 1459, 1410, 1305, 1270, 1256, 1121, 1023, 1010, 970, 750, 702 cm$^{-1}$; HRMS (MM: ESI-APCI+) m/z calc'd for C$_{19}$H$_{20}$NO$_3$ [M+]$^+$: 310.1438, found 310.1441.

(S)-3-Benzoyl-1-(3,5-dimethoxyphenyl)-3-methylpyrrolidin-2-one (4c)

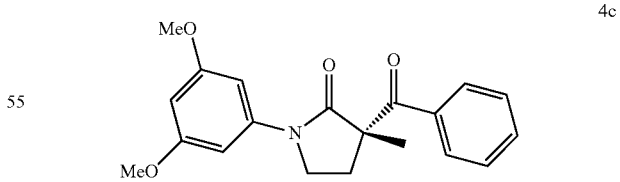

Lactam 4c was prepared according to the general procedure 3 from 1c using benzonitrile in place of p-tolunitrile, and isolated by flash column chromatography (1:5 EtOAc:hexanes) on silica gel as a white solid. 80% yield, 85% ee. $[\alpha]_D^{25}$ −30.0° (c 1.04, CHCl$_3$); $^1$H NMR (500 MHz, CDCl$_3$) δ 8.04-7.97 (m, 2H), 7.55-7.48 (m, 1H), 7.47-7.38 (m, 2H), 6.92 (d, J=2.2 Hz, 2H), 6.31 (t, J=2.2 Hz, 1H), 3.97 (ddd, J=9.6, 8.0, 6.0 Hz, 1H), 3.87 (ddd, J=9.6, 8.3, 5.1 Hz, 1H), 3.81 (s, 6H), 2.92 (ddd, J=13.1, 8.0, 5.2 Hz, 1H), 2.07 (ddd, J=12.9, 8.3, 6.0 Hz, 1H), 1.68 (s, 3H); $^{13}$C NMR (126 MHz, CDCl$_3$) δ 198.6, 173.8, 160.9, 141.0, 135.7, 132.6, 129.2, 128.4, 98.3, 97.1, 58.7, 55.5, 46.4, 31.4, 22.0; IR (Neat Film NaCl) 2937, 2840, 1696, 1598, 1480, 1393, 1277, 1249, 1206, 1156, 1067, 972, 834, 722, 699, 682, 661 cm$^{-1}$; HRMS (MM: ESI-APCI+) m/z calc'd for C$_{20}$H$_{22}$NO$_4$ [M+H]$^+$: 340.1543, found 340.1552.

(S)-3-Benzoyl-1-(2-isopropoxyphenyl)-3-methylpyrrolidin-2-one (4d)

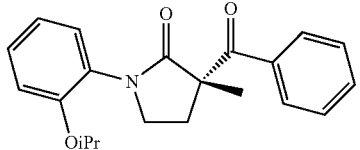

4d

Lactam 4d was prepared according to the general procedure 3 from 1d using benzonitrile in place of p-tolunitrile, and isolated by flash column chromatography (1:5 EtOAc:hexanes) on silica gel as a white solid. 69% yield, 86% ee. [α]$_D^{25}$ +9.4° (c 1.01, CHCl$_3$); $^1$HNMR (500 MHz, CDCl$_3$) δ 8.21-8.14 (m, 2H), 7.59-7.51 (m, 1H), 7.51-7.43 (m, 2H), 7.35-7.26 (m, 2H), 7.06-6.97 (m, 2H), 4.63 (hept, J=6.1 Hz, 1H), 3.98 (ddd, J=9.5, 8.2, 4.9 Hz, 1H), 3.85 (ddd, J=9.6, 8.0, 6.3 Hz, 1H), 3.00 (ddd, J=12.8, 8.2, 6.3 Hz, 1H), 2.10 (ddd, J=12.8, 8.0, 4.9 Hz, 1H), 1.73 (s, 3H), 1.36 (d, J=6.0 Hz, 3H), 1.35 (d, J=6.0 Hz, 3H); $^{13}$C NMR (126 MHz, CDCl$_3$) δ 199.0, 174.5, 153.2, 135.9, 132.4, 129.4, 128.8, 128.8, 128.3, 127.7, 120.6, 114.1, 70.4, 56.9, 47.2, 32.6, 22.1, 22.1, 21.6; IR (Neat Film NaCl) 2977, 2930, 1697, 1596, 1500, 1455, 1407, 1281, 1270, 1255, 1124, 954, 750, 701 cm$^{-1}$; HRMS (MM: ESI-APCI+) m/z calc'd for C$_{21}$H$_{24}$NO$_3$ [M+H]$^+$: 338.1751, found 338.1744.

(S)-1-(2-Methoxyphenyl)-3-methyl-3-(3-methylbenzoyl)pyrrolidin-2-one (7)

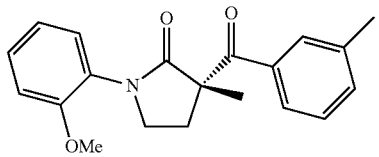

7

Lactam 7 was prepared according to the general procedure 3 from 1b using m-tolunitrile in place of p-tolunitrile, and isolated by flash column chromatography (1:5 EtOAc:hexanes) on silica gel as a colorless oil. 91% yield, 93% ee. [α]$_D^{25}$ +5.5° (c 0.52, CHCl$_3$); $^1$H NMR (500 MHz, CDCl$_3$) δ 7.97-7.90 (m, 1H), 7.89-7.88 (m, 1H), 7.33-7.26 (m, 4H), 7.04-6.95 (m, 2H), 3.90 (ddd, J=9.6, 8.4, 4.7 Hz, 1H), 3.86-3.78 (m, 1H), 3.84 (s, 3H), 2.93 (ddd, J=12.9, 8.4, 6.5 Hz, 1H), 2.40 (s, 3H), 2.11-2.02 (m, 1H), 1.67 (s, 3H); $^{13}$C NMR (126 MHz, CDCl$_3$) δ 199.3, 174.8, 155.06, 138.0, 135.8, 133.1, 129.8, 129.0, 128.3, 128.1, 126.9, 126.5, 121.0, 112.1, 56.8, 55.7, 47.1, 32.4, 21.6, 21.5; IR (Neat Film NaCl) 2973, 2931, 1694, 1598, 1504, 1455, 1409, 1276, 1255, 1182, 1121, 1092, 1044, 1024, 976, 905, 789, 754, cm$^{-1}$; HRMS (MM: ESI-APCI+) m/z calc'd for C$_{20}$H$_{22}$NO$_3$ [M+H]$^+$: 324.1594, found 324.1602.

(S)-1-(2-Methoxyphenyl)-3-methyl-3-(2-methylbenzoyl)pyrrolidin-2-one (8)

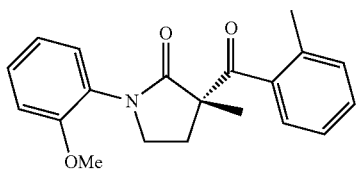

8

Lactam 8 was prepared according to the general procedure 3 from 1b using o-tolunitrile in place of p-tolunitrile, reacting with aqueous HCl at 70° C. in place of ambient temperature, and isolated by flash column chromatography (1:5 EtOAc:hexanes) on silica gel as a colorless oil. 69% yield, 94% ee. [α]$_D^{25}$ 29.6° (c 0.20, CHCl$_3$); $^1$H NMR (500 MHz, CDCl$_3$) δ 7.64 (dd, J=7.6, 1.4 Hz, 1H), 7.34-7.25 (m, 2H), 7.25-7.16 (m, 3H), 7.01-6.93 (m, 2H), 3.82 (s, 3H), 3.73 (dd, J=7.6, 6.3 Hz, 2H), 2.82-2.73 (m, 1H), 2.33 (s, 3H), 2.14-2.05 (m, 1H), 1.59 (s, 3H); $^{13}$C NMR (126 MHz, CDCl$_3$) δ 205.5, 173.8, 154.9, 139.1, 135.6, 130.9, 129.7, 128.9, 128.4, 126.9, 126.0, 125.2, 120.9, 112.1, 58.4, 55.6, 47.2, 31.9, 21.3, 20.1; IR (Neat Film NaCl) 2971, 2932, 1694, 1597, 1505, 1456, 1409, 1305, 1281, 1256, 1122, 1045, 1025, 969, 755 cm$^{-1}$; HRMS (MM: ESI-APCI+) m/z calc'd for C$_{20}$H$_{22}$NO$_3$ [M+H]$^+$: 324.1594, found 324.1601.

(S)-3-(4-(tert-Butyl)benzoyl)-1-(2-methoxyphenyl)-3-methylpyrrolidin-2-one (9)

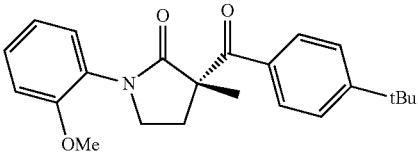

9

Lactam 9 was prepared according to the general procedure 3 from 1b using 4-(tert-butyl)benzonitrile in place of p-tolunitrile, and isolated by flash column chromatography (1:5 EtOAc:hexanes) on silica gel as a white solid. 89% yield, 92% ee. [α]$_D^{25}$ +6.9° (c 1.04, CHCl$_3$); $^1$H NMR (500 MHz, CDCl$_3$) ∂ 8.13-8.07 (m, 2H), 7.47-7.41 (m, 2H), 7.33-7.25 (m, 2H), 7.04-6.95 (m, 2H), 3.93-3.80 (m, 2H), 3.85 (s, 3H), 2.96 (ddd, J=12.9, 8.4, 6.5 Hz, 1H), 2.08 (ddd, J=12.8, 7.9, 4.8 Hz, 1H), 1.69 (s, 3H), 1.34 (s, 9H); $^{13}$C NMR (126 MHz, CDCl$_3$) δ 198.2, 175.0, 156.0, 155.0, 132.7, 129.5, 128.9, 128.4, 126.9, 125.2, 120.9, 112.1, 56.6, 55.7, 47.1, 35.0, 32.5, 31.1, 21.6; IR (Neat Film NaCl) 2963, 1701, 1676, 1603, 1504, 1459, 1406, 1272, 1255, 1121, 1109, 1023, 971, 752 cm$^{-1}$; HRMS (MM: ESI-APCI+) m/z calc'd for C$_{23}$H$_{28}$NO$_3$ [M+H]$^+$: 366.2064, found 366.2072.

(S)-3-(4-Methoxybenzoyl)-1-(2-methoxyphenyl)-3-methylpyrrolidin-2-one (10)

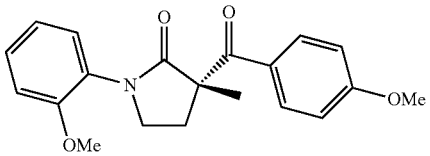

Lactam 10 was prepared according to the general procedure 3 from 1b using 4-methoxybenzonitrile in place of p-tolunitrile, and isolated by flash column chromatography (1:5 EtOAc:hexanes) on silica gel as a colorless oil. 85% yield, 89% ee. $[\alpha]_D^{25}$ −3.7° (c 0.73, CHCl$_3$); $^1$H NMR (500 MHz, CDCl$_3$) δ 8.24-8.17 (m, 2H), 7.32-7.27 (m, 2H), 7.03-6.88 (m, 4H), 3.93-3.87 (m, 1H), 3.87 (s, 3H), 3.83 (s, 3H), 3.83-3.77 (m, 1H), 2.97 (ddd, J=12.8, 8.2, 6.2 Hz, 1H), 2.07 (ddd, J=12.9, 8.0, 5.0 Hz, 1H), 1.68 (s, 3H); $^{13}$C NMR (126 MHz, CDCl$_3$) δ 196.8, 175.0, 162.9, 155.0, 132.1, 128.9, 128.3, 128.2, 127.0, 120.9, 113.4, 112.1, 56.6, 55.7, 55.4, 47.2, 32.7, 21.8; IR (Neat Film NaCl) 2971, 2933, 1695, 1600, 1504, 1464, 1456, 1410, 1307, 1259, 1174, 1027, 971, 845, 754, 699, 610 cm$^{-1}$; HRMS (MM: ESI-APCI+) m/z calc'd for C$_{20}$H$_{22}$NO$_4$ [M+H]$^+$: 340.1543, found 340.1547.

(S)-3-(4-Fluorobenzoyl)-1-(2-methoxyphenyl)-3-methylpyrrolidin-2-one (11)

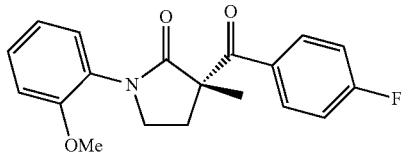

Lactam 11 was prepared according to the general procedure 3 from 1b using 4-fluorobenzonitrile in place of p-tolunitrile, and isolated by flash column chromatography (1:5 EtOAc:hexanes) on silica gel as a white solid. 36% yield, 96% ee. $[\alpha]_D^{25}$ −1.8° (c 0.77, CHCl$_3$); $^1$H NMR (500 MHz, CDCl$_3$) δ 8.28-8.20 (m, 2H), 7.34-7.27 (m, 1H), 7.27-7.20 (m, 1H), 7.14-7.06 (m, 2H), 7.04-6.95 (m, 2H), 3.91 (ddd, J=9.6, 8.3, 5.0 Hz, 1H), 3.85-3.76 (m, 4H), 3.83 (s, 3H), 2.95 (ddd, J=12.8, 8.3, 6.1 Hz, 1H), 2.12-2.03 (m, 1H), 1.68 (s, 3H); $^{13}$C NMR (126 MHz, CDCl$_3$) δ 197.1, 174.5, 165.2, 154.9, 132.4, 131.9, 129.1, 128.3, 126.7, 121.0, 115.3, 112.1, 56.9, 55.7, 47.2, 32.5, 21.7; IR (Neat Film NaCl) 2974, 1697, 1684, 1597, 1506, 1457, 1410, 1271, 1256, 1235, 1160, 1024, 972, 848, 754, 609 cm$^{-1}$; HRMS (MM: ESI-APCI+) m/z calc'd for C$_{19}$H$_{19}$FNO$_3$ [M+H]$^+$: 328.1343, found 328.1353.

(S)-1-(2-Methoxyphenyl)-3-methyl-3-(4-(trifluoromethyl)benzoyl)pyrrolidin-2-one (12)

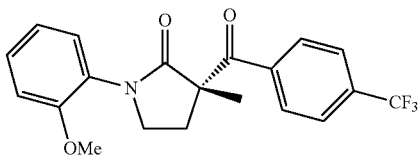

Lactam 12 was prepared according to the general procedure 3 from 1b using 4-trifluoromethylbenzonitrile in place of p-tolunitrile, and isolated by flash column chromatography (1:5 EtOAc:hexanes) on silica gel as a colorless oil. 23% yield, 87% ee. $[\alpha]_D^{25}$ +2.7° (c 0.71, CHCl$_3$); $^1$H NMR (500 MHz, CDCl$_3$) δ 8.29-8.22 (m, 2H), 7.78-7.61 (m, 2H), 7.35-7.29 (m, 1H), 7.24 (dd, J=7.7, 1.7 Hz, 1H), 7.05-6.95 (m, 2H), 3.91 (ddd, J=9.7, 8.3, 5.0 Hz, 1H), 3.84 (s, 3H), 3.83-3.77 (m, 1H), 2.93 (ddd, J=12.9, 8.3, 6.2 Hz, 1H), 2.09 (ddd, J=13.0, 8.0, 5.0 Hz, 1H), 1.69 (s, 3H); $^{13}$C NMR (126 MHz, CDCl$_3$) δ 198.4, 174.1, 154.9, 139.0, 133.7, 133.6, 129.7, 129.2, 128.3, 125.3, 123.6, 121.0, 112.1, 57.2, 55.7, 47.2, 32.1, 21.5; IR (Neat Film NaCl) 2975, 2934, 1697, 1505, 1409, 1328, 1316, 1257, 1169, 1127, 1068, 1020, 1009, 973, 858, 753; cm$^{-1}$; HRMS (MM: ESI-APCI+) m/z calc'd for C$_{20}$H$_{19}$F$_3$NO$_3$ [M+H]$^+$: 378.1312, found 378.1325.

(S)-3-(2-Naphthoyl)-1-(2-methoxyphenyl)-3-methyl-pyrrolidin-2-one (13)

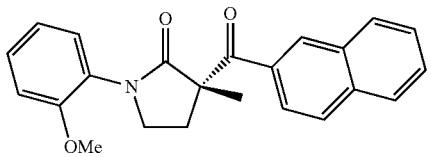

Lactam 13 was prepared according to the general procedure 3 from 1b using 2-naphthonitrile in place of p-tolunitrile, and isolated by flash column chromatography (1:5 EtOAc:hexanes) on silica gel as a colorless oil. 66% yield, 91% ee. $[\alpha]_D^{25}$ +15.8° (c 0.52, CHCl$_3$); $^1$HNMR (500 MHz, CDCl$_3$) δ 8.77 (d, J=1.3 Hz, 1H), 8.14 (dd, J=8.6, 1.8 Hz, 1H), 7.98-7.92 (m, 1H), 7.87 (t, J=8.4 Hz, 2H), 7.62-7.56 (m, 1H), 7.56-7.49 (m, 1H), 7.35-7.27 (m, 2H), 7.06-6.97 (m, 2H), 3.96 (ddd, J=9.6, 8.3, 4.9 Hz, 1H), 3.90-3.81 (m, 1H), 3.84 (s, 3H), 3.04 (ddd, J=12.9, 8.3, 6.2 Hz, 1H), 2.17-2.08 (m, 1H), 1.75 (s, 3H); $^{13}$C NMR (126 MHz, CDCl$_3$) δ 198.9, 174.7, 155.0, 135.1, 133.0, 132.4, 131.1, 129.8, 129.0, 128.3, 128.3, 128.0, 127.6, 127.0, 126.5, 125.4, 121.0, 112.2, 57.1, 55.7, 47.2, 32.6, 21.8; IR (Neat Film NaCl) 2930, 1694, 1505, 1463, 1409, 1281, 1255, 1120, 1024, 750 cm$^{-1}$; HRMS (MM: ESI-APCI+) m/z calc'd for C$_{23}$H$_{22}$NO$_3$ [M+H]$^+$: 360.1594, found 360.1589.

(S)-3-Ethyl-1-(2-methoxyphenyl)-3-(4-methylbenzoyl)pyrrolidin-2-one (14)

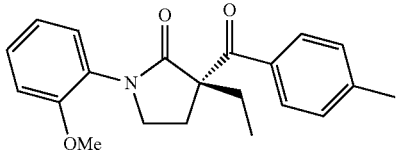

Lactam 14 was prepared according to the general procedure 3 from SI6, and isolated by flash column chromatography (1:5 EtOAc:hexanes) on silica gel as a colorless oil. 50% yield, 77% ee. $[\alpha]_D^{25}$ +14.6° (c 0.81, CHCl$_3$); $^1$H NMR (500 MHz, CDCl$_3$) δ 8.14 (d, J=8.3 Hz, 2H), 7.31-7.18 (m, 4H), 7.01-6.92 (m, 2H), 3.90 (ddd, J=9.5, 8.1, 6.7 Hz, 1H), 3.79 (s, 3H), 3.71 (ddd, J=9.5, 8.7, 4.3 Hz, 1H), 2.95 (ddd, J=13.0, 8.0, 4.2 Hz, 1H), 2.41-2.30 (m, 4H), 2.17-2.05 (m, 2H), 0.97 (t, J=7.5 Hz, 3H); $^{13}$C NMR (126 MHz, CDCl$_3$) δ 198.3, 173.5, 154.9, 143.0, 134.0, 129.5, 128.9, 128.9, 128.4, 127.1, 120.9, 112.1, 61.8, 55.6, 47.5, 29.5, 29.1, 21.6, 8.8; IR (Neat Film NaCl) 2962, 1700, 1606, 1504, 1461, 1253, 1159, 1024, 752 cm$^{-1}$; HRMS (MM: ESI-APCI+) m/z calc'd for C$_{21}$H$_{24}$NO$_3$ [M+H]$^+$: 338.1751, found 338.1753.

(S)-3-Benzyl-1-(2-methoxyphenyl)-3-(4-methylbenzoyl)pyrrolidin-2-one (15)

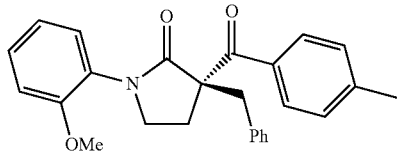

Lactam 15 was prepared according to the general procedure 3 from SI7, and isolated by flash column chromatography (1:5 EtOAc:hexanes) on silica gel as a colorless oil. 61% yield, 81% ee. [α]$_D^{25}$ +62.3° (c 0.90, CHCl$_3$); $^1$H NMR (500 MHz, CDCl$_3$) δ 8.13-8.06 (m, 2H), 7.31-7.16 (m, 8H), 6.93-6.83 (m, 3H), 3.77 (s, 3H), 3.62 (td, J=9.1, 4.1 Hz, 1H), 3.53 (d, J=13.7 Hz, 1H), 3.34 (d, J=13.7 Hz, 1H), 2.90-2.72 (m, 2H), 2.37 (s, 3H), 2.26 (ddd, J=13.0, 8.4, 4.1 Hz, 1H); $^{13}$C NMR (126 MHz, CDCl$_3$) δ 197.7, 173.1, 154.9, 143.2, 136.7, 133.3, 130.6, 129.7, 129.0, 128.9, 128.4, 127.9, 126.9, 126.7, 120.8, 112.0, 61.4, 55.6, 47.0, 40.9, 28.7, 21.7; IR (Neat Film NaCl) 2928, 1696, 1604, 1502, 1457, 1405, 1240, 1185, 1025, 741, 702 cm$^{-1}$; HRMS (MM: ESI-APCI+) m/z calc'd for C$_{26}$H$_{26}$NO$_3$ [M+H]$^+$: 400.1907, found 400.1919.

(S)-3-(4-Methoxybenzyl)-1-(2-methoxyphenyl)-3-(4-methylbenzoyl)pyrrolidin-2-one (16)

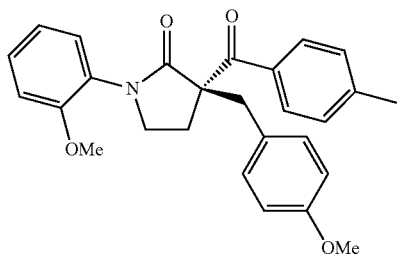

Lactam 16 was prepared according to the general procedure 3 from SI8, and isolated by flash column chromatography (1:5 EtOAc:hexanes) on silica gel as a colorless oil. 77% yield, 81% ee. [α]$_D^{25}$ +50.4° (c 1.21, CHCl$_3$); $^1$H NMR (500 MHz, CDCl$_3$) δ 8.16-8.09 (m, 2H), 7.30-7.18 (m, 5H), 6.99 (dd, J=8.0, 1.8 Hz, 1H), 6.98-6.88 (m, 2H), 6.88-6.80 (m, 2H), 3.81 (s, 3H), 3.80 (s, 3H), 3.67 (td, J=9.2, 4.2 Hz, 1H), 3.51 (d, J=13.9 Hz, 1H), 3.32 (d, J=13.9 Hz, 1H), 2.95 (ddd, J=9.4, 8.6, 6.5 Hz, 1H), 2.80 (ddd, J=13.3, 9.0, 6.4 Hz, 1H), 2.40 (s, 3H), 2.27 (ddd, J=13.0, 8.6, 4.2 Hz, 1H); $^{13}$C NMR (126 MHz, CDCl$_3$) δ 197.9, 173.2, 158.7, 154.9, 143.1, 133.4, 131.5, 129.7, 129.0, 128.8, 128.6, 127.9, 126.7, 120.8, 113.7, 112.0, 61.5, 55.6, 55.3, 47.0, 40.1, 28.7, 21.6; IR (Neat Film NaCl) 2930, 1694, 1606, 1505, 1463, 1409, 1301, 1248, 1180, 1028, 832, 753 cm$^{-1}$; HRMS (MM: ESI-APCI+) m/z calc'd for C$_{27}$H$_{28}$NO$_4$ [M+H]$^+$: 430.2013, found 430.2006.

(S)-3-(4-Fluorobenzyl)-1-(2-methoxyphenyl)-3-(4-methylbenzoyl)pyrrolidin-2-one (17)

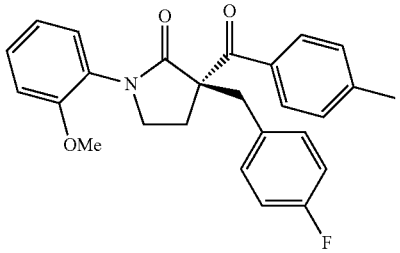

Lactam 17 was prepared according to the general procedure 3 from SI9, and isolated by flash column chromatography (1:5 EtOAc:hexanes) on silica gel as a white foam. 76% yield, 74% ee. [α]$_D^{25}$ +38.9° (c 3.08, CHCl$_3$); $^1$H NMR (500 MHz, CDCl$_3$) δ 8.15-8.08 (m, 2H), 7.31-7.21 (m, 5H), 7.04-6.91 (m, 5H), 3.79 (s, 3H), 3.67 (td, J=9.3, 4.4 Hz, 1H), 3.54 (d, J=13.9 Hz, 1H), 3.34 (d, J=13.9 Hz, 1H), 3.00 (ddd, J=9.5, 8.7, 6.3 Hz, 1H), 2.81 (ddd, J=13.4, 9.1, 6.3 Hz, 1H), 2.41 (s, 3H), 2.26 (ddd, J=13.3, 8.7, 4.4 Hz, 1H); $^{13}$C NMR (126 MHz, CDCl$_3$) δ 197.6, 172.9, 163.1, 161.1, 154.8, 143.3, 133.2, 132.4, 132.0, 132.0, 129.6, 129.1, 128.9, 127.8, 126.5, 120.9, 115.3, 115.1, 112.0, 61.4, 55.6, 47.0, 40.1, 28.6, 21.7; IR (Neat Film NaCl) 2931, 1697, 1604, 1504, 1465, 1410, 1222, 1185, 1026, 909, 833, 752, 731 cm$^{-1}$; HRMS (MM: ESI-APCI+) m/z calc'd for C$_{26}$H$_{25}$FNO$_3$ [M+H]$^+$: 418.1813, found 418.1806.

(R)-1-(2-Methoxyphenyl)-3-(4-methylbenzoyl)-3-(2,2,2-trifluoroethyl)pyrrolidin-2-one (18)

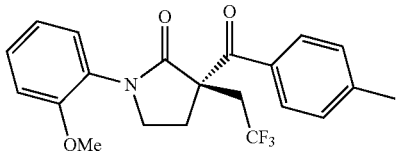

Lactam 18 was prepared according to the general procedure 3 from SI10, and isolated by flash column chromatography (1:5 EtOAc:hexanes) on silica gel as a colorless oil. 58% yield, 71% ee. [α]$_D^{25}$ +10.3° (c 2.16, CHCl$_3$); $^1$H NMR (500 MHz, CDCl$_3$) δ 8.16-8.09 (m, 2H), 7.34-7.28 (m, 1H), 7.28-7.17 (m, 3H), 7.03-6.92 (m, 2H), 4.00 (ddd, J=9.6, 7.7, 6.8 Hz, 1H), 3.78 (s, 3H), 3.72 (ddd, J=9.6, 8.7, 3.9 Hz, 1H), 3.34 (dq, J=15.8, 11.1 Hz, 1H), 3.10-3.01 (m, 1H), 2.87 (dq, J=15.7, 11.1 Hz, 1H), 2.40 (s, 4H); $^{13}$C NMR (126 MHz, CDCl$_3$) δ 195.1, 171.4, 154.8, 143.5, 133.0, 129.6, 129.3, 129.1, 128.1, 127.5, 126.4, 125.3, 121.0, 112.0, 57.7, 55.6, 47.6, 39.3, 39.1, 38.9, 38.7, 29.1, 29.0, 21.6; IR (Neat Film NaCl) 2952, 1703, 1673, 1505, 1464, 1373, 1299, 1260, 1143, 1021, 753 cm$^{-1}$; HRMS (MM: ESI-APCI+) m/z calc'd for C$_{21}$H$_{21}$F$_3$NO$_3$ [M+H]$^+$: 392.1468, found 392.1459.

(S)-3-(3-(Benzyloxy)propyl)-1-(2-methoxyphenyl)-3-(4-methylbenzoyl)pyrrolidin-2-one (19)

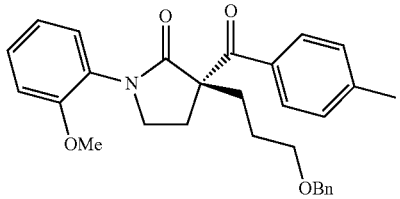

Lactam 19 was prepared according to the general procedure 3 from SI11, and isolated by flash column chromatography (1:5 EtOAc:hexanes) on silica gel as a colorless oil. 67% yield, 60% ee. $[\alpha]_D^{25}$ +9.3° (c 2.90, CHCl$_3$); $^1$H NMR (500 MHz, CDCl$_3$) δ 8.16-8.10 (m, 1H), 7.37-7.18 (m, 6H), 7.01-6.92 (m, 1H), 4.45 (d, J=2.3 Hz, 1H), 3.88 (ddd, J=9.5, 8.0, 6.6 Hz, 1H), 3.77 (s, 1H), 3.76-3.66 (m, 1H), 3.46 (td, J=6.4, 1.1 Hz, 1H), 2.38 (s, 2H), 2.19-2.07 (m, 1H), 1.77-1.58 (m, 1H); $^{13}$C NMR (126 MHz, CDCl$_3$) δ 198.0, 173.4, 154.9, 143.0, 138.5, 133.8, 129.5, 128.9, 128.9, 128.4, 128.3, 127.6, 127.5, 127.0, 120.9, 112.0, 72.8, 70.3, 61.1, 55.6, 47.5, 32.8, 30.0, 24.8, 21.6; IR (Neat Film NaCl) 2935, 1698, 1606, 1504, 1455, 1408, 1302, 1279, 1252, 1185, 1101, 1027, 750, 699 cm$^{-1}$; HRMS (MM: ESI-APCI+) m/z calc'd for C$_{29}$H$_{32}$NO$_4$ [M+H]$^+$: 458.2326, found 458.2315.

(S)-1-(2-Methoxyphenyl)-3-(4-methylbenzoyl)-3-(3-methylbut-2-en-1-yl)pyrrolidin-2-one (20)

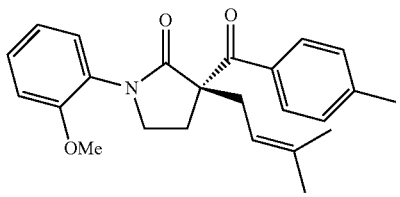

Lactam 20 was prepared according to the general procedure 3 from SI12, and isolated by flash column chromatography (1:5 EtOAc:hexanes) on silica gel as a pale yellow oil. 71% yield, 76% ee. $[\alpha]_D^{25}$ +29.6° (c 2.15, CHCl$_3$); $^1$H NMR (500 MHz, CDCl$_3$) δ 8.14-8.07 (m, 2H), 7.32-7.25 (m, 2H), 7.25-7.18 (m, 2H), 7.02-6.92 (m, 2H), 5.23-5.15 (m, 1H), 3.88 (ddd, J=9.5, 8.5, 5.7 Hz, 1H), 3.83 (s, 3H), 3.68 (ddd, J=9.4, 8.7, 5.1 Hz, 1H), 3.02-2.93 (m, 1H), 2.89-2.73 (m, 2H), 2.39 (s, 3H), 2.14 (ddd, J=13.0, 8.7, 5.7 Hz, 1H), 1.72 (s, 3H), 1.59 (s, 3H); $^{13}$C NMR (126 MHz, CDCl$_3$) δ 198.2, 173.5, 155.0, 142.9, 135.5, 133.8, 129.5, 128.9, 128.9, 128.3, 127.1, 120.9, 118.6, 112.1, 61.1, 55.6, 47.5, 34.5, 29.2, 26.1, 21.6, 18.0; IR (Neat Film NaCl) 2917, 1698, 1606, 1504, 1463, 1408, 1248, 1184, 1123, 1024, 753 cm$^{-1}$; HRMS (MM: ESI-APCI+) m/z calc'd for C$_{24}$H$_{28}$NO$_3$ [M+H]$^+$: 378.2064, found 378.2060.

(S,E)-3-(But-2-en-1-yl)-1-(2-methoxyphenyl)-3-(4-methylbenzoyl)pyrrolidin-2-one (21)

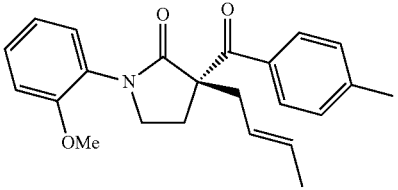

Lactam 21 was prepared according to the general procedure 3 from SI13, and isolated by flash column chromatography (1:8 EtOAc:hexanes) on silica gel as a pale yellow oil. 70% yield, 86% ee. $[\alpha]_D^{25}$ +45.5° (c 2.10, CHCl$_3$); $^1$H NMR (500 MHz, CDCl$_3$) δ 8.08 (d, J=8.3 Hz, 2H), 7.34-7.19 (m, 4H), 7.03-6.94 (m, 2H), 5.63-5.43 (m, 2H), 3.92-3.86 (m, 1H), 3.84 (s, 3H), 3.73-3.62 (m, 1H), 2.94-2.72 (m, 3H), 2.39 (s, 3H), 2.20 (ddd, J=13.2, 8.7, 5.3 Hz, 1H), 1.68 (dq, J=6.3, 1.2 Hz, 3H); $^{13}$C NMR (126 MHz, CDCl$_3$) δ 198.0, 173.5, 155.0, 143.0, 133.7, 129.8, 129.5, 129.5, 128.9, 128.3, 127.0, 125.4, 120.9, 112.1, 60.7, 55.6, 47.4, 39.1, 28.9, 21.6, 18.2; IR (Neat Film NaCl) 2917, 1698, 1606, 1504, 1463, 1408, 1254, 1185, 1122, 1045, 1024, 973, 837, 750 cm$^{-1}$; HRMS (MM: ESI-APCI+) m/z calc'd for C$_{23}$H$_{26}$NO$_3$ [M+H]$^+$: 364.1907, found 364.1909.

(S)-3-Cinnamyl-1-(2-methoxyphenyl)-3-(4-methylbenzoyl)pyrrolidin-2-one (22)

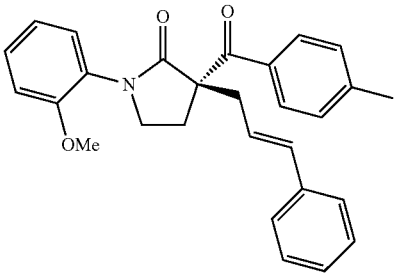

Lactam 22 was prepared according to the general procedure 3 from SI14, and isolated by flash column chromatography (1:5 EtOAc:hexanes) on silica gel as a white foam. 60% yield, 86% ee. $[\alpha]_D^{25}$ +55.5° (c 0.93, CHCl$_3$); $^1$H NMR (500 MHz, CDCl$_3$) δ 8.11-8.05 (m, 2H), 7.41-7.33 (m, 2H), 7.33-7.18 (m, 10H), 7.00-6.93 (m, 2H), 6.52 (d, J=15.8 Hz, 1H), 6.29 (dt, J=15.5, 7.6 Hz, 1H), 3.92-3.82 (m, 1H), 3.80 (s, 3H), 3.75 (ddd, J=9.6, 8.7, 5.7 Hz, 1H), 3.05 (dt, J=7.4, 1.4 Hz, 2H), 2.85 (ddd, J=13.3, 8.9, 5.8 Hz, 1H), 2.41 (s, 2H), 2.30 (ddd, J=13.5, 8.7, 5.0 Hz, 1H); $^{13}$C NMR (126 MHz, CDCl$_3$) δ 197.9, 173.3, 155.0, 143.1, 137.3, 134.2, 133.5, 129.4, 129.0, 129.0, 128.5, 128.3, 127.4, 126.8, 126.2, 124.8, 121.0, 112.1, 60.7, 55.6, 47.3, 39.4, 28.8, 21.6; IR (Neat Film NaCl) 2961, 1698, 1606, 1504, 1463, 1409, 1279, 1255, 1185, 1025, 971, 911, 742, 694 cm$^{-1}$; HRMS (MM: ESI-APCI+) m/z calc'd for C$_{28}$H$_{28}$NO$_3$ [M+H]$^+$: 426.2064, found 426.2067.

(S,E)-1-(2-Methoxyphenyl)-3-(4-methylbenzoyl)-3-(3-(p-tolyl)allyl)pyrrolidin-2-one (23)

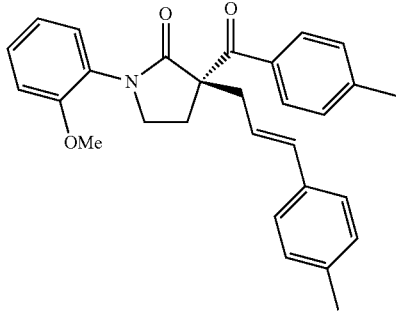

Lactam 23 was prepared according to the general procedure 3 from SI15, and isolated by flash column chromatography (1:5 EtOAc:hexanes) on silica gel as a pale yellow oil. 85% yield, 88% ee. $[\alpha]_D^{25}$ +56.0° (c 2.93, CHCl$_3$); $^1$H NMR (500 MHz, CDCl$_3$) δ 8.08 (d, J=8.3 Hz, 2H), 7.33-7.25 (m, 2H), 7.25-7.19 (m, 4H), 7.14-7.08 (m, 2H), 7.00-6.93 (m, 2H), 6.49 (d, J=15.7 Hz, 1H), 6.23 (dt, J=15.5, 7.6 Hz, 1H), 3.92-3.83 (m, 1H), 3.81 (s, 3H), 3.78-3.69 (m, 1H), 3.04 (d, J=7.6 Hz, 2H), 2.85 (ddd, J=13.2, 8.9, 5.8 Hz, 1H), 2.40 (s, 3H), 2.39-2.25 (m, 4H); $^{13}$C NMR (126 MHz, CDCl$_3$) δ 197.9, 173.4, 155.0, 143.1, 137.1, 134.5, 134.0, 133.5, 129.4, 129.2, 129.0, 129.0, 128.3, 126.8, 126.1, 123.6, 121.0, 112.0, 60.7, 55.6, 47.4, 39.4, 28.8, 21.6, 21.2; IR (Neat Film NaCl) 2920, 1694, 1606, 1505, 1463, 1409, 1279, 1254, 1184, 1121, 1045, 1025, 974, 911, 838, 752 cm$^{-1}$; HRMS (MM: ESI-APCI+) m/z calc'd for C$_{29}$H$_{30}$NO$_3$ [M+H]$^+$: 440.2220, found 440.2220.

(S,E)-1-(2-Methoxyphenyl)-3-(3-(4-methoxyphenyl)allyl)-3-(4-methylbenzoyl) pyrrolidin-2-one (24)

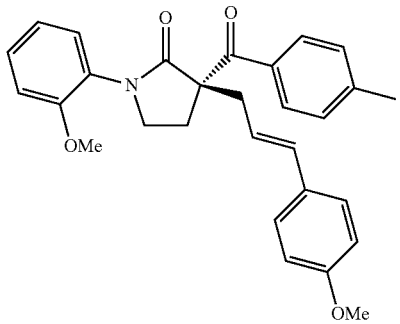

Lactam 24 was prepared according to the general procedure 3 from SI16, and isolated by flash column chromatography (1:5 EtOAc:hexanes) on silica gel as a white foam. 68% yield, 88% ee. $[\alpha]_D^{25}$ +57.6° (c 1.09, CHCl$_3$, 88% ee); $^1$H NMR (500 MHz, CDCl$_3$) δ 8.11-8.05 (m, 2H), 7.34-7.26 (m, 3H), 7.26-7.17 (m, 3H), 7.00-6.93 (m, 2H), 6.87-6.81 (m, 2H), 6.46 (d, J=15.7 Hz, 1H), 6.13 (dt, J=15.5, 7.5 Hz, 1H), 3.88 (td, J=9.2, 4.9 Hz, 1H), 3.81 (s, 3H), 3.80 (s, 3H), 3.80-3.67 (m, 1H), 3.03 (dt, J=7.6, 1.4 Hz, 2H), 2.85 (ddd, J=13.2, 8.9, 5.8 Hz, 1H), 2.40 (s, 3H), 2.35-2.23 (m, 1H); $^{13}$C NMR (126 MHz, CDCl$_3$) δ 197.9, 173.4, 159.0, 155.0, 143.1, 133.5, 130.1, 129.4, 129.0, 128.9, 128.3, 127.4, 126.8, 122.4, 121.0, 113.9, 112.1, 60.8, 55.6, 55.3, 47.4, 39.4, 28.8, 21.6; IR (Neat Film NaCl) 2957, 1699, 1607, 1505, 1464, 1249, 1175, 1027, 838, 752 cm$^{-1}$; HRMS (MM: ESI-APCI+) m/z calc'd for C$_{29}$H$_3$NO$_4$ [M+H]$^+$: 456.2169, found 456.2164.

(S,E)-3-(3-(4-Fluorophenyl)allyl)-1-(2-methoxyphenyl)-3-(4-methylbenzoyl) pyrrolidin-2-one (25)

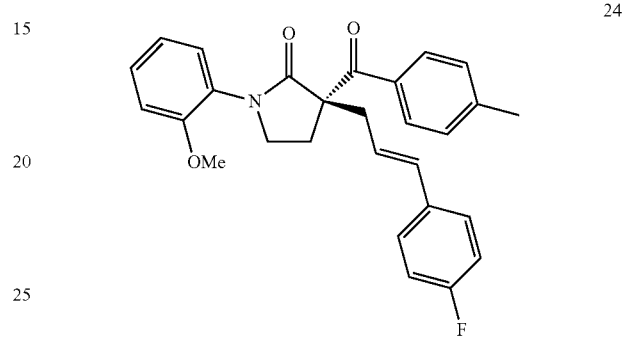

Lactam 25 was prepared according to the general procedure 3 from SI17, and isolated by flash column chromatography (1:10 EtOAc:hexanes) on silica gel as a white foam. 62% yield, 83% ee. $[\alpha]_D^{25}$ +40.7° (c 0.55, CHCl$_3$); $^1$H NMR (500 MHz, CDCl$_3$) δ 8.07 (d, J=8.3 Hz, 2H), 7.35-7.26 (m, 3H), 7.26-7.22 (m, 2H), 7.22-7.18 (m, 1H), 7.06-6.93 (m, 4H), 6.51-6.44 (m, 1H), 6.20 (dt, J=15.5, 7.6 Hz, 1H), 3.88 (ddd, J=9.6, 8.9, 5.0 Hz, 1H), 3.79 (s, 3H), 3.78-3.69 (m, 1H), 3.04 (ddd, J=7.2, 3.6, 1.3 Hz, 2H), 2.86 (ddd, J=13.2, 8.9, 5.7 Hz, 1H), 2.41 (s, 3H), 2.38-2.23 (m, 2H); $^{13}$C NMR (126 MHz, CDCl$_3$) δ 197.8, 173.2, 163.1, 161.2, 154.9, 143.2, 133.5, 132.9, 129.4, 129.1, 129.0, 128.2, 127.7, 126.8, 124.6, 121.0, 115.5, 115.3, 112.1, 60.7, 55.6, 47.3, 39.3, 28.9, 21.6; IR (Neat Film NaCl) 2944, 1693, 1604, 1505, 1460, 1412, 1254, 1228, 1184, 1158, 1045, 1024, 910, 838, 753, 731 cm$^{-1}$; HRMS (MM: ESI-APCI+) m/z calc'd for C$_{28}$H$_{27}$FNO$_3$ [M+H]$^+$: 444.1969, found 444.1969.

(S,E)-1-(2-Methoxyphenyl)-3-(4-methylbenzoyl)-3-(3-(thiophen-3-yl)allyl) pyrrolidin-2-one (26)

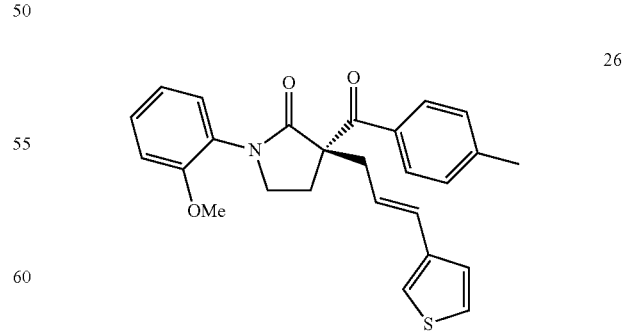

Lactam 26 was prepared according to the general procedure 3 from SI18, and isolated by flash column chromatography (1:5 EtOAc:hexanes) on silica gel as a pale yellow oil. 76% yield, 83% ee. $[\alpha]_D^{25}$ +46.7° (c 1.17, CHCl$_3$); $^1$H NMR (500 MHz, CDCl$_3$) δ 8.12-8.01 (m, 2H), 7.33-7.14 (m, 6H), 7.10 (dd, J=3.0, 1.2 Hz, 1H), 7.00-6.93 (m, 2H), 6.53 (d, J=15.7 Hz, 1H), 6.13 (dt, J=15.5, 7.6 Hz, 1H), 3.88 (td, J=9.1, 4.9 Hz, 1H), 3.81 (s, 3H), 3.79-3.68 (m, 1H), 3.01 (dd, J=7.7, 1.3 Hz, 2H), 2.85 (ddd, J=13.3, 8.9, 5.8 Hz, 1H), 2.40 (s, 3H), 2.28 (ddd, J=13.5, 8.8, 5.0 Hz, 1H); $^{13}$C NMR (126 MHz, CDCl$_3$) δ 197.8, 173.3, 155.0, 143.2, 139.9, 133.4, 129.4, 129.0, 129.0, 128.4, 128.2, 126.8, 126.0, 125.0, 124.6, 121.5, 121.0, 112.1, 60.7, 55.6, 47.3, 39.3, 28.8, 21.6; IR (Neat Film NaCl) 2958, 1698, 1606, 1504, 1463, 1409, 1302, 1279, 1254, 1184, 1122, 1024, 967, 836, 753 cm$^{-1}$; HRMS (MM: ESI-APCI+) m/z calc'd for C$_{26}$H$_{25}$NO$_3$S [M+H]$^+$: 432.1628, found 432.1622.

(S)-1-(2-Methoxyphenyl)-3-(4-methylbenzoyl)-3-((2E,4E)-5-phenylpenta-2,4-dien-1-yl)pyrrolidin-2-one (27)

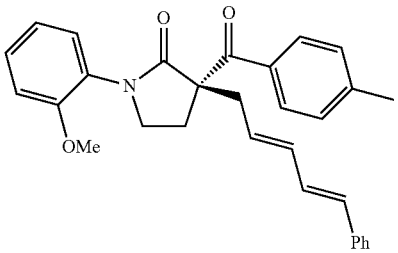

27

Lactam 27 was prepared according to the general procedure 3 from SI19, and isolated by flash column chromatography (1:5 EtOAc:hexanes) on silica gel as a pale yellow oil. 35% yield, 84% ee. [α]$_D^{25}$ +40.6° (c 1.45, CHCl$_3$); $^1$H NMR (500 MHz, CDCl$_3$) δ 8.09 (d, J=8.3 Hz, 2H), 7.42-7.36 (m, 2H), 7.36-7.16 (m, 6H), 6.98 (d, J=7.8 Hz, 2H), 6.76 (ddd, J=15.7, 10.5, 0.9 Hz, 1H), 6.49 (d, J=15.7 Hz, 1H), 6.38-6.29 (m, 1H), 5.87 (dt, J=15.2, 7.7 Hz, 1H), 3.90 (ddd, J=9.5, 8.8, 5.1 Hz, 1H), 3.85 (s, 3H), 3.77-3.69 (m, 1H), 3.08-2.92 (m, 2H), 2.86 (ddd, J=13.2, 8.8, 5.6 Hz, 1H), 2.41 (s, 3H), 2.25 (ddd, J=13.7, 8.8, 5.2 Hz, 1H); $^{13}$C NMR (126 MHz, CDCl$_3$) δ 197.8, 173.2, 155.0, 143.1, 137.3, 134.8, 133.5, 131.6, 129.5, 129.1, 129.0, 129.0, 128.7, 128.6, 128.4, 127.4, 126.8, 126.3, 121.0, 112.1, 60.8, 55.7, 47.3, 39.3, 29.0, 21.6; IR (Neat Film NaCl) 3024, 1694, 1606, 1505, 1463, 1409, 1304, 1253, 1185, 1122, 1045, 1026, 992, 910, 747, 693 cm$^{-1}$; HRMS (MM: ESI-APCI+) m/z calc'd for C$_{30}$H$_{30}$NO$_3$ [M+H]$^+$: 452.2220, found 452.2220.

Derivatization of C-Acylation Products

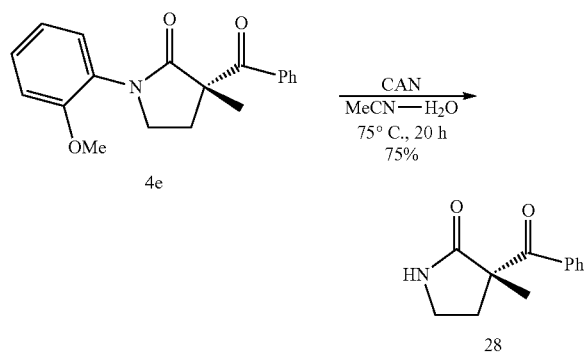

(S)-3-Benzoyl-3-methylpyrrolidin-2-one (28)

To a solution lactam 4e (93% ee, 40.0 mg, 0.129 mmol, 1.00 equiv) in MeCN (0.6 mL) and water (0.6 mL) was added CAN (424 mg, 0.774 mmol, 6.00 equiv) and the reaction mixture was stirred at 70° C. for 24 h. The reaction mixture was allowed to cool to ambient temperature and brine (5 mL) was added. The reaction mixture was extracted with AcOEt (30 mL), dried over Na$_2$SO$_4$, and concentrated under reduced pressure. The residue was purified by flash column chromatography (1:2 to 2:1 EtOAc:hexanes) on silica gel to give lactam 28 as a white solid (19.6 mg, 75% yield). [α]$_D^{25}$ +25.7° (c 0.20, CHCl$_3$); $^1$H NMR (500 MHz, CDCl$_3$) δ 8.05-7.99 (m, 2H), 7.56-7.48 (m, 1H), 7.47-7.39 (m, 2H), 5.83 (s, 1H), 3.59-3.50 (m, 1H), 3.50-3.42 (m, 1H), 2.92 (ddd, J=13.4, 8.1, 5.5 Hz, 1H), 2.08 (ddd, J=13.3, 8.1, 5.5 Hz, 1H), 1.60 (s, 3H); $^{13}$C NMR (126 MHz, CDCl$_3$) δ 199.1, 178.3, 135.7, 132.5, 129.1, 128.4, 55.9, 39.6, 34.5, 21.5; IR (Neat Film NaCl) 3246, 2978, 1667, 1595, 1444, 1307, 1265, 1207, 1008, 973, 782, 701, 651 cm$^{-1}$; HRMS (MM: ESI-APCI+) m/z calc'd for C$_{12}$H$_{14}$NO$_2$ [M+H]$^+$: 204.1019, found 204.1015.

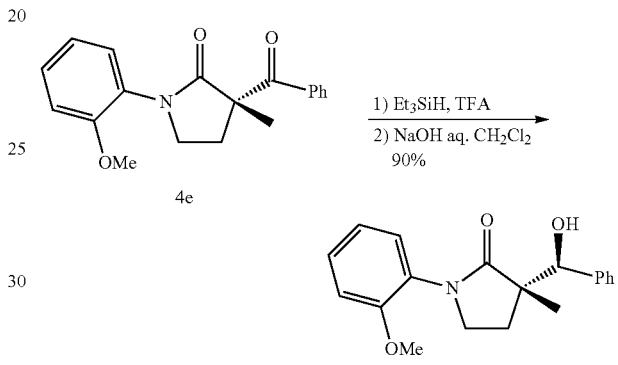

(S)-3-((S)-Hydroxy(phenyl)methyl)-1-(2-methoxyphenyl)-3-methylpyrrolidin-2-one (29)

To a solution lactam 4e (92% ee, 99.5 mg, 0.322 mmol, 1.00 equiv) in TFA (1.6 mL) was added Et$_3$SiH (0.102 mL, 643 mmol, 2.00 equiv) and the reaction mixture was stirred at ambient temperature for 24 h. CH$_2$Cl$_2$ (4 mL) and 2 M NaOH aqueous solution (8 mL) was added and the reaction mixture was stirred at ambient temperature for 3 h. The mixture was extracted with CH$_2$Cl$_2$ (30 mL, twice), washed with brine (10 mL), dried over Na$_2$SO$_4$, and concentrated under reduced pressure. The residue was purified by flash column chromatography (1:2 EtOAc:hexanes) on silica gel to give lactam 29 as a white solid (90.2 mg, 90% yield). [α]$_D^{25}$ −12.5° (c 1.10, CHCl$_3$); $^1$H NMR (500 MHz, CDCl$_3$) δ 7.49-7.43 (m, 2H), 7.43-7.27 (m, 4H), 7.22 (dd, J=7.7, 1.7 Hz, 1H), 7.03-6.94 (m, 2H), 5.18 (br s, 1H), 4.99 (s, 1H), 3.84 (s, 3H), 3.69 (td, J=9.4, 6.9 Hz, 1H), 3.54 (ddd, J=9.6, 8.8, 2.2 Hz, 1H), 2.31 (dt, J=12.6, 9.0 Hz, 1H), 1.54 (ddd, J=12.6, 6.9, 2.2 Hz, 1H), 1.27 (s, 3H); $^{13}$C NMR (126 MHz, CDCl$_3$) δ 180.3, 154.8, 139.4, 129.1, 128.5, 127.9, 127.7, 127.3, 126.5, 120.9, 112.1, 77.8, 55.7, 47.3, 46.9, 30.8, 15.6; IR (Neat Film NaCl) 3400, 2966, 1672, 1596, 1504, 1459, 1413, 1305, 1281, 1256, 1180, 1161, 1121, 1082, 1046, 1026, 917, 885, 753, 725, 703, cm$^{-1}$; HRMS (MM: ESI-APCI+) m/z calc'd for C$_{19}$H$_{22}$NO$_3$ [M+H]$^+$: 312.1594, found 312.1595.

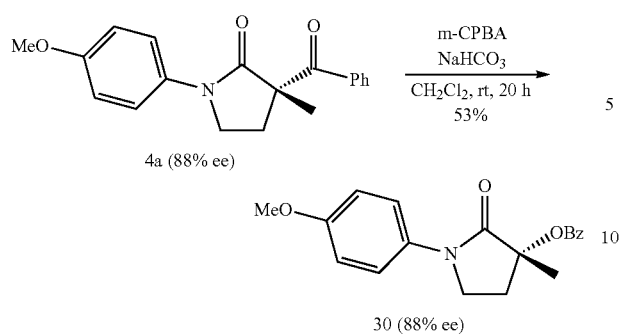

(R)-1-(4-Methoxyphenyl)-3-methyl-2-oxopyrrolidin-3-yl benzoate (30)

To a solution lactam 4a (88% ee, 30.9 mg, 0.100 mmol, 1.00 equiv) in CH$_2$Cl$_2$ (1 mL) and were added NaHCO$_3$ (42.0 mg, 0.500 mmol, 5.00 equiv) and m-CPBA (75%, 115.0 mg, 0.500 mmol, 5.00 equiv) and the reaction mixture was stirred at ambient temperature for 20 h. 10% NaHCO$_3$ aqueous solution (3 mL) and brine (3 mL) were added and the mixture was extracted with CH$_2$C$_{12}$ (30 mL, twice), dried over Na$_2$SO$_4$, and concentrated under reduced pressure. The residue was purified by flash column chromatography (1:5 EtOAc:hexanes) on silica gel to give lactam 30 as a white solid (17.1 mg, 53% yield, 88% ee). [α]$^{25}$ −3.3° (c 0.25, CHCl$_3$); $^1$H NMR (500 MHz, CDCl$_3$) δ 8.10-8.00 (m, 2H), 7.63-7.51 (m, 3H), 7.47-7.40 (m, 2H), 6.96-6.89 (m, 2H), 3.96 (td, J=9.6, 3.2 Hz, 1H), 3.82 (s, 3H), 2.84-2.74 (m, 1H), 2.40 (ddd, J=13.3, 8.1, 3.2 Hz, 1H), 1.75 (d, J=0.7 Hz, 3H); $^{13}$C NMR (126 MHz, CDCl$_3$) δ 171.2, 165.5, 156.9, 133.2, 132.5, 129.9, 129.9, 128.3, 121.9, 114.1, 81.2, 55.5, 44.9, 30.6, 23.3; IR (Neat Film NaCl) 2963, 1705, 1512, 1451, 1403, 1317, 1292, 1251, 1136, 1116, 1091, 1072, 1032, 828, 715 cm$^{-1}$; HRMS (MM: ESI-APCI+) m/z calc'd for C$_{19}$H$_{20}$NO$_4$ [M+H]$^+$: 326.1387, found 326.1381.

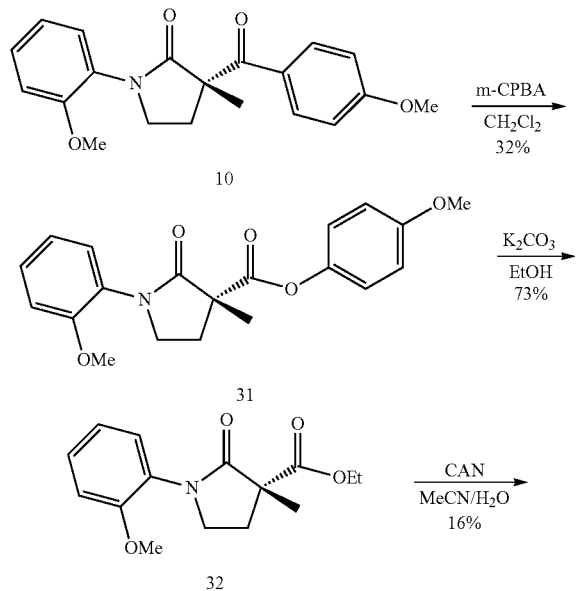

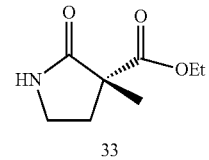

(R)-4-Methoxyphenyl-1-(2-methoxyphenyl)-3-methyl-2-oxopyrrolidine-3-carboxylate (31)

To a solution lactam 10 (160 mg, 0.471 mmol, 1.00 equiv) in CH$_2$Cl$_2$ (9.4 mL) was added m-CPBA (75%, 1.08 g, 4.71 mmol, 10.0 equiv) and the reaction mixture was stirred at ambient temperature for 24 h and then refluxed for 48 h. The reaction mixture was allowed to cool to ambient temperature and 10% Na$_2$SO$_3$ aqueous solution (30 mL) and saturated NaHCO$_3$ aqueous solution (10 mL) were added. The mixture was extracted with CH$_2$Cl$_2$ (130 mL), washed with brine (20 mL), dried over Na$_2$SO$_4$, and concentrated under reduced pressure. The residue was purified by flash column chromatography (1:5 EtOAc:hexanes) on silica gel to give lactam 31 as a pale yellow oil (54.2 mg, 32% yield). [α]$_D^{25}$ −11.7° (c 0.56, CHCl$_3$); $^1$H NMR (500 MHz, CDCl$_3$) δ 7.32-7.27 (m, 2H), 7.09-7.02 (m, 2H), 7.02-6.93 (m, 2H), 6.93-6.85 (m, 2H), 3.92-3.75 (m, 2H), 3.81 (s, 3H), 3.80 (s, 3H), 2.84 (ddd, J=12.9, 7.8, 4.5 Hz, 1H), 2.21 (ddd, J=12.9, 8.3, 6.8 Hz, 1H), 1.67 (s, 3H); $^{13}$C NMR (126 MHz, CDCl$_3$) δ 172.9, 171.6, 157.3, 154.9, 144.3, 129.0, 128.6, 126.9, 122.2, 120.9, 114.4, 112.1, 55.7, 55.6, 51.8, 47.1, 32.1, 20.2; IR (Neat Film NaCl) 2936, 1760, 1699, 1597, 1505, 1463, 1410, 1305, 1251, 1193, 1112, 1088, 1027, 754 cm$^{-1}$; HRMS (MM: ESI-APCI+) m/z calc'd for C$_{20}$H$_{22}$NO$_5$ [M+H]$^+$: 356.1492, found 356.1489.

(R)-Ethyl-1-(2-methoxyphenyl)-3-methyl-2-oxopyrrolidine-3-carboxylate (32)

To a solution lactam 31 (36.0 mg, 0.101 mmol, 1.00 equiv) in EtOH (2.0 mL) was added K$_2$CO$_3$ (70.0 mg, 0.506 mmol, 5.00 equiv) and the reaction mixture was stirred at ambient temperature for 30 h. The reaction mixture was concentrated under reduced pressure and brine was added to the residue. The mixture was extracted with AcOEt (15 mL), dried over Na$_2$SO$_4$, and concentrated under reduced pressure. The residue was purified by flash column chromatography (1:2 EtOAc:hexanes) on silica gel to give lactam 32 as a pale yellow oil (20.5 mg, 73% yield). [α]$_D^{25}$ −14.6° (c 0.98, CHCl$_3$); $^1$H NMR (500 MHz, CDCl$_3$) δ 7.31-7.24 (m, 2H), 7.03-6.88 (m, 2H), 4.31-4.17 (m, 2H), 3.83 (s, 3H), 3.82-3.70 (m, 2H), 2.64 (ddd, J=12.8, 7.0, 4.7 Hz, 1H), 2.14-2.04 (m, 1H), 1.55 (s, 3H), 1.31 (t, J=7.1 Hz, 3H); $^{13}$C NMR (126 MHz, CDCl$_3$) δ 173.3, 172.6, 154.9, 128.8, 128.5, 127.1, 120.9, 112.1, 61.5, 55.7, 51.6, 47.1, 32.2, 20.3, 14.2; IR (Neat Film NaCl) 2979, 1738, 1699, 1597, 1505, 1456, 1409, 1257, 1195, 1137, 1090, 1024, 754 cm$^{-1}$; HRMS (MM: ESI-APCI+) m/z calc'd for C$_{15}$H$_{20}$NO$_4$ [M+H]$^+$: 278.1387, found 278.1384.

(R)-Ethyl-3-methyl-2-oxopyrrolidine-3-carboxylate (33)

To a solution lactam 32 (20.0 mg, 0.0721 mmol, 1.00 equiv) in MeCN (1.5 mL) and water (1.5 mL) was added CAN (237 mg, 0.433 mmol, 6.00 equiv) and the reaction mixture was stirred at 40° C. for 24 h. The reaction mixture was allowed to cool to ambient temperature and 10% Na$_2$SO$_3$ aqueous solution (3 mL) and brine (3 mL) were added. The reaction mixture was extracted with AcOEt (20 mL, twice), dried over Na$_2$SO$_4$, and concentrated under reduced pressure. The residue was purified by flash column chromatography (2:1 EtOAc:hexanes) on silica gel to give lactam 28 as a white solid (2.0 mg, 16% yield). $[\alpha]_D^{25}$ +19.5° (c 0.09, MeOH) (reported data $[\alpha]_D^{25}$ +19.0° (c 2, MeOH))[8]; $^1$H NMR (500 MHz, CDCl$_3$) δ 5.83 (br s, 1H), 4.21 (m, 2H), 3.53-3.44 (m, 1H), 3.40-3.31 (m, 1H), 2.65 (ddd, J=12.8, 7.8, 4.0 Hz, 1H), 2.05 (ddd, J=13.0, 8.4, 7.0 Hz, 1H), 1.46 (s, 3H), 1.29 (t, J=7.1 Hz, 3H); $^{13}$C NMR (126 MHz, CDCl$_3$) δ 2981, 176.6, 172.2, 61.6, 50.5, 39.4, 34.0, 20.1, 14.1; IR (Neat Film NaCl) 3245, 2981, 1703, 1454, 1266, 1196, 1138, 1028 cm$^{-1}$; HRMS (MM: ESI-APCI+) m/z calc'd for C$_8$H$_{14}$NO$_3$ [M+H]$^+$: 171.0968, found 171.0965.

Isolation and Reduction of Potential Imine Intermediates 34 as a white foam (62 mg, 77% yield, 60/40 mixture of E/Z isomers). $^1$H NMR (500 MHz, CDCl$_3$) for major isomer: δ 7.65-6.62 (m, 8H), 3.86 (s, 3H), 3.76 (ddd, J=9.3, 8.2, 4.6 Hz, 1H), 3.62 (ddd, J=9.3, 7.9, 6.6 Hz, 1H), 2.68 (ddd, J=12.6, 7.9, 4.6 Hz, 1H), 2.17 (ddd, J=12.8, 8.2, 6.6 Hz, 1H), 2.06 (s, 3H), 1.66 (s, 3H); for minor isomer: δ 7.61-6.62 (m, 8H), 4.09 (dt, J=9.1, 7.7 Hz, 1H), 3.85 (s, 3H), 3.82 (td, J=8.8, 3.6 Hz, 1H), 3.15 (ddd, J=12.5, 7.8, 3.6 Hz, 1H), 2.27-2.20 (m, 1H), 2.07 (s, 3H), 1.66 (s, 3H); $^{13}$C NMR (126 MHz, CDCl$_3$) for major and minor isomer: δ 175.1, 174.8, 174.7, 172.2, 156.7, 149.9, 136.1, 135.8, 134.2, 133.3, 132.9, 132.7, 130.1, 129.8, 128.4, 128.3, 128.1, 128.0, 124.8, 124.7, 123.56, 123.4, 122.98, 122.0, 120.59, 120.3, 114.0, 55.8, 55.5, 54.7, 47.0, 46.3, 33.4, 31.2, 22.5, 22.0, 20.5, 20.3; IR (Neat Film NaCl) 2931, 1688, 1512, 1485, 1398, 1289, 1249, 1181, 1090, 1033, 993, 829, 766, 731, 697 cm$^{-1}$; HRMS (MM: ESI-APCI+) m/z calc'd for C$_{26}$H$_{27}$N$_2$O$_2$ [M+H]$^+$: 399.2067, found 399.2072.

(S)-1-(2-Methoxyphenyl)-3-methyl-3-(phenyl(phenylamino)methyl)pyrrolidin-2-one (36)

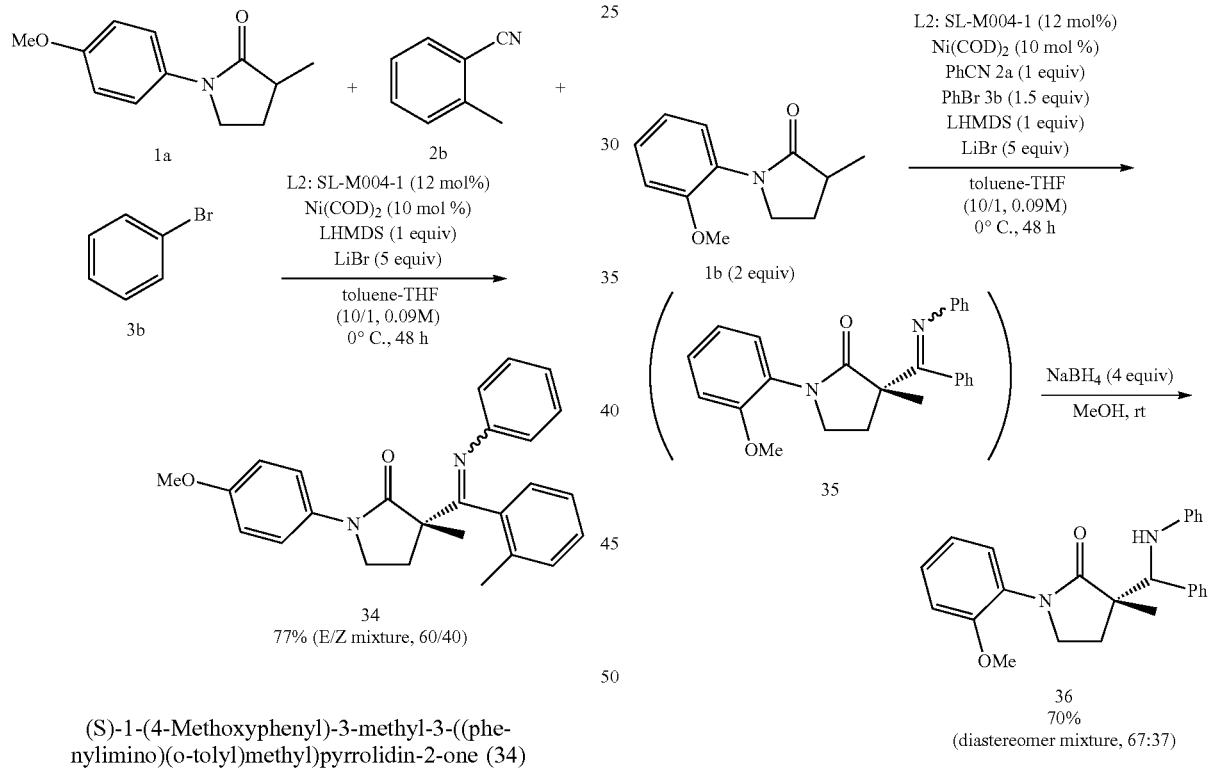

(S)-1-(4-Methoxyphenyl)-3-methyl-3-((phenylimino)(o-tolyl)methyl)pyrrolidin-2-one (34)

To a suspension of lactam 1a (82.1 mg, 0.400 mmol, 2.00 equiv), o-tolunitrile 2b (23.4 mg, 0.200 mmol, 1.00 equiv), bromobenzene 3b (31.5 μL, 0.300 mmol, 1.5 equiv), LHMDS (40.2 mg, 0.240 mmol, 1.20 equiv) and LiBr (86.9 mg, 1.00 mmol, 5.00 equiv) in toluene (1.0 mL) and THF (0.20 mL) were added a solution of Ni(COD)$_2$ (5.50 mg, 0.0200 mmol, 0.100 equiv) and SL-M004-1(Solvias, 25.3 mg, 0.0240 mmol, 0.120 equiv) at 25° C. and the reaction mixture was stirred at 25° C. for 24 h. The reaction mixture was filtered through a pad of silica gel eluting with AcOEt (60 mL). The eluate was concentrated under reduced pressure and the residue was purified by flash column chromatography (1:10 EtOAc:hexanes) on silica gel to give imine To a suspension of lactam 1b (82.1 mg, 0.400 mmol, 2.00 equiv), benzonitrile 2a (20.6 mg, 0.200 mmol, 1.00 equiv), bromobenzene 3b (31.5 μL, 0.300 mmol, 1.5 equiv), LHMDS (40.2 mg, 0.240 mmol, 1.20 equiv) and LiBr (86.9 mg, 1.00 mmol, 5.00 equiv) in toluene (1.0 mL) and THF (0.20 mL) were added a solution of Ni(COD)$_2$ (5.50 mg, 0.0200 mmol, 0.100 equiv) and SL-M004-1 (Solvias, 25.3 mg, 0.0240 mmol, 0.120 equiv) at 0° C. and the reaction mixture was stirred at 0° C. for 48 h. NaBH$_4$ (45.4 mg, 1.20 mmol, 6 equiv), THF (2 mL) and MeOH (2 mL) were added and the reaction mixture was stirred at 25° C. for 2 days. Water was added and the mixture was extracted with AcOEt (50 mL), dried over Na$_2$SO$_4$, and concentrated under reduced pressure. The residue was purified by flash column chromatography (1:5 EtOAc:hexanes) on silica gel to give amine 36 as a colorless oil (54.3 mg, 70% yield).

Spectroscopic data for amine 36 was taken after separation of the diastereomers by flash column chromatography on silica gel.

Major isomer: $^1$H NMR (500 MHz, CDCl$_3$) δ 7.54-7.48 (m, 2H), 7.38-7.31 (m, 2H), 7.31-7.23 (m, 5H), 7.12 (dd, J=7.7, 1.7 Hz, 1H), 7.06-6.99 (m, 2H), 6.99-6.88 (m, 2H), 6.62 (t, J=7.3 Hz, 1H), 6.50 (d, J=7.9 Hz, 2H), 5.51 (s, 1H), 4.50 (s, 1H), 3.63-3.51 (m, 2H), 3.60 (s, 3H), 2.42 (ddd, J=12.7, 7.6, 4.7 Hz, 1H), 1.81 (ddd, J=13.0, 8.3, 6.8 Hz, 1H), 1.34 (s, 3H); $^{13}$C NMR (126 MHz, CDCl$_3$) δ 177.9, 154.9, 148.3, 139.8, 129.0, 128.9, 128.6, 128.6, 128.2, 127.5, 127.0, 120.8, 117.4, 114.1, 112.9, 62.9, 55.4, 47.6, 46.7, 31.0, 19.7; IR (Neat Film NaCl) 3375, 2968, 1678, 1601, 1505, 1455, 1310, 1279, 1260, 1025, 749, 702 cm$^{-1}$; HRMS (MM: ESI-APCI+) m/z calc'd for C$_{25}$H$_{27}$N$_2$O$_2$ [M+H]$^+$: 387.2067, found 387.2070.

Minor isomer: $^1$H NMR (500 MHz, CDCl$_3$) δ 7.48-7.42 (m, 2H), 7.35-7.20 (m, 4H), 7.09-6.98 (m, 3H), 6.98-6.90 (m, 2H), 6.58-6.47 (m, 3H), 6.19 (br s, 1H), 4.37 (s, 1H), 3.78 (s, 3H), 3.41 (td, J=9.1, 4.7 Hz, 1H), 2.62 (ddd, J=9.4, 8.4, 6.4 Hz, 1H), 2.27 (ddd, J=13.1, 8.4, 4.7 Hz, 1H), 1.98 (ddd, J=13.0, 8.9, 6.4 Hz, 1H), 1.61 (s, 3H); $^{13}$C NMR (126 MHz, CDCl$_3$) δ 177.3, 154.6, 147.2, 140.6, 129.0, 128.8, 128.3, 128.3, 127.7, 127.5, 126.8, 120.7, 116.4, 112.9, 112.0, 64.5, 55.6, 47.2, 46.75, 30.8, 24.8; IR (Neat Film NaCl) 3375, 2929, 1674, 1600, 1505, 1455, 1418, 1308, 1256, 1026, 748, 704 cm$^{-1}$; HRMS (MM: ESI-APCI+) m/z calc'd for C$_{25}$H$_{27}$N$_2$O$_2$ [M+H]$^+$: 387.2067, found 387.2071.

REFERENCES

1. For recent reviews on construction of quaternary stereocenters, see: (a) Douglas, C. J.; Overman, L. E. *Proc. Natl. Acad. Sci. U.S.A.* 2004, 101, 5363. (b) Trost, B. M. *Synthesis* 2006, 369. (c) Das, J. P.; Marek, I. *Chem. Commun.* 2011, 47, 4593. (d) Quasdorf, K. W.; Overman, L. E. *Nature* 2014, 516, 181.
2. Liu, Y.; Han, S. J.; Liu, W. B.; Stoltz, B. M. *Acc. Chem. Res.* 2015, 48, 740.
3. Stoltz, B. M.; Bennett, N. B.; Duquette, D. C.; Goldberg, A. F. G.; Liu, Y.; Loewinger, M. B.; Reeves, C. M. Alkylations of Enols and Enolates. In *Comprehensive Organic Synthesis II*, 2nd ed.; Knochel, P., Ed.; Elsevier: Amsterdam, 2014; pp 1-55.
4. (a) Ruble, J. C.; Fu, G. C. *J. Am. Chem. Soc.* 1998, 120, 11532. (b) Shaw, S. A.; Aleman, P.; Vedejs, E. *J. Am. Chem. Soc.* 2003, 125, 13368. (c) Seitzberg, J. G.; Dissing, C.; Sotofte, I.; Norrby, P.-O.; Johannsen, M. *J. Org. Chem.* 2005, 70, 8332. (d) Shaw, S. A.; Aleman, P.; Christy, J.; Kampf, J. W.; Va, P.; Vedejs, E. *J. Am. Chem. Soc.* 2006, 128, 925. (e) Nguyen, H. V.; Butler, D. C. D.; Richards, C. J. *Org. Lett.* 2006, 8, 769. (f) Busto, E.; Gotor-Fernández, V.; Gotor, V. *Adv. Synth. Catal.* 2006, 348, 2626. (g) Dietz, F. R.; Gröger, H. *Synlett* 2008, 663. (h) Dietz, F. R.; Gröger, H. *Synthesis* 2009, 4208. (i) Uraguchi, D.; Koshimoto, K.; Miyake, S.; Ooi, T. *Angew. Chem. Int. Ed.* 2010, 49, 5567. (j) Zhang, Z.; Xie, F.; Jia, J.; Zhang, W. *J. Am. Chem. Soc.* 2010, 132, 15939. (k) Campbell, C. D.; Concellon, C.; Smith, A. D. *Tetrahedron Asymmetry* 2011, 22, 797. (l) De, C. K.; Mittal, N.; Seidel, D. *J. Am. Chem. Soc.* 2011, 133, 16802. (m) Viswambharan, B.; Okimura, T.; Suzuki, S.; Okamoto, S. *J. Org. Chem.* 2011, 76, 6678. (n) Joannesse, C.; Johnston, C. P.; Morrill, L. C.; Woods, P. A.; Kieffer, M.; Nigst, T. A.; Mayr, H.; Lebl, T.; Philp, D.; Bragg, R. A.; Smith, A. D. *Chem. Eur. J.* 2012, 18, 2398. (o) Mandai, H.; Fujiwara, T.; Noda, K.; Fujii, K.; Mitsudo, K.; Korenaga, T.; Suga, S. *Org. Lett.* 2015, 17, 4436.
5. (a) Hills, I. D.; Fu, G. C. *Angew. Chem. Int. Ed.* 2003, 42, 3921. (b) Ismail, M.; Nguyen, H. V.; Ilyashenko, G.; Motevalli, M.; Richards, C. J. *Tetrahedron Lett.* 2009, 50, 6332. (c) Duffey, T. A.; Shaw, S. A.; Vedejs, E. *J. Am. Chem. Soc.* 2009, 131, 14. (d) Wang, M.; Zhang, Z.; Liu, S.; Xie, F.; Zhang, W. *Chem. Commun.* 2014, 50, 1227.
6. (a) Mermerian, A. H.; Fu, G. C. *J. Am. Chem. Soc.* 2003, 125, 4050. (b) Mermerian, A. H.; Fu, G. C. *J. Am. Chem. Soc.* 2005, 127, 5604.
7. (a) Woods, P. A.; Morrill, L. C.; Lebl, T.; Slawin, A. M. Z.; Bragg, R. A.; Smith, A. D. *Org. Lett.*, 2010, 12, 2660. (b) Woods, P. A.; Morrill, L. C.; Bragg, R. A.; Smith, A. D. *Chem. Eur. J.* 2011, 17, 11060.
8. Birrell, J. A.; Desrosiers, J.-N.; Jacobsen, E. N. *J. Am. Chem. Soc.* 2011, 133, 13872.
9. (a) Fleming, I.; Iqbal, J.; Krebs, E.-P. *Tetrahedron* 1983, 39, 841. (b) Mander, L. N.; Sethi, S. P. *Tetrahedron Lett.* 1983, 24, 5425. (c) Crabtree, S. R.; Chu, W. L. A.; Mander, L. N. *Synlett* 1990, 169. (d) Le Roux, C.; Mandrou, S.; Dubac, J. *J. Org. Chem.* 1996, 61, 3885. (e) Wiles, C.; Watts, P.; Haswell, S. J.; Pombo-Villar E. *Tetrahedron Lett.* 2002, 43, 2945.
10. For examples of nitrile additives to improve the reactivity in Ni-based systems, see: (a) Ge, S.; Hartwig, J. F. *J. Am. Chem. Soc.* 2011, 133, 16330. (b) Park, N. H.; Teverovskiy, G.; Buchwald, S. L. *Org. Lett.* 2014, 16, 220. (c) Ge, S.; Green, R. A.; Hartwig, J. F. *J. Am. Chem. Soc.* 2014, 136, 1617. (d) Ge, S.; Green, R. A.; Hartwig, J. F. *Angew. Chem. Int. Ed.* 2015, 54, 3768.
11. Kronenthal, D. R.; Han, C. Y.; Taylor, M. K. *J. Org. Chem.* 1982, 47, 2765.
12. (a) Lindsay, V. N. G.; Nicolas, C.; Charette, A. B. *J. Am. Chem. Soc.* 2011, 133, 8972. (b) Qian, D.; Hu, H.; Liu, F.; Tang, B.; Ye, W.; Wang, Y.; Zhang, J. *Angew. Chem. Int. Ed.* 2014, 53, 13751.
13. Banerjee, S.; Smith, J.; Smith, J.; Faulkner, C.; Masterson, D. S. *J. Org. Chem.* 2012, 77, 10925.
14. Hasserodt, J.; Janda, K. D.; Lerner, R. A. *J. Am. Chem. Soc.* 1997, 119, 5993-5998.
15. Wang, K.-B.; Ran, R.-Q.; Xiu, S.-D.; Li, C.-Y. *Org. Lett.* 2013 15, 2374-2377.
16. Lölsberg, W.; Ye, S.; Schmalz, H. G. *Adv. Synth. Catal.* 2010, 352, 2023-2031.
17. Meiß, R.; Kumar, K.; Waldmann, H. *Chem. Eur. J.* 2015, 21, 13526-13530.
18. Tian, Y.; Wang, Y.; Shang, H.; Xua, X.; Tang Y. *Org. Biomol. Chem.* 2015, 13, 612-619.
19. Kurauchi, D.; Hirano, K.; Kato, H.; Saito, T.; Miyamoto K.; Uchiyama, M. *Tetrahedron* 2015, 71, 5849-5857.
20. Kim, D. D.; Lee, S. J.; Beak, P. *J. Org. Chem.* 2005, 70, 5376-5386.
21. Hayashi, M.; Hashimoto, S.; Stoltz, B. M. *J. Am. Chem. Soc.*, 2016, 138 (29), pp 8997-9000.

Incorporation by Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject disclosure have been discussed, the above specification is illustrative and not restrictive. Many variations of the disclosure will become apparent to those skilled in the art upon review of this specification and the claims below. The full scope of the disclosure should be determined by reference to the claims, along with their full scope of equivalents, and the specification, along with such variations.

What is claimed is:

1. A method for the preparation of a compound of formula (Ia):

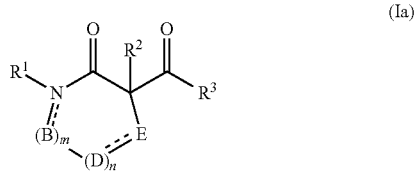

comprising treating a compound of formula (IIa):

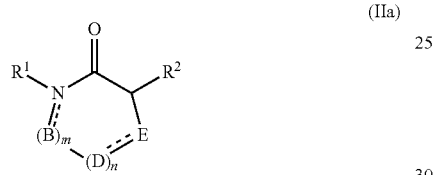

or a salt thereof;
with a complex formed by contacting Ni(COD)$_2$ with a chiral ligand;
an aryl nitrile;
an aryl halide; and
a base;
wherein, as valence and stability permit,
$R^1$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), —OR$^{10}$, —SR', or —NR$^{10}$R$^{11}$;
$R^2$ represents substituted or unsubstituted alkyl, alkenyl, alkynyl, aralkyl, aralkenyl, aryl, heteroaralkyl, heteroaralkenyl, heteroaryl, (cycloalkyl)alkyl, cycloalkyl, (heterocycloalkyl)alkyl, heterocycloalkyl, alkoxy, amino, or halo;
$R^3$ represents substituted or unsubstituted aryl;
B and D independently for each occurrence represent, as valence permits, O, S, NR$^4$, CR$^5$R$^6$, C(O), CR$^5$, or N; provided that no two adjacent occurrences of N, B and D are NR$^4$, O, S, or N;
E represents CR$^5$R$^6$, C(O) or CR$^5$;
$R^4$ represents hydrogen or optionally substituted alkyl, cycloalkyl, (cycloalkyl)alkyl, aryl, aralkyl, heteroaryl, heteroaralkyl, alkenyl, alkynyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), —S(O)$_2$(aryl), —S(O)$_2$(alkyl), —S(O)$_2$(haloalkyl), OR$^{10}$, —SR$^{10}$, or —NR$^{10}$R$^{11}$;
$R^5$ and $R^6$ each independently represent hydrogen, hydroxyl, halogen, nitro, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, cyano, carboxyl, sulfate, amino, alkoxy, aryloxy, arylalkoxy, alkylamino, alkylthio, hydroxyalkyl, alkoxyalkyl, aminoalkyl, thioalkyl, haloalkyl, ether, thioether, ester, amido, thioester, carbonate, carbamate, urea, sulfonate, sulfone, sulfoxide, sulfonamide, acyl, acyloxy, or acylamino;
or any two occurrences of $R^1$, $R^4$, $R^5$, and $R^6$ on adjacent N, B, D, or E groups, taken together with the intervening atoms, form an optionally substituted aryl, heteroaryl, cycloalkyl, cycloalkenyl, heterocycloalkyl, or heterocycloalkenyl group;
each occurrence of === independently represents a double bond or a single bond as permitted by valence;
m and n are integers each independently selected from 0, 1, and 2; and
$R^{10}$ and $R^{11}$ are independently selected for each occurrence from hydrogen or substituted or unsubstituted alkyl, aralkyl, aryl, heteroaralkyl, heteroaryl, (cycloalkyl)alkyl, cycloalkyl, (heterocycloalkyl)alkyl, heterocycloalkyl, alkenyl, and alkynyl.

2. The method of claim 1, wherein the sum of m and n is 0, 1, 2, or 3.

3. The method of claim 1, wherein each occurrence of B, D, and E is independently —CR$^5$R$^6$—, or —CR$^5$—, or —C(O)—.

4. The method of claim 1, wherein E is —CR$^5$R$^6$—; and the sum of m and n is 0.

5. The method of claim 4, wherein
$R^1$ is selected from optionally substituted alkyl, aryl, aralkyl, heteroaryl, heteroaralkyl, alkenyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), and —S(O)$_2$(aryl);
$R^5$ is selected from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, alkylamino, amido, and acylamino; or
$R^1$ and the occurrence of $R^5$ on E are taken together to form an optionally substituted heteroaryl, heterocycloalkyl, or heterocycloalkenyl group.

6. The method of claim 1, wherein the compound of formula (I) is represented by formula (Ib):

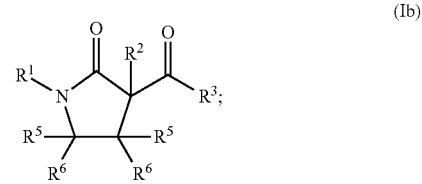

and
the compound of formula (II) is represented by formula (IIb):

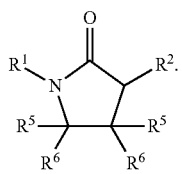

(IIb)

7. The method of claim 6, wherein
R¹ is selected from optionally substituted alkyl, aryl, aralkyl, heteroaryl, heteroaralkyl, alkenyl, —C(O)alkyl, —C(O)aryl, —C(O)aralkyl, —C(O)heteroaryl, —C(O)heteroaralkyl, —C(O)O(alkyl), —C(O)O(aryl), —C(O)O(aralkyl), —C(O)O(heteroaryl), —C(O)O(heteroaralkyl), and —S(O)₂(aryl);
R⁵ is selected from hydrogen, hydroxyl, halogen, alkyl, cycloalkyl, (cycloalkyl)alkyl, aryl, aralkyl, heteroaryl, heteroaralkyl, (heterocycloalkyl)alkyl, heterocycloalkyl, alkenyl, alkynyl, amino, alkoxy, aryloxy, alkylamino, amido, and acylamino; or
R¹ and R⁵ on E are taken together to form an optionally substituted heteroaryl, heterocycloalkyl, or heterocycloalkenyl group.

8. The method of claim 1, wherein R² represents substituted or unsubstituted alkyl, alkenyl, alkynyl, aralkyl, aralkenyl, aryl, heteroaralkyl, heteroaralkenyl, heteroaryl, (cycloalkyl)alkyl, cycloalkyl, (heterocycloalkyl)alkyl, heterocycloalkyl, or halo.

9. The method of claim 1, wherein the complex is present in an amount from about 0.1 mol % to about 20 mol % relative to the compound of formula (II).

10. The method of claim 1, wherein the chiral ligand is an enantioenriched phosphine ligand.

11. The method of claim 1, wherein the chiral ligand is used in an amount from about 0.5 mol % to about 50 mol % relative to the compound of formula (IIa).

12. The method of claim 1, wherein the aryl nitrile is an optionally substituted benzonitrile or a naphthonitrile.

13. The method of claim 1, wherein the treating a compound of formula (IIa) further comprises treating with a lithium salt.

14. The method of claim 1, wherein the treating a compound of formula (IIa) is in the presence of toluene, tetrahydrofuran, dioxane, methyl tert-butyl ether, dimethoxyethane, or a mixture of toluene and tetrahydrofuran.

15. The method of claim 1, whereby the compound of formula (Ia) is enantioenriched.

16. The method of claim 1, wherein:
B, D, and E are each independently CR⁵R⁶, C(O), or CR⁵;
R¹ represents an optionally substituted cycloalkyl, (cycloalkyl)alkyl, aryl, aralkyl, heteroaryl, or heteroaralkyl; and
R² represents substituted or unsubstituted alkyl, alkenyl, alkynyl, aralkyl, aralkenyl, aryl, heteroaralkyl, heteroaralkenyl, heteroaryl, (cycloalkyl)alkyl, cycloalkyl, (heterocycloalkyl)alkyl, or heterocycloalkyl.

17. The method of claim 1, wherein:
B, D, and E are each independently CR⁵R⁶, C(O), or CR⁵;
R¹ represents an optionally substituted cycloalkyl, (cycloalkyl)alkyl, aryl, or aralkyl; and
R² represents substituted or unsubstituted alkyl, alkenyl, alkynyl, aralkyl, aralkenyl, aryl, (cycloalkyl)alkyl, or cycloalkyl.

18. The method of claim 6, wherein:
R¹ represents an optionally substituted cycloalkyl, (cycloalkyl)alkyl, aryl, aralkyl, heteroaryl, heteroaralkyl;
R² represents substituted or unsubstituted alkyl, alkenyl, alkynyl, aralkyl, aralkenyl, aryl, heteroaralkyl, heteroaralkenyl, heteroaryl, (cycloalkyl)alkyl, cycloalkyl, (heterocycloalkyl)alkyl, or heterocycloalkyl; and
R⁵ and R⁶ are hydrogen.

19. The method of claim 6, wherein:
R¹ represents an optionally substituted cycloalkyl, (cycloalkyl)alkyl, aryl, or aralkyl;
R² represents substituted or unsubstituted alkyl, alkenyl, alkynyl, aralkyl, aralkenyl, aryl, (cycloalkyl)alkyl, or cycloalkyl; and
R⁵ and R⁶ are hydrogen.

20. The method of claim 6, wherein the compound of formula (Ib) is selected from:

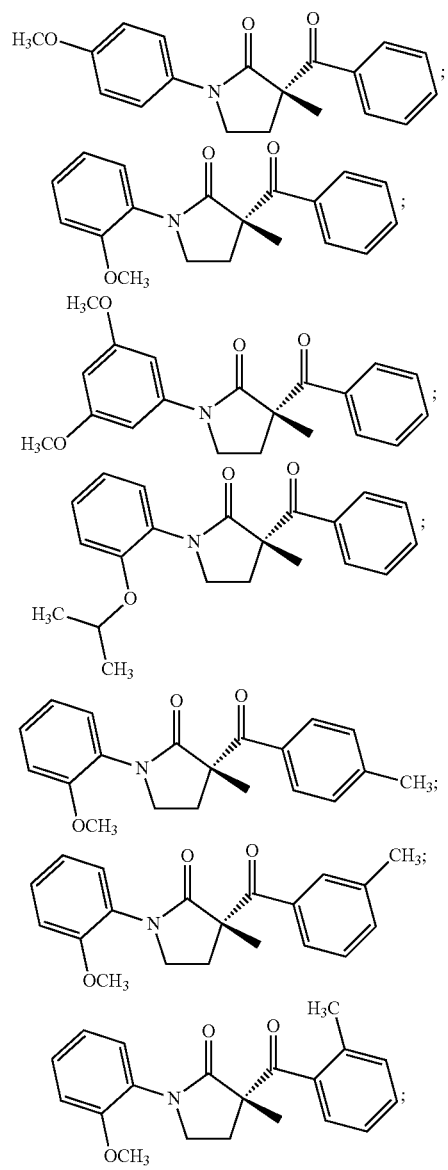

-continued
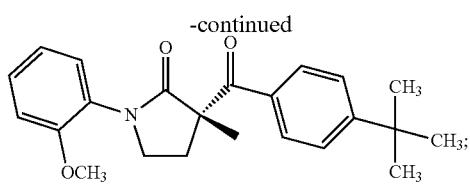
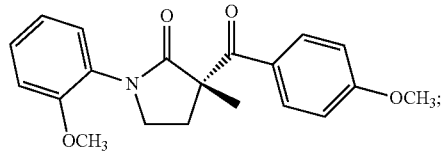
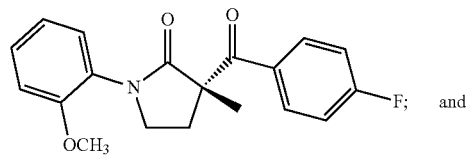 and
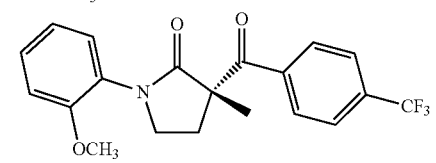
or a salt thereof.
* * * * *

UNITED STATES PATENT AND TRADEMARK OFFICE
CERTIFICATE OF CORRECTION

PATENT NO. : 10,040,784 B2
APPLICATION NO. : 15/454198
DATED : August 7, 2018
INVENTOR(S) : Brian M. Stoltz et al.

Page 1 of 1

It is certified that error appears in the above-identified patent and that said Letters Patent is hereby corrected as shown below:

In the Claims

Claim 1, Line 20, reading "–S(O)$_2$(haloalkyl), –OR$^{10}$, –SR', or –NR$^{10}$R$^{11}$;" should read
-- –S(O)$_2$(haloalkyl), –OR$^{10}$, –SR$^{10}$, or –NR$^{10}$R$^{11}$;--;

Claim 1, Line 39, reading "–S(O)$_2$(haloalkyl), OR$^{10}$, –SR$^{10}$, or –NR$^{10}$R$^{11}$;" should read
-- –S(O)$_2$(haloalkyl), –OR$^{10}$, –SR$^{10}$, or –NR$^{10}$R$^{11}$;--.

Claim 6, second line, reading "(I)" should read --(Ia)--;

Claim 6, fifth line, reading "(II)" should read --(IIa)--.

Claim 9, third line, reading "(II)" should read --(IIa)--.

Signed and Sealed this
Ninth Day of April, 2019

Andrei Iancu
*Director of the United States Patent and Trademark Office*